United States Patent
Wray et al.

(10) Patent No.: US 10,058,514 B2
(45) Date of Patent: Aug. 28, 2018

(54) SILK-BASED SCAFFOLD PLATFORM FOR ENGINEERING TISSUE CONSTRUCTS

(71) Applicant: Tufts University, Medford, MA (US)

(72) Inventors: Lindsay Wray, Benicia, CA (US); Jelena Rnjak-Kovacina, Randwick (AU); David L. Kaplan, Concord, MA (US)

(73) Assignee: TUFTS UNIVERSITY, Medford, MA (US)

( * ) Notice: Subject to any disclaimer, the term of this patent is extended or adjusted under 35 U.S.C. 154(b) by 0 days.

(21) Appl. No.: 15/056,278

(22) Filed: Feb. 29, 2016

(65) Prior Publication Data

US 2017/0027879 A1   Feb. 2, 2017

Related U.S. Application Data

(63) Continuation of application No. 14/356,958, filed as application No. PCT/US2012/064139 on Nov. 8, 2012, now abandoned.

(Continued)

(51) Int. Cl.

| | |
|---|---|
| *A61K 9/70* | (2006.01) |
| *A61K 35/64* | (2015.01) |
| *A61L 27/36* | (2006.01) |
| *A61L 27/38* | (2006.01) |
| *A61L 27/50* | (2006.01) |

(Continued)

(52) U.S. Cl.
CPC ............ *A61K 9/70* (2013.01); *A61K 35/28* (2013.01); *A61K 35/44* (2013.01); *A61K 38/1866* (2013.01); *A61K 47/46* (2013.01); *A61L 27/36* (2013.01); *A61L 27/3687* (2013.01); *A61L 27/3691* (2013.01); *A61L 27/3886* (2013.01);

(Continued)

(58) Field of Classification Search
CPC ............ A61K 9/70; A61K 35/64; A61L 27/36
See application file for complete search history.

(56) References Cited

U.S. PATENT DOCUMENTS

| | | |
|---|---|---|
| 5,245,012 A | 9/1993 | Lombari et al. |
| 6,287,340 B1 | 9/2001 | Altman et al. |

(Continued)

FOREIGN PATENT DOCUMENTS

| | | |
|---|---|---|
| EP | 0404097 A2 | 12/1990 |
| WO | WO-1993/011161 A1 | 6/1993 |

(Continued)

OTHER PUBLICATIONS

Acharya, C. et al, Performance evaluation of a silk protein-based matrix for the enzymatic conversion of tyrosine to L-DOPA, Biotechnology Journal, 3:226-233 (2008).

(Continued)

*Primary Examiner* — Kara Johnson
(74) *Attorney, Agent, or Firm* — Quarles & Brady LLP

(57) ABSTRACT

The inventions provided herein relate to silk-based scaffolds and methods of producing the same, which can be used for a range of tissue engineering applications. The fabrication methods described herein provide a versatile platform to incorporate hollow conduits (e.g., for nutrient/oxygen delivery) through three-dimensional silk-based scaffolds that have tunable bulk properties (e.g., but not limited to, porosity, mechanical, degradation rate) and allow endothelialization and/or cell compartmentalization, for engineering a variety of complex tissue equivalents.

18 Claims, 22 Drawing Sheets

Related U.S. Application Data

(60) Provisional application No. 61/557,064, filed on Nov. 8, 2011.

(51) Int. Cl.
  *A61L 27/54* (2006.01)
  *A61K 35/28* (2015.01)
  *A61K 35/44* (2015.01)
  *A61K 38/18* (2006.01)
  *A61K 47/46* (2006.01)

(52) U.S. Cl.
  CPC ............ *A61L 27/507* (2013.01); *A61L 27/54* (2013.01); *A61L 2300/414* (2013.01)

(56) References Cited

U.S. PATENT DOCUMENTS

| | | |
|---|---|---|
| 6,294,187 B1 | 9/2001 | Boyce et al. |
| 7,635,755 B2 | 12/2009 | Kaplan et al. |
| 7,674,882 B2 | 3/2010 | Kaplan et al. |
| 7,842,780 B2 | 11/2010 | Kaplan et al. |
| 8,071,722 B2 | 12/2011 | Kaplan et al. |
| 8,187,616 B2 | 5/2012 | Wang et al. |
| 8,986,380 B2 | 3/2015 | Kaplan et al. |
| 2003/0157523 A1 | 8/2003 | Frantz et al. |
| 2007/0212730 A1 | 9/2007 | Vepari et al. |
| 2007/0231884 A1 | 10/2007 | Kitagawa et al. |
| 2009/0232963 A1 | 9/2009 | Kaplan et al. |
| 2010/0178304 A1 | 7/2010 | Wang et al. |
| 2010/0279112 A1 | 11/2010 | Kaplan et al. |
| 2011/0171239 A1 | 7/2011 | Kaplan et al. |
| 2013/0310908 A1 | 11/2013 | Omenetto et al. |

FOREIGN PATENT DOCUMENTS

| | | |
|---|---|---|
| WO | WO-1997/008315 A1 | 3/1997 |
| WO | WO-04/000915 A2 | 12/2003 |
| WO | WO-04/001103 A2 | 12/2003 |
| WO | WO-04/062697 A2 | 7/2004 |
| WO | WO-05/000483 A1 | 1/2005 |
| WO | WO-2005/012606 | 2/2005 |
| WO | WO-2005/123114 | 12/2005 |
| WO | WO-2006/042287 A2 | 4/2006 |
| WO | WO-2006/076711 A2 | 7/2006 |
| WO | WO-2007/016524 A2 | 2/2007 |
| WO | WO-2007/103442 A1 | 9/2007 |
| WO | WO-2008/085904 A1 | 7/2008 |
| WO | WO-2008/106485 A2 | 9/2008 |
| WO | WO-2008/108838 A2 | 9/2008 |
| WO | WO-2008/118133 | 10/2008 |
| WO | WO-2008/118211 A2 | 10/2008 |
| WO | WO-2008/127401 A2 | 10/2008 |
| WO | WO-2008/127402 A2 | 10/2008 |
| WO | WO-2008/127403 A2 | 10/2008 |
| WO | WO-2008/127404 A2 | 10/2008 |
| WO | WO-2008/127405 A2 | 10/2008 |
| WO | WO-2008/140562 A2 | 11/2008 |
| WO | WO-2008/150861 A1 | 12/2008 |
| WO | WO-2009/023615 A1 | 2/2009 |
| WO | WO-2009/061823 A1 | 5/2009 |
| WO | WO-2009/100280 A2 | 8/2009 |
| WO | WO-2009/126689 A2 | 10/2009 |
| WO | WO-2009/155397 A2 | 12/2009 |
| WO | WO-2010/036992 A2 | 4/2010 |
| WO | WO-2010/042798 A2 | 4/2010 |
| WO | WO-2010/057142 A2 | 5/2010 |
| WO | WO-2010/087823 A1 | 8/2010 |
| WO | WO-2010/141133 A2 | 12/2010 |
| WO | WO-2010/146574 A1 | 12/2010 |
| WO | WO-2011/005381 A2 | 1/2011 |
| WO | WO-2011/006133 A2 | 1/2011 |
| WO | WO-2011/011347 A2 | 1/2011 |
| WO | WO-2012/145594 A2 | 10/2012 |

OTHER PUBLICATIONS

Altman, G. et al. Cell differentiation by mechanical stress. *The FASEB Journal*, 16(2):270-2 (2002).
Altman, G. H. et al. Silk-based biomaterials. *Biomaterials*, 24:401-416 (2003).
Asahara, T. et al. Synergistic effect of vascular endothelial growth factor and basic fibroblast growth factor on angiogenesis in vivo, Circulation 92:365-71 (1995).
Bagnaninchi, P. et al, Chitosan microchannel scaffolds for tendon tissue engineering characterized using optical coherence tomography, Tissue Eng.,13(2):323-331 (2007).
Banai, S. et al, Angiogenic-induced enhancement of collateral blood flow to ischemic myocardium by vascular endothelial growth factor in dogs, Circulation, 89(5):2183-2189 (1994).
Batzer, M. A., et al., Enhanced evolutionary PCR using oligoneucleotides with inosine at the 3'-terminus, Nucleic Acid Res., 19(18):5081 (1991).
Bauters, C. et al, Recovery of disturbed endothelium-dependent flow in the collateralperfused rabbit ischemic hindlimb after administration of vascular endothelial growth factor, Circulation, 91:2802-2809 (1995).
Bayraktar, O. et al, Silk fibroin as a novel coating material for controlled release of theophylline, European Journal of Pharm. and Biopharm., 60:373-381 (2005).
Carletti, E. et al, Scaffolds for Tissue Engineering and 3D Cell Culture, Methods in Molecular Biology, Chapter 2:17-39 (2011).
Chothia, C. and Lesk, A.M., Canonical Structures for the Hypervariable Regions of Immunoglobulins, J. Mol. Biol., 196: 901-917 (1987).
Demura, M. and Asakura, Immobilization of glucose oxidase with Bombyx mori silk fibroin by only stretching treatment and its application to glucose sensor, Biotech. Bioengin., 33(5): 598-603 (1989).
Fujio, Y. and Walsh, K., Akt mediates cytoprotection of endothelial cells by vascular endothelial growth factor in an anchorage-dependent manner, J. Biol. Chem., 274(23):16349-16354 (1999).
Garcia-Fuentes, M., et al, Silk fibroin/hyaluronan scaffolds for human mesenchymal stem cell culture in tissue engineering, Biomaterials, 30: 5068-5076 (2009).
Georgiou, G. et al., Polylactic acid-phosphate glass composite foams as scaffolds for bone tissue engineering, J. Biomed. Mater. Res. B. Appl. Bio Mater., 80(2): 322-331 (2006).
Gerber, H. P. et al, Vascular endothelial growth factor induces expression of the antiapoptotic proteins Bcl-2 and A1 in vascular endothelial cells, J. Biol.Chem., 273(21):13313-13316 (1998).
Gerber, H. P. et al, Vascular endothelial growth factor regulates endothelial cell survival through the phosphatidylinositol 3'-kinase/Akt signal transduction pathway: Requirement for Flk-1/KDR activation, J. Biol. Chem., 273(46): 30336-30343 (1998).
Ghaznavi, A. M. et al, Silk fibroin conduits: a cellular and functional assessment of peripheral nerve repair, Ann. Plast. Surg., 66(3):273-9 (2011).
Gil, E. S. et al. Mechanical improvements to reinforced porous silk scaffolds, *Journal of Biomedical Materials Research Part A*, 99(1): 16-28 (2011).
Gil, E. S. et al. Mixed Protein Blends Composed of Gelatin and Bombyx m ori Silk Fibroin: Effects of Solvent-Induced Crystallization and Composition. Biomacromolecules 7, 728-735 (2006).
Hofmann, S. et al, Silk fibroin as an organic polymer for controlled drug delivery, Journal of Controlled Release, 111: 219-227 (2006).
Hollinger, P. et al, "Diabodies": Small bivalent and bispecific antibody fragments, Proc. Natl. Acad. Sd. USA, 90: 6444-6448 (1993).
Horan, R. L. et al, In vitro degradation of silk fibroin, Biomaterials, 26:3385-3393 (2005).
Hu, X. et al. Regulation of Silk Material Structure by Temperature-Controlled Water Vapor Annealing, Biomacromolecules, 12(5): 1686-1696 (2011).
Hu, X., et al, Biomaterials derived from silk-tropoelastin protein systems, Biomaterials, 31(32):8121-8131 (2010).
International Search Report for PCT/US2012/064139, 5 pages (dated Mar. 18, 2013).

(56) References Cited

OTHER PUBLICATIONS

Jin et al., Water-Stable Silk Films with Reduced β-Sheet Content, Adv. Funct. Mats., 15: 1241-1247 (2005).
Lesman, A. et al., Transplantation of a tissue-engineered human vascularized cardiac muscle, Tissue Engineering Part A, 16(1):115-125 (2009).
Levenberg, S. et al., Engineering vascularized skeletal muscle tissue, Nat. Biotechnol., 23(7):879-884 (2005).
Lokmic, Z. and Mitchell, G. M., Engineering the microcirculation, Tissue Engineering Part B: Reviews, 14(1): 87-103 (2008).
Lovett, M. et al., Silk fibroin microtubes for blood vessel engineering, Biomaterials, 28(35): 5271-5279 (2007).
Lu, Q. et al., Nanofibrous architecture of silk fibroin scaffolds prepared with a mild self-assembly process, Biomaterials, 32(4):1059-1067 (2011).
Lu, Q. et al., Stabilization and release of enzymes from silk films, Macromolecular Bioscience, 10: 359-368 (2010).
Lu, Q., et al, Green process to prepare silk fibroin/gelatin biomaterial scaffolds, Macromolecular bioscience, 10:289-298 (2010).
Lu, S. et al., Stabilization of enzymes in silk films, Biomacromolecules, 10:1032-1042 (2009).
Lucas, F. et al., The Silk Fibroins, Adv. Protein Chem., 107-242 (1958).
Lv, Q. and Feng, Q. L., Preparation of 3-D regenerated fibroin scaffolds with freeze drying method and freeze drying/foaming technique, J. Mater. Sci. Mater. Med., 17:1349-1356 (2006).
Mandal, B. B. et al High-strength silk protein scaffolds for bone repair, PNAS, 109(20): 7699-7704 (2012).
Meinel, L. et al., The inflammatory responses to silk films in vitro and in vivo, Biomaterials, 26: 147-155 (2005).
Mikos, A. G. et al., Engineering complex tissues, Tissue Eng., 12(12):3307-3339 (2006).
Minoura, N., et al, Fine structure and oxygen permeability of silk fibroin membrane treated with methanol, Polymer, 31: 265-269 (1990).
Miyairi, S. and Sugiura, M., Properties of B-Glucosidase Immobilized in Sericin Membrane, J. Ferment. Technol., 56(4): 303-308 (1978).
Moore, M. J. et al., Multiple-channel scaffolds to promote spinal cord axon regeneration, Biomaterials, 27: 419-429 (2006).
Nazhat, S. N. et al., Controlled microchannelling in dense collagen scaffolds by soluble phosphate glass fibers, Biomacromolecules, 8:543-551 (2007).
Numata, K., et al, Mechanism of enzymatic degradation of beta-sheet crystals, Biomaterials, 31(10):2926 (2010).
Ohtsuka, E. et al., An Alternative Approach to Deoxyoligonucleotides as Hybridization Probes by Insertion of Deoxyinosine at Ambiguous Codon Positions, J. Biol. Chem., 260(5):2605-2608 (1985).
Panilaitis, B. et al., Macrophage responses to silk, Biomaterials, 24:3079-3085 (2003).
Park, J. H. et al., Effect of Heat on Skin Permeability, Intl. J. Pharm., 359(1-2): 94-103 (2008).
Radisic, M. et al., Biomimetic approach to cardiac tissue engineering: oxygen carriers and channeled scaffolds, Tissue Eng., 12(8):2077-2091 (2006).
Rossolini, G.M. et al., Use of deoxyinosine-containing primers vs degenerate primers for polymerase chain reaction based on ambiguous sequence information, Mol. Cell. Probes, 8:91-98 (1994).
Rouwkema, J., et al, Endothelial Cells Assemble into a 3-Dimensional Prevascular Network in a Bone Tissue Engineering Construct, Tissue Eng., 12(9):2685-2693 (2006).
Rouwkema, J., et al, Vascularization in tissue engineering, Trends Biotechnol., 26(8):434-441 (2008).
She, Z. et al, Silk fibroin/chitosan scaffold: preparation, characterization, and culture with HepG2 cell, Journal of Materials Science: Materials in Medicine, 19: 3545-3553 (2008).
She, Z. et al., Preparation and in vitro degradation of porous three-dimensional silk fibroin/chitosan scaffold, Polymer Degradation and Stability, 93(7):1316-1322 (2008).
Unger, R. et al., Endothelialization of a non-woven silk fibroin net for use in tissue engineering: growth and gene regulation of human endothelial cells, Biomaterials, 25:5137-5146 (2004).
Wang, Y. et al, In vivo Degradation of Three-Dimensional Silk Fibroin Scaffolds, Biomaterials, 29(24-25): 3415-3428 (2008).
Wray, L. S. et al. Effect of Processing on Silk-Based Biomaterials: Reproducibility and Biocompatibility, Journal of Biomedical Materials Research Part B, 99(1): 89-101 (2011).
Written Opinion for PCT/US2012/064139, 6 pages (dated Mar. 18, 2013).
Yeo, I. S. et al., Collagen-Based Biomimetic Nanofibrous Scaffolds: Preparation and Characterization of Collagen/Silk Fibroin Bicomponent Nanofibrous Structures, Biomacromolecules, 9(4):1106-1116 (2008).
Zapata, G. et al., Engineering linear F(ab')2 fragments for efficient production in *Escherichia coli* and enhanced antiproliferative activity, Protein Eng., 8(10):1057-1062 (1995).
Zhang, K. H., et al, Fabrication and Intermolecular Interactions of Silk Fibroin/Hydroxybutyl Chitosan Blended Nanofibers, International Journal of Molecular Sciences, 12:2187-2199 (2011).

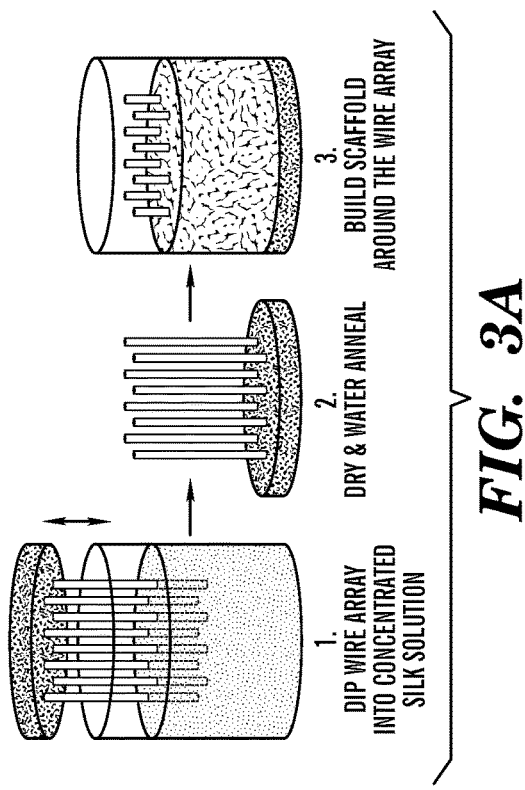
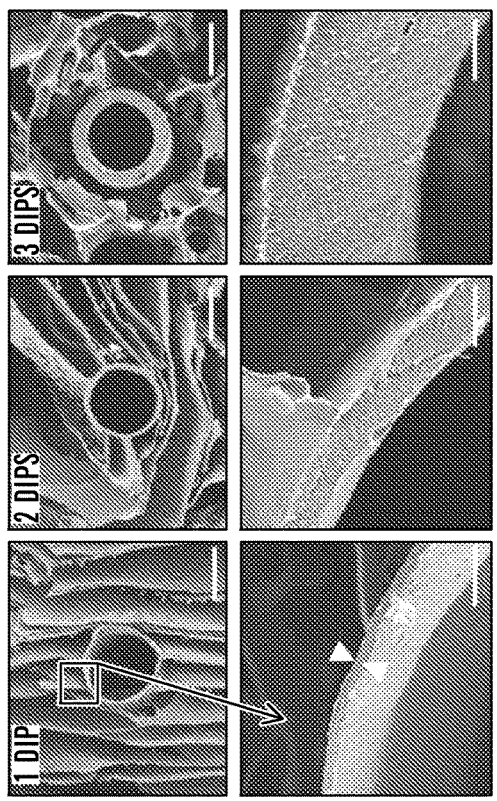
FIG. 3A
FIG. 3B

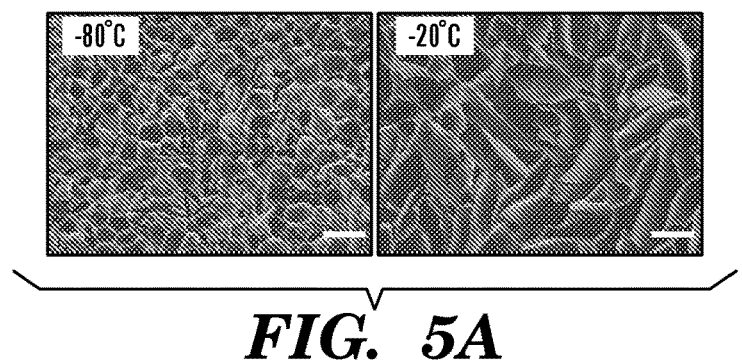
FIG. 5A
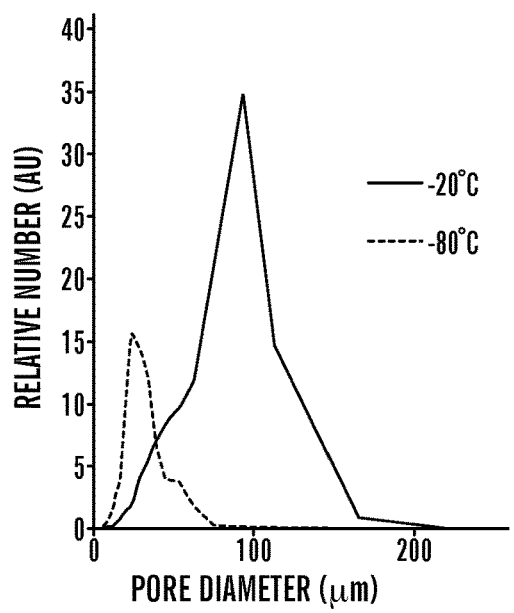
FIG. 5B
| SAMPLE | AVERAGE POROSITY [%] | AVERAGE SURFACE AREA [mm²/g] |
|---|---|---|
| -20°C | 87.2 | 0.7 |
| -80°C | 81.8 | 1.0 |
FIG. 5C

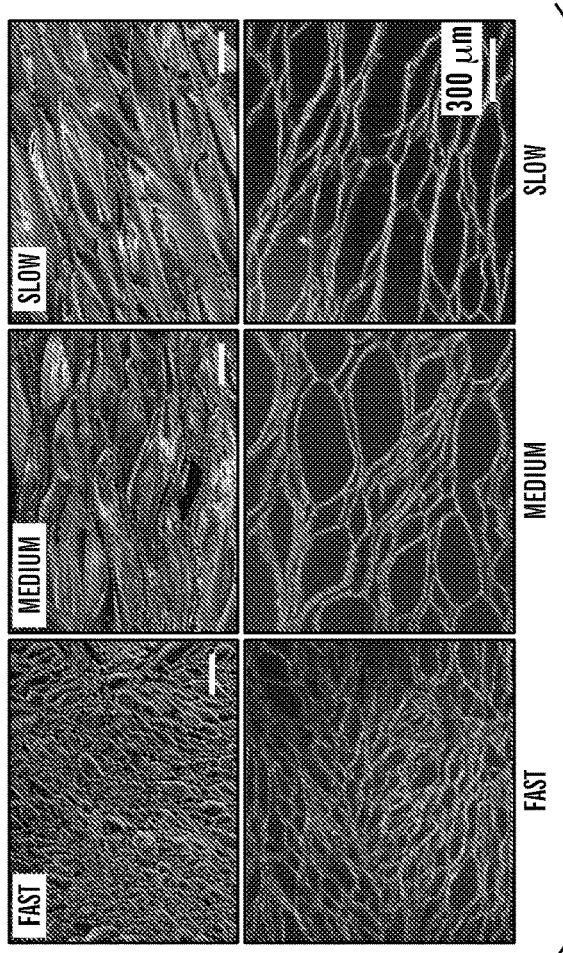
FIG. 6A
FIG. 6B
FIG. 6C

| SAMPLE | AVERAGE POROSITY [%] | AVERAGE SURFACE AREA [mm²/g] |
|---|---|---|
| FAST | 78.8 | 9.7 |
| MEDIUM | 86.1 | 1.6 |
| SLOW | 87.1 | 1.5 |

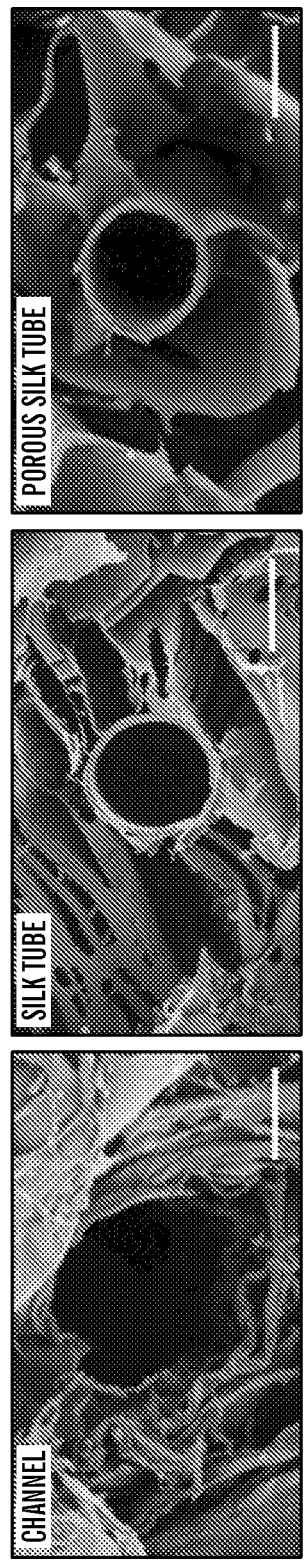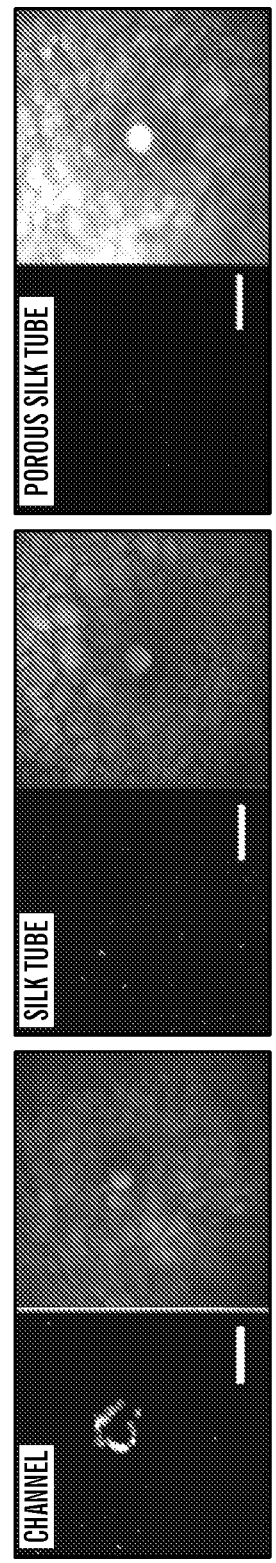
FIG. 8A
FIG. 8B

SILK-BASED SCAFFOLD PLATFORM FOR ENGINEERING TISSUE CONSTRUCTS

CROSS REFERENCE TO RELATED APPLICATIONS

This application is a continuation application of prior filed, co-pending U.S. application Ser. No. 14/356,958, filed May 8, 2014, which is a U.S. national phase application under 35 U.S.C. § 371 of international PCT application no. PCT/US2012/064139, filed Nov. 8, 2012, which claims the benefit of and priority to U.S. Provisional Application No. 61/557,064, filed Nov. 8 ,2011. The entire contents of each of which is hereby incorporated by reference.

GOVERNMENT SUPPORT

This invention was made with government support under grant No. P41 EB002520 awarded by the National Institutes of Health, and grant No. 0806676 awarded by the National Science Foundation. The government has certain rights in the invention.

TECHNICAL FIELD OF THE DISCLOSURE

The inventions described herein relate to silk-based scaffolds and methods of making thereof. In some embodiments, the silk-based scaffolds can be used for various tissue engineering applications.

BACKGROUND

The field of regenerative medicine generally aims to replace damaged and diseased tissues with functional equivalents that will integrate with the host tissue and restore normal function over time. The general approach for engineering tissue constructs is to coordinately combine relevant cell types with biophysical/chemical cues on an appropriate scaffolding material. The scaffolding material for building tissue equivalents plays a significant role in modulating cell behavior and resulting tissue function. To achieve desired tissue function, efforts are taken to optimize scaffold properties such as surface chemistry, porosity, pore morphology, substrate stiffness, and biodegradation rate (Carletti, 2011; Mikos, 2006). In order to systematically design critically-sized, three-dimensional (3D) scaffolds that can serve as complex tissue equivalents it is important to be able to independently tune these properties.

One of the primary obstacles in building critically-sized engineered tissue constructs includes the diffusion limit of oxygen and nutrients. Scaffold constructs that exceed dimensions beyond several hundred micrometers are generally prone to necrosis at the core of the construct and ultimately fail to integrate with host tissue in the long-term due to lack of blood perfusion (Lokmic and Mitchell, 2008; Rouwkema et al., 2008). The natural steps of vascularization within a critically-sized construct do not generally occur within a sufficient time frame to supply the entire construct with necessary oxygen and nutrients. Furthermore, such necrosis can stimulate inflammatory responses in vivo, leading to undesirable outcomes with the implantation of the constructs. Therefore, there is a need in the art for an improved scaffold construct, e.g., for critically-sized tissue engineering applications.

SUMMARY

There is a major need in the field of tissue engineering and regenerative medicine for versatile, fully degradable and implantable large porous biomaterial scaffold systems to support tissue regeneration with vascularization. To this end, the inventors have engineered versatile all protein and degradable silk biomaterial-based 3D tissue constructs that have tunable bulk properties and contain controllable conduits, e.g., for nutrient delivery. In one embodiment, the conduits include an array of linear channels spanning the entire silk-based scaffold. The conduits can be formed prior to formation of the bulk silk matrix around the conduits, e.g., with sequential freezing, lyophilization and additional processing steps to induce additional crystallization ($\beta$-sheet) in the silk biomaterial. The fabrication approach described herein allows for precise control over a wide range of conduit properties, including, but not limited to, conduit diameter, wall-to-wall spacing between conduits, morphology of the conduit wall, loading of an active agent, and any combinations thereof. Additionally or alternatively, the bulk region of solid state silk matrix surrounding the conduits can be prepared with control over a variety of factors, including, but not limited to, pore sizes and morphologies, mechanical properties, degradation rates, and any combinations thereof, for example, by altering silk processing and $\beta$-sheet inducing parameters. The inventors have also demonstrated that, in some embodiments, the conduits, e.g., for nutrient delivery, can further support confluent endothelialization, which is desirable for vascularization of a tissue construct, and that the resulting silk-based scaffold can allow for controlled localization of at least two different cell types within the scaffold. Accordingly, embodiments of various aspects described herein generally relate to silk-based scaffolds and methods or platforms of producing and/or engineering the same, which can be used for a range of tissue engineering applications. Methods for vascularizing an engineered tissue construct are also provided herein.

In one aspect, methods of producing a silk-based scaffold are provided herein. The method comprises: (a) providing an array of elongated structures placed in a silk solution, wherein the elongated structures are arranged in a pre-determined pattern; (b) subjecting the silk solution from step (a) to a condition for forming a solid-state silk matrix; and (c) separating the array of the elongated structures from the solid-state silk matrix to form hollow counterparts in the solid-state silk matrix, thereby producing a silk-based scaffold comprising an array of hollow conduits arranged in the pre-determined pattern.

An array of the elongated structures in a silk solution is placed in a silk solution such that hollow conduits (with a dimension and/or shape corresponding to the elongated structures) can be formed upon removal of the array from the solid-state silk matrix. Accordingly, the size and/or shape of the elongated structures can be selected for desirable size and/or shape of the hollow conduits. For example, the elongated structures can have a cross-sectional shape of a circle, triangle, square, rectangle, oval, a polygonal, an irregular shape, or any combinations thereof. In some embodiments, the elongated structures can have a cross-sectional shape of a circle, such that hollow circular channels are formed in the solid-state silk matrix. In such embodiments, the elongated structures can have a diameter in a range of about 5 μm to about 3000 μm. In some embodiments, the elongated structures can have a diameter in a range of about 5 μm to about 200 μm. In some embodiments, the elongated structures can have a diameter in a range of about 100 μm to about 500 μm. In other embodiments, the elongated structures can have a diameter in a range of about 250 μm to about 1000 μm. In some embodiments, the elongated structures can have a diameter in a range of about 1000 μm to about 3000 μm. In some embodiments, the elongated structures can have a diameter of less than 500 μm, or less than 200 μm.

The elongated structures can be made of any material, e.g., metal, alloy, polymer, plastic, or any combinations thereof. In some embodiments, the elongated structures or at least the surface of the elongated structure can be fabricated from a material that enables easy separation of the array of the elongated structures from the solid-state silk fibroin so that hollow conduits can be formed in the solid-state silk fibroin. In some embodiments, the array of the elongated structures can comprise an array of wires.

The arrangement of the hollow conduits within a silk-based scaffold can be controlled by placement of the elongated structures in a pre-determined pattern. For example, because of the typical diffusion limit of oxygen and nutrients through a matrix, it is more desirable to arrange the hollow conduits in a solid-state silk matrix such that any part of the silk matrix is spatially located from at least one hollow conduit within a diffusion limit, e.g., several micrometers. Accordingly, in one embodiment, the predetermined pattern of the elongated structures can comprise spacing the elongated structures in a manner that results in formation of at least one hollow conduit being spatially located from any part of the silk matrix within a diffusion limit. Such embodiments can be useful for minimizing or reducing the chance of necrosis in any portion of a silk matrix that is otherwise not accessible to nutrient and oxygen transport. In some embodiments, the pre-determined pattern of the elongated structures can comprise spacing at least two of the neighboring elongated structures at a distance in a rage of about 100 μm to about 2000 μm.

In some embodiments, the method described herein can further comprise forming a coating layer around the elongated structures prior to placing the array in the silk solution. The coating layer can comprise at least one biopolymer, e.g., silk. In some embodiments, the coating layer can form at least part of an inner surface of the hollow conduits. In some embodiments, the coating layer can form an intact tubular structure enclosing the hollow conduits.

The coating layer can have any thickness, e.g., of about 1 μm to about 1000 μm, or of about 1 μm to about 100 μm.

In some embodiments, the coating layer can be adapted to be porous. For example, the coating layer can comprise a porogen, which can be removed from the coating layer upon formation of the solid-state silk matrix. Examples of a porogen can include, but are not limited to a water-soluble porogen, e.g., salt, water-soluble polymer, a combination thereof. In one embodiment, a porogen for use to form a porous coating layer can comprise polyethylene oxide. In general, the pore size of the coating layer can be determined, in part, based on the size of the porogen used, while the porosity of the coating layer can be determined, in part, based on the concentration of the porogen used.

In some embodiments, the coating layer and/or the silk solution can further comprise an active agent. Non-limiting examples of an active agent can include proteins, peptides, antigens, immunogens, vaccines, antibodies or portions thereof, antibody-like molecules, enzymes, nucleic acids, siRNA, shRNA, aptamers, viruses, bacteria, small molecules, cells, therapeutic agents, nanoparticles (e.g., silk microfibers) and any combinations thereof.

In addition to a wide range of tunable morphological and/or functionalization properties of the hollow conduits as described herein, physical and/or mechanical properties of the bulk of the solid-state silk matrix can also be altered. For example, the solid-state silk matrix can be present in any material format, e.g., a sponge, a foam, a gel, a lyophilized gel, a mat, a film, or any combinations thereof. In some embodiments, the solid-state silk matrix can be porous. In other embodiments, the solid-state silk matrix can be non-porous. Selection of a suitable material format can vary with tissue engineering applications, e.g., physical and mechanical properties of a target tissue to be mimicked and/or regenerated. In general, any approaches of forming a solid-state silk matrix from a silk solution can be used in the method described herein. For example, the silk solution can be subjected to a condition comprising freezing, drying (e.g., gas-drying), sonication, shear force, electric field, a pH decrease, or any combinations thereof.

In some embodiments, the size, shape and/or orientation of pores as well as porosity within the solid-state silk matrix bulk can be altered by subjecting the silk solution to an appropriate condition for forming a solid-state silk matrix with desirable properties. For example, in some embodiments where the solid-state silk matrix bulk is desired to be porous and/or spongy, the silk solution can be subjected to a condition comprising freezing to form a porous and/or spongy silk matrix. In some embodiments, the frozen silk matrix can be further subjected to lyophilization.

The size, shape, and/or orientation of pores as well as porosity within the solid-state silk matrix bulk can vary with the freezing process parameters, e.g., freezing rate, types of freezing agent, direction of freezing, and any combinations thereof. For example, in some embodiments, the silk solution can be subjected to isotropic freezing thereby forming randomly aligned pores in the bulk of the solid-state silk matrix.

In alternative embodiments, the silk solution can be subjected to unidirectional freezing thereby forming substantially aligned or parallel pores in the bulk of the solid-state silk matrix. In such embodiments, the unidirectional freezing can be performed by a method comprising creating a temperature gradient across the silk solution in one direction, wherein the temperature gradient direction determines the orientation of the pores present in the bulk of the solid-state silk matrix. For example, the temperature gradient can be formed by exposing a portion of the silk solution to a freezing agent, e.g., without limitations, liquid nitrogen, a mixture of dry ice and alcohol, or a combination thereof.

The temperature gradient, in part, determined by the freezing rate can vary with choice of a freezing agent. For example, the freezing rate can range from about 0.05 mm/min to about 10 mm/min. In general, without wishing to be bound by theory, the pore size increases with lower freezing rate. Thus, the freezing rate can be optimized (e.g., by using a different freezing agent) to form pores of a desirable size.

The silk solution can be frozen at any sub-zero temperatures to form a solid-state silk matrix. In some embodiments, the silk solution can be frozen at a temperature of less than −15° C. In some embodiments, the silk solution can be frozen at a temperature of about −80° C. to about −20° C. In some embodiments, the silk solution can be frozen at a temperature of less than −50° C. or lower, e.g., depending on the selection of a freezing agent.

In some embodiments, the solid-state silk matrix can be further exposed to a beta sheet-inducing agent, e.g., water immersion or solvent immersion (e.g., alcohol), for example, to increase additional beta-sheet formation and thus increase insolubility of the solid-state silk matrix in water. Increasing insolubility of the solid-state silk matrix in water can be beneficial for tissue regeneration as it allows the silk-based scaffold retain its volume and/or shape over a longer period of time to support tissue regeneration/integration.

The presence of the hollow conduits in a solid-state silk matrix not only provide an avenue for nutrient and/or oxygen delivery to cells present in a solid-state matrix, but it has also created compartments (e.g., individual hollow conduits and the bulk of the solid-state silk matrix) that enable localization of cells in a specific compartment or that enable localization of different cell types in separate compartments, if needed. Accordingly, in some embodiments, the method can further comprise seeding a cell in the bulk of the solid-state silk matrix, wherein no cell is present in the hollow conduits upon the seeding. In other embodiments, the method can further comprise seeding a cell in at least one of the hollow conduits, wherein no cell is present in the bulk of the solid-state silk matrix upon the seeding. In some embodiments, the method can further comprise seeding a first cell in the bulk of the solid-state silk matrix and seeding a second cell in at least one of the hollow conduits. The first cell can have the same cell type as that of the second cell, or have a different cell type from that of the second cell.

In order to confine the first cell to the bulk of the solid-state silk matrix, in some embodiments, the first cell can be seeded and cultured in the bulk of the solid-state silk matrix for a period of time prior to the separation of the array of the elongated structures from the solid-state silk matrix. Upon removal of the array of the elongated structures, the second cell can then be seeded and cultured in at least one of the hollow conduits, thus enabling compartmentalization of at least two different cell types. Same or different cell types can be seeded and cultured in individual hollow conduits.

In some embodiments, in order to enhance the localization of the seeded cell in the hollow conduit, e.g., preventing the seeded cell from migrating outward to the solid-state silk matrix through interconnected pores, the method described herein can further comprise filling at least a portion of the pores in the bulk of the solid-state silk matrix and/or in the coating layer (if any), prior to the seeding of the cell in the hollow conduit. For example, at least a portion of the pores in the bulk of the solid-state silk matrix and/or in the coating layer (if any) can be filled with a gel, e.g., comprising an extracellular matrix (e.g., a fibrin gel).

In some embodiments, both the first cell and the second cell can be seeded after the separation of the elongated structures from the solid-state silk matrix. In such embodiments, the first cell and the second cell can be dispersed randomly throughout the silk-based scaffold.

The silk solution for use in forming a solid-state silk matrix and/or a coating layer can generally have any concentration. In some embodiments, the silk solution for use in forming a solid-state silk matrix and/or a coating layer can have a concentration of about 1% (w/v) to about 30% (w/v), or of about 3% (w/v) to about 10% (w/v). The optimum concentration of the silk solution can be selected based on a number of factors, e.g., but not limited to, pore size, desired mechanical properties of the solid-sate silk matrix or coating layer.

Without wishing to be bound by theory, appropriate arrangement and/or configuration or architecture of hollow conduits within a silk-based scaffold can provide sufficient nutrient transport and/or endothelialization required to form a viable tissue construct. Accordingly, in some embodiments, the silk-based scaffolds described herein can have no size constraints. For example, the solid-state silk matrix or the silk-based scaffold can have a dimension greater than 0.5 cm, greater than 5 cm, or greater than 10 cm.

The methods described herein can be used to produce silk-based scaffolds that can be cultured in vitro or be implantable for in vivo applications, e.g., for tissue repair and/or regeneration in a subject. Accordingly, another aspect provided herein relates to a silk-based scaffold produced by any embodiment of the methods described herein. In some embodiments, the silk-based scaffold is implantable. For example, a tissue construct comprising a silk-based scaffold produced by any embodiment of the methods is also provided herein.

A further aspect provided herein relates to a silk-based scaffold comprising: a body comprising a plurality of hollow conduits disposed in a solid-state silk matrix, wherein the hollow conduits are arranged in a pre-determined pattern. In some embodiments, at least a portion of the plurality of hollow conduits can extend through the length of the body.

The plurality of the hollow conduits can have a cross-section of any size and/or any shape. For example, in some embodiments, the hollow conduits can have a cross-section with a dimension of about 100 µm to about 1000 µm. In some embodiments, the hollow conduits can have a cross-sectional shape including, but not limited to, a circle, a triangle, a square, an oval, a rectangle, a polygon, an irregular shape, or any combinations thereof.

In some embodiments, it is more desirable to arrange the hollow conduits in a solid-state silk matrix such that any part of the silk matrix is spatially located from at least one hollow conduit within a diffusion limit of oxygen and nutrients, e.g., several micrometers, so that necrosis in any portion of the silk matrix can be minimized or reduced. In some embodiments, the pre-determined pattern of the hollow conduits can comprise spacing at least two of the neighboring elongated structures at a distance in a range of about 100 µm to about 2000 µm. In some embodiments, the pre-determined pattern can comprise an ordered or staggered array of the hollow conduits.

In some embodiments, the periphery of the hollow channel can display open porosity, e.g., similar to that of the solid-state silk matrix bulk. In other embodiments, the periphery of at least one hollow channel can be lined or surrounded by a coating layer. For example, in one embodiment, the coating layer can form at least part of an inner surface of the at least one hollow conduit. In one embodiment, the coating layer can form a tubular structure enclosing the at least one hollow conduit.

The coating layer of the hollow conduits can have any thickness, e.g., of about 1 µm to about 1000 µm, or of about 1 µm to about 100 µm.

The coating layer of the hollow conduits can be porous or non-porous. In some embodiments where the coating layer is porous, the coating layer can have a pore size of about 1 µm to about 20 µm. In some embodiments, the coating layer can have a porosity of at least about 10%.

In addition to the hollow conduits present in the solid-state silk matrix, in some embodiments, the bulk of the solid-state silk matrix (e.g., the solid-state silk matrix surrounding the hollow conduits) can be porous. In such embodiments, the porosity of the bulk of the solid-state silk matrix can be at least about 30%.

The pores in the bulk of the solid-state silk matrix can have any orientation and/or alignment, e.g., depending on the architecture of a target tissue to be mimicked. In some embodiments, the pores in the bulk of the solid-state silk matrix can be randomly-aligned. In other embodiments, the pores in the bulk of the solid-state silk matrix can substantially aligned.

The size and/or shape of the pore in the solid-state silk matrix can vary. For example, the pores can be round or channel-like in the solid-state silk matrix. In some embodiments, the size of the pores can have a width of about 25 μm to about 500 μm, or of about 50 μm to about 250 μm. For elongated pores (e.g., channel-like pores), the size of the pores can have a length of about 50 μm to about 1000 μm, or of about 100 μm to about 700 μm.

In some embodiments, the coating layer and/or the silk solution can further comprise an active agent. Non-limiting examples of an active agent can include proteins, peptides, antigens, immunogens, vaccines, antibodies or portions thereof, antibody-like molecules, enzymes, nucleic acids, siRNA, shRNA, aptamers, viruses, bacteria, small molecules, cells, therapeutic agents, nanoparticles (e.g., silk microfibers) and any combinations thereof.

The solid-state silk matrix and/or the coating layer can have any amounts of silk fibroin. In some embodiments, the solid-state silk matrix and/or the coating layer can be formed from a silk solution prepared at a concentration of about 1% (w/v) to about 30% (w/v). In some embodiments, the solid state silk matrix and/or the coating layer can be formed from a silk solution prepared at a concentration of about 3% (w/v) to about 10% (w/v).

The dimension of the solid-state silk matrix or the body can be selected for various tissue engineering applications, e.g., size of implantable tissue constructs. In some embodiments, the solid-state silk matrix or the body can have a dimension greater than 0.5 cm, greater than 5 cm, or greater than 10 cm.

In some embodiments, the silk-based scaffold can comprise at least one cell. For example, in one embodiment, the bulk of the solid-state silk matrix can further comprise a cell, while no cell is present in the hollow conduits. In another embodiment, at least one hollow conduit can further comprise a cell, while no cell is present in the bulk of the solid-state silk matrix.

In some embodiments, the silk-based scaffold can comprise at least two cells. For example, in some embodiments, the bulk of the solid-state silk matrix can comprise a first cell, and at least one hollow conduit can comprise a second cell. The first cell and the second cell can have the same or different cell type. In some embodiments where more than one hollow conduits comprise a cell, the cell present in a first hollow conduit can have the same cell type as that of the cell present in a second hollow conduit. Alternatively, the cell present in a first hollow conduit can have a different cell type different from that of the cell present in a second hollow conduit.

In some embodiments, the silk-based scaffold can enable endothelialization of the hollow conduits, which in turn pre-vascularize the silk-based scaffold. Accordingly, methods of vascularizing an engineered tissue construct are also provided herein. Such the method comprises: (a) providing at least one embodiment of a silk-based scaffold described herein, wherein a coating layer comprising an endothelialization-inducing agent can form the inner surface of at least one hollow conduit; and (b) forming a layer of endothelial cells on the inner surface of the at least one hollow conduit, thereby pre-vascularizing the silk-based scaffold. In some embodiments, the coating layer can be porous, e.g., to facilitate the interaction and/or attachment of the endothelial cells with the inner surface.

An endothelialization-inducing agent can be any agent that promotes viability, adhesion, and/or function of endothelial cells, e.g., forming a layer of endothelial cells on a surface. For example, an endothelialization-inducing agent can include, but are not limited to, collagen type I, laminin, VEGF, PDGF, or any combination thereof.

In some embodiments, the provided silk-based scaffold can comprise a population of endothelial cells. In alternative embodiments where no endothelial cells are present in the provided silk-based scaffold, the method can further comprise seeding a population of endothelial cells into the at least one hollow conduit.

In some embodiments, the method can further comprise filling at least a portion of the pores in the bulk of the solid-state silk matrix and/or in the coating layer, prior to the seeding of the endothelial cells in the hollow conduit, thereby enhancing the localization of the endothelial cells in the hollow conduit, and thus enhancing the endothelialization of the inner surface of the hollow conduit. In some embodiments, at least a portion of the pores in the bulk of the solid-state silk matrix and/or in the coating layer can be filled with a gel, e.g., comprising an extracellular matrix (e.g., a fibrin gel).

In some embodiments, the method can further comprise seeding a non-endothelial cell in the bulk of the solid-state silk matrix, e.g., depending on types of a tissue construct, e.g., but not limited to, skeletal muscle, cardiac muscle, tendon, ligament, cornea, nervous tissue, or any combinations thereof.

BRIEF DESCRIPTION OF THE DRAWINGS

FIG. 2A is a set of SEM micrographs of channel diameters ranging from 152 μm to 787 μm. FIG. 2B shows channel wall-to-wall spacing ranging between 500 μm and 1000 μm. Top row shows brightfield light microscopy images, while the bottom row shows corresponding SEM images. FIG. 2C shows channel patterning in the parallel (top panel) and offset (bottom panel) configuration. Scale bars are (FIG. 2A) 200 μm, (FIG. 2B) 500 μm, and (FIG. 2C) 1 mm.

FIGS. 3A-3D are images showing hollow channels lined with silk tubes. FIG. 3A is a schematic of the LWA dipping process and subsequent scaffold fabrication, showing that the channel wall was lined with a silk tube by dipping the LWA into a concentrated silk solution, which coated the wires and remained in the scaffold when the LWA was removed. Step 3 in this process figure corresponds to steps 3-6 in FIG. 1. FIGS. 3B-3C indicate that silk tube thickness was determined by the number of times steps 1 and 2 of FIG. 3A were repeated (i.e. number of dips). FIG. 3B shows SEM micrographs of tubes formed by 1, 3 and 5 dips respectively and FIG. 3C shows the average tube thickness as measured by SEM (error bars=s.d.;***p<0.001; n=8). FIG. 3D shows that porous silk tubes were formed by adding a PEO porogen to the concentrated silk solution. (FIGS. 3B and 3D) Scale bars are 100 μm in top row images and 10 μm in bottom row images.

FIG. 4A is a schematic representation of the silk tube functionalization process. The concentrated silk solution was loaded with various agents prior to dipping. Step 3 in this process figure corresponds to steps 3-6 in FIG. 1. FIG. 4B is a set of fluorescent images showing silk tubes of two different diameters (152 μm and 508 μm) functionalized with dextran-fluorescein (green) only or with dextran-fluorescein and dextran-rhodamine (red). FIG. 4C is a set of brightfield images showing silk tubes functionalized with HRP enzyme and incubated with DAB substrate, which turned dark brown in the presence of active HRP. Top and bottom row image show macroscopic and microscopic appearance respectively of a control sample and a HRP functionalized sample. FIG. 4D shows CLSM 3D projection images of hMSCs cultured on scaffolds containing collagen-I ('+COLL') functionalized and unfunctionalized ('−COLL') silk tubes. FIG. 4E is a bar graph showing DNA content of samples in functionalized ('+COLL') or unfunctionalized ('−COLL') silk tubes (error bars=s.d.;*p<0.05; n=3). Scale bars are (FIG. 4B) 150 μm, (FIG. 4C) 100 μm, and (FIG. 4D) 300 μm.

FIGS. 5A-5C show data of scaffold bulk pore morphology, size, and porosity properties when the scaffold was formed by isotropic freezing at −20° C. and −80° C. FIG. 5A is a set of SEM micrographs of scaffold cross-sections showing randomly-oriented pores FIG. 5B is a line graph showing pore size distribution determined by MIP. FIG. 5C is a data table showing scaffold porosity and pore surface area determined by MIP.

FIGS. 6A-6F show data of scaffold bulk pore morphology, size, and porosity properties when the scaffold was formed by a directional freezing method. FIG. 6A is an illustration of an exemplary directional freezing setup. FIG. 6B shows a H&E stained scaffold section showing aligned (parallel) pores. FIG. 6C is a set of SEM micrographs of scaffold cross-sections showing pores created using three different directional freezing rates. 'Fast' freezing rate was 2.9 mm/min, 'Medium' freezing rate was 0.7 mm/min and 'Slow' freezing rate was 0.4 mm/min. FIG. 6D is a line graph showing pore size distribution determined by MIP. FIG. 6E is a data table showing porosity and pore surface area determined by MIP. FIG. 6F is a set of bar graphs showing pore cross-sectional width (left) and length (right) determined from CLSM images (insets) of scaffold cross-sections. Scale bars are 200 μm.

FIG. 7A indicates compressive modulus and FIG. 7B indicates compressive strength. Error bars=s.d.; *** p<0.001 and n=8.

FIGS. 8A-8B are images showing hollow channel morphology and hAEC interactions. FIG. 8A is a set of SEM images showing morphology of hollow channels, and channels lined with non-porous silk tubes and porous silk tubes. FIG. 8B is a set of images showing hAECs interactions with hollow channels at day seven post-seeding. Left-side fluorescent images show cells stained with calcein AM and right-side images show corresponding brightfield light microscope images of the channels. Scale bars are (FIG. 8A) 100 μm and (FIG. 8B) 300 μm.

FIG. 9A is a set of representative CSLM images of hAECs stained with calcein AM (green) interacting with 508 μm diameter silk tubes (control) or silk tubes functionalized with collagen type I, laminin, collagen & VEGF or laminin & VEGF at day seven post-seeding. Scale bar is 300 μm. FIG. 9B is a bar graph showing the level of tube endothelialization by hAECs quantified by assigning each tube an arbitrary value between 1 and 4 corresponding to the level of endothelialization (as described in Example 1). The key below the figure illustrates the level of endothelialization assigned to each value. Error bars=s.d.; *p<0.001 and p<0.01 compared to the control; n=48 (16 tubes/scaffold, 3 scaffolds/treatment).

FIG. 10A is a schematic of the experimental setup. hMSCs were seeded onto the scaffold first in the presence of the LWAs and then seeded with hAECs two days later after removal of the LWAs. FIG. 10B is a set of representative CLSM images of hAECs (red) and hMSCs (cyan). To localize hMSCs to the scaffold bulk and hAECs to the hollow channels, hMSC were seeded in the presence or absence of a fibrin gel (i.e. +/−fibrin) and with or without the LWA in place (i.e. +/−wires). +/−silk tubes refers to the presence of a silk tube lining the periphery of the hollow channel. Scale bars are 300 μm.

FIG. 11A is a schematic representation of the freezing method adopted in a custom-made PDMS chamber to achieve directional/laminar silk scaffold fabrication. FIG. 11B is a photograph showing the actual PDMS device used to fabricate silk laminar scaffolds.

FIG. 12A is a SEM image showing pore/channel alignment and porosity. FIG. 12B is a SEM image of silk scaffold section which was in contact with metal sheet (showing initiation point of laminar channels). FIG. 12C is a fluorescent image showing alignment of fluorescent protein tagged fibroblast cells grown on laminar silk scaffolds. FIG. 12D is a microtome section of laminar scaffold showing interconnectivity and porous channel nature within silk scaffolds.

FIG. 13A is a photograph showing a portion of an exemplary lamellar silk scaffold, with an arrow indicating the freezing direction. FIG. 13B is a H&E image showing a stained scaffold section. FIG. 13C is a confocal microscopy image of lamellar scaffold utilizing silk autofluorescence. FIG. 13D is a SEM image of scaffold lamellae. FIG. 13E is an image showing GFP-tagged fibroblasts grown a lamellar silk scaffold. Scale bars are 200 μm in FIGS. 13B, 13C, and 13E, and 10 μm in FIG. 13D.

DETAILED DESCRIPTION OF THE INVENTION

Figure 1:
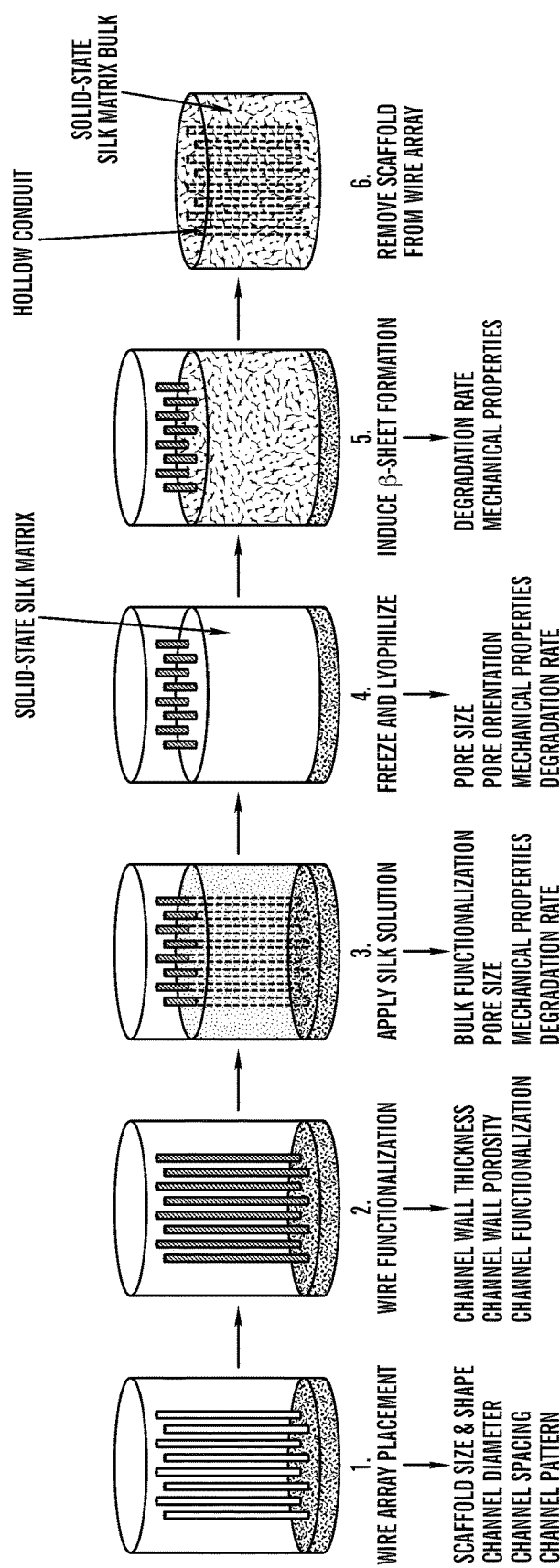
FIG. 1 is a schematic of an exemplary fabrication process for building silk-based porous scaffolds containing hollow conduits (e.g., channels) using an array of elongated structures (e.g., linear wire array (LWA)). At each step in the process there are avenues for tuning the scaffold bulk properties (e.g. porosity, mechanical stiffness, and degradation rate) and the hollow conduit properties (e.g. diameter, spacing, bioactive loading and wall morphology).

There is a clinical demand for three-dimensional (3D) scaffolds with tunable properties and nutrient delivery conduits for engineering complex tissue equivalents. To this end, the inventors have engineered versatile all protein and degradable silk biomaterial-based 3D tissue constructs that have tunable bulk properties and contain controllable conduits, e.g., for nutrient delivery. In one embodiment, the inventors have incorporated the hollow conduits (e.g., for nutrient delivery) into a solid-state silk matrix using linear wire arrays (LWA). The use of LWA can allow for precise control over a wide range of conduit properties, including, but not limited to, diameter of a hollow conduit, wall-to-wall spacing between hollow conduits, morphology of a conduit wall, loading of an active agent, and any combinations thereof. In such embodiment, a solid-state silk matrix is formed around the LWA, e.g., with sequential freezing, lyophilization and β-sheet inducing steps to prevent water solubility of the silk protein. Once the solid-state silk matrix is formed and crystallized, the LWA can be removed, thus producing a silk-based scaffold comprising an array of linear channels therethrough. The inventors have also demonstrate that the bulk space surrounding the hollow conduits (e.g., linear channels) can take on a variety of pore sizes, pore morphologies, degradation rates, and/or mechanical properties, e.g., by altering the silk processing (e.g., freezing) and/or β-sheet inducing parameters. Further, in some embodiments, the conduits, e.g., for nutrient delivery, can further support confluent endothelialization, which is desirable for vascularization of a tissue construct, and that the resulting silk-based scaffold can allow for controlled localization of at least two different cell types within the scaffold. Accordingly, embodiments of various aspects described herein generally relate to silk-based scaffolds and methods or platforms of producing and/or engineering the same, which can be used for a range of tissue engineering applications. Methods for vascularizing an engineered tissue construct are also provided herein.

Methods of Producing a Silk-based Scaffold

In one aspect, methods of producing a silk-based scaffold are provided herein. The method comprises: (a) providing at least one elongated structure placed in a silk solution; (b) subjecting the silk solution from step (a) to a condition for forming a solid-state silk matrix comprising the elongated structure; and (c) separating the elongated structure from the solid-state silk matrix to form a hollow counterpart in the solid-state silk matrix, thereby producing a silk-based scaffold comprising at least one hollow conduit.

In some embodiments, a plurality of (e.g., 2, 3, 4, 5, 6, 7, 8, 9, 10, or more) elongated structures can be placed in a silk solution so that a plurality of corresponding hollow counterparts can be formed in the solid-state silk matrix. In some embodiments, the plurality of elongated structures can be arranged in a pre-determined array pattern. Accordingly, in one embodiment, the method comprises: (a) providing an array of elongated structures placed in a silk solution, wherein the elongated structures are arranged in a pre-determined pattern; (b) subjecting the silk solution from step (a) to a condition for forming a solid-state silk matrix comprising the array of the elongated structures; and (c) separating the array of the elongated structures from the solid-state silk matrix to form hollow counterparts in the solid-state silk matrix, thereby producing a silk-based scaffold comprising an array of hollow conduits arranged in the pre-determined pattern. The required number of elongated structures in an array can vary, e.g., with the size of the silk-based scaffold. Without wishing to be bound, the number of elongated structures in an array can increase with the size of the silk-based scaffold, e.g., to ensure that the silk-based scaffold can obtain sufficient nutrients from the nearby hollow conduits.

At least one elongated structure or an array of the elongated structures is placed in a silk solution such that at least one or more hollow conduits (with a dimension and/or shape corresponding to the elongated structures) can be formed upon removal of the elongated structure(s) from the solid-state silk matrix. Accordingly, the size and/or shape of the elongated structure(s) can be selected for desirable size and/or shape of the hollow conduit(s) formed in the solid-state silk matrix. Where there are more than one elongated structures, the elongated structures in the array can each independently have a certain size and/or shape. For example, the elongated structure(s) can independently have a cross-sectional shape in a circle, a triangle, a square, a rectangle, an oval, a polygonal, an irregular shape, or any combinations thereof.

By way of example only, the elongated structure(s) can have a circular cross-section (e.g., wires) such that hollow cylindrical channel(s) are formed in the solid-state silk matrix. In such embodiments, the elongated structure(s) can have a diameter in a range of about 5 µm to about 3000 µm, or about 10 µm to about 2000 µm, or about 25 µm to about 1500 µm, or about 50 µm to about 1000 µm. In some embodiments, the elongated structure(s) can have a diameter in a range of about 5 µm to about 200 µm. In some embodiments, the elongated structures can have a diameter in a range of about 100 µm to about 500 µm. In other embodiments, the elongated structures can have a diameter in a range of about 250 µm to about 1000 µm, or about 5000 µm to about 1000 µm. In some embodiments, the elongated structures can have a diameter in a range of about 1000 µm to about 3000 µm. In some embodiments, the elongated structures can have a diameter of less than 1000 µm, or less than 500 µm, or less than 200 µm.

The elongated structures can be fabricated from any material, e.g., metal, alloy, polymer, plastic, or any combinations thereof. In some embodiments, the elongated structures or at least the surface of the elongated structures can be fabricated from a material that permits easy separation of the elongated structures from the solid-state silk fibroin so that hollow conduits can be formed in the solid-state silk fibroin. For example, such material can comprise a non-stick material, e.g., polytetrafluoroethylene (PTFE), or any other polymer that does not stick with silk matrix. In one embodiment, the elongated structures comprise PTFE, e.g., PTFE-coated stainless steel wires.

Elongated structures can be arranged in any pre-determined pattern when placed in a silk solution. In general, the placement of the elongated structures is determined based on the desirable arrangement of the hollow conduits within a silk-based scaffold. For example, because of the typical diffusion limit of oxygen and nutrients through a matrix, it is more desirable to arrange the hollow conduits in a solid-state silk matrix such that any part of the silk matrix is spatially located from at least one hollow conduit within a diffusion limit, e.g., several micrometers. Accordingly, in one embodiment, the predetermined pattern of the elongated structures can comprise spacing the elongated structures in a manner that results in formation of at least one hollow conduit spatially located from any part of the silk matrix within a diffusion limit. Such embodiments can be useful for minimizing or reducing the occurrence of necrosis in any portion of a silk matrix that would otherwise not be accessible to nutrient and oxygen transport. In some embodiments, the pre-determined pattern of the elongated structures can comprise positioning apart at least two (including 2, 3, 4, 5, 6, 7, 8, 9, 10, or more) of the neighboring elongated structures by a distance of about 100 µm to about 2000 µm, or about 250 µm to about 1000 µm, or about 500 µm to about 750 µm. In some embodiments, the pre-determined pattern of the elongated structures can comprise an ordered or staggered array of the elongated structures each spaced apart by a fixed distance, e.g., a distance of about 100 µm to about 2000 µm, or about 250 µm to about 1000 µm, or about 500 µm to about 750 µm.

In some embodiments, the method can further comprise forming a coating layer, which will be discussed further below, around the elongated structure(s) prior to placing the elongated structure(s) in the silk solution. Upon separation of the elongated structure(s) from the solid-state silk fibroin, in some embodiments, the coating layer can form at least part of an inner surface of the hollow conduit(s). In some embodiments, the coating layer can form a continuous tubular structure enclosing the hollow conduit(s), for example, as shown in FIG. 3B.

The coating layer around the elongated structure(s) can be formed by any methods known to a skilled artisan, for example, without limitation, dipping, spraying, electrospinning, gel-spinning, or any combinations thereof.

In some embodiments, a coating layer can be formed around elongated structure(s) by dipping the elongated structure(s) in a coating solution comprising at least one biopolymer, including, e.g., at least two, at least three or more biopolymers. Non-limiting examples of a biopolymer that can be used to form a coating layer can include silk, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, other biocompatible and/or biodegradable polymers, and any combinations thereof. See, e.g., International Application Nos.: WO 04/062697; WO 05/012606. In one embodiment, the coating solution can comprise silk. In such embodiment, a concentrated silk solution (e.g., at least about 10% w/v, at least about 15% w/v, at least about 20% w/v, at least about 25% w/v, or at least about 30% w/v) can be used to form a coating layer around the elongated structure(s), e.g., by dipping into a concentrated silk solution the elongated structure(s) at least once or more (to increase the coating thickness), followed by drying and water-annealing, e.g., as shown in the schematic representation in FIG. 3A. Methods for forming a silk-based tubular structure described in Lovett M. et al., "Silk fibroin microtubes for blood vessel engineering." Biomaterials 28, 5271-5279 (2007) and International Pat. App. Nos. WO 2009/126689; and WO2009/023615, the contents of which are incorporated herein by reference, can also be used herein to form a coating layer around elongated structure(s) described herein.

After placing at least one elongated structure or an array of the elongated structure(s) in a silk solution, the silk solution can be subjected to a condition for forming a solid-state silk matrix. In general, any art-recognized approaches of forming a solid-state silk matrix from a silk solution can be used in the method described herein. For example, the silk solution can be subjected to a condition comprising freezing, drying (e.g., gas-drying), sonication, shear force, electric field, a pH decrease, or any combinations thereof. Additional details on forming a solid-state silk matrix from a silk solution can be found, e.g., in U.S. Pat. Nos. 7,674,882; 8,071,722; 7,635,755; 7,842,780; 8,187,616; and International Appl. Nos. WO 2010/087823; WO2011/005381; WO2010/036992, the contents of which are incorporated herein by reference.

An appropriate condition for forming a solid-state silk matrix can be selected, e.g., based on desirable properties (e.g., size, shape, and/or orientation of pores as well as porosity) of the solid-state silk matrix. For example, in some embodiments where the solid-state silk matrix bulk is desired to be porous and/or spongy, the silk solution can be subjected to a condition comprising freezing to form a porous and/or spongy silk matrix. In some embodiments, the frozen silk matrix can be further subjected to lyophilization.

The size, shape, and/or orientation of pores as well as porosity within the solid-state silk matrix bulk can vary with the freezing process parameters, e.g., freezing rate, types of freezing agent, direction of freezing, and any combinations thereof. Typically, ice crystals that formed in the silk solution can act as porogens and determine the features of the pores once the frozen silk matrix is lyophilized.

The silk solution can be frozen at any sub-zero temperatures, e.g., depending on selection of a freezing agent, to form a solid-state silk matrix. In some embodiments, the silk solution can be frozen at a temperature of less than −15° C. In some embodiments, the silk solution can be frozen at a temperature of about −80° C. to about −20° C. In some embodiments, the silk solution can be frozen at a temperature of less than −50° C. or lower, including, e.g., less than −75° C., or less than −80° C., or less than −100° C., or less than −150° C., or less than −175° C., or less than −200° C.

Without wishing to be bound by theory, pore shape and/or orientation can be controlled by freezing direction. For example, in some embodiments, the silk solution can be subjected to isotropic freezing thereby forming randomly-oriented pores (e.g., interconnected round pores as shown in FIG. 5A) in the bulk of the solid-state silk matrix. In one embodiment, the silk solution can be isotropically frozen at about −20° C. In another embodiment, the silk solution can be isotropically frozen at about −80° C.

In alternative embodiments, the silk solution can be subjected to unidirectional freezing thereby forming substantially aligned or parallel pores (e.g., as shown in FIGS. 6B-6C) in the bulk of the solid-state silk matrix. In such embodiments, the unidirectional freezing can be performed by a method comprising creating a temperature gradient across the silk solution in one direction, wherein the temperature gradient direction determines the orientation of the pores present in the bulk of the solid-state silk matrix. For example, the temperature gradient can be formed by exposing a portion of the silk solution to a freezing agent, e.g., without limitations, liquid nitrogen, a mixture of dry ice and alcohol, or a combination thereof. In one embodiment, the silk solution can be subjected to unidirectional freezing in a custom-designed PDMS mold (e.g., as shown in FIG. 6A), e.g., using the protocol described in the Examples.

The freezing rate of the silk solution can affect the pore size formed in the solid-state silk matrix. See, e.g., FIG. 6F. Without wishing to be bound by theory, the pore size typically increases with a slower freezing rate, because a slower freezing rate generally result in larger ice crystal and in turn larger pores. In some embodiments, the freezing rate (e.g., the distance travelled by the freezing front over a period of time) can range from about 0.05 mm/min to about 10 mm/min, 0.1 mm/min to about 5 mm/min, or 0.5 mm/min to about 3 mm/min. A skilled artisan can optimize the freezing rate (e.g., by using different freezing agents) to form pores of a desirable size. For example, in one embodiment, liquid nitrogen can be used to freeze a silk solution at a rate of about 2.5 mm/min to about 3.5 mm/min (e.g., ~3 mm/min). In another embodiment, absolute ethanol and dry ice bath can be used to freeze a silk solution at a rate of about 0.5 mm/min to about 1 mm/min (e.g., ~0.7 mm/min). In another embodiment, less than 100% v/v ethanol (e.g., ~70% v/v) and dry ice bath can be used to freeze a silk solution at a rate of about 0.1 mm/min to about 0.5 mm/min (e.g., ~0.4 mm/min).

In some embodiments, after formation of the solid-state silk matrix, the method can further comprise exposing the solid-state silk matrix to a post-treatment that will affect at least one silk fibroin property. For example, post-treatment of a silk matrix can affect silk fibroin properties including beta-sheet content, solubility, active agent loading capacity, degradation time, active agent permeability or any combinations thereof. Silk post-processing options, e.g., to increase beta-sheet content, include, but not limited to, controlled slow drying (Lu et al., 10 Biomacromolecules 1032 (2009)), water annealing (Jin et al., Water-Stable Silk Films with Reduced β-Sheet Content, 15 Adv. Funct. Mats. 1241 (2005)), stretching (Demura & Asakura, Immobilization of glucose oxidase with *Bombyx mori* silk fibroin by only stretching treatment and its application to glucose sensor, 33 Biotech & Bioengin. 598 (1989)), compressing, and solvent immersion, including methanol (Hofmann et al., 2006), ethanol (Miyairi et al., 1978), glutaraldehyde (Acharya et al., 2008) and 1-ethyl-3-(3-dimethyl aminopropyl) carbodiimide (EDC) (Bayraktar et al., 2005); pH adjustment (see, e.g., U.S. Patent App. No. US2011/0171239, the content of which is incorporated herein by reference), heat treatment, shear stress (see, e.g., International App. No.: WO 2011/005381, the content of which is incorporated herein by reference), sonication (see, e.g., U.S. Pat. App. No. U.S. 2010/0178304 and International App. No.: WO 2008/150861, the contents of which are incorporated herein by reference), and any combinations thereof.

In some embodiments, post-treatment of a silk matrix can increase beta-sheet content in the silk matrix, e.g., by water annealing or solvent immersion such as methanol and/or ethanol.

In some embodiments, post-treatment of a silk matrix, e.g., water-annealing or solvent immersion, can modulate the degradation or solubility properties of the silk matrix (e.g., upon in vivo implantation). In some embodiments, post-treatment of a solid-state silk matrix, e.g., water-annealing or solvent immersion, can control the release of an active agent, if any, from the silk matrix.

Silk-based Scaffolds

The methods described herein can be used to produce silk-based scaffolds that can be cultured in vitro or be implantable for in vivo applications, e.g., for tissue repair and/or regeneration in a subject. Accordingly, another aspect provided herein relates to a silk-based scaffold produced by any embodiment of the methods described herein. In some embodiments, the silk-based scaffold is implantable. For example, a tissue construct comprising a silk-based scaffold produced by any embodiment of the methods is also provided herein.

A further aspect provided herein relates to a silk-based scaffold comprising: a body comprising a plurality of (e.g., 2, 3, 4, 5, 6, 7, 8, 9, 10, or more) hollow conduits disposed in a solid-state silk matrix, wherein the hollow conduits are arranged in a pre-determined pattern. The required number of hollow conduits in a solid-state silk matrix can vary, e.g., with the size of the silk-based scaffold. Without wishing to be bound, the number of hollow conduits can increase with the size of the silk-based scaffold, e.g., to ensure that the silk-based scaffold can obtain sufficient nutrients from the nearby hollow conduits. In some embodiments, at least a portion of the plurality of hollow conduits can extend through the length of the body. In one embodiment, all the hollow conduits extend through the length of the body.

The plurality of the hollow conduits can each independently have a cross-section of any size and/or any shape. For example, in some embodiments, the hollow conduits can each independently have a cross-sectional shape including, but not limited to, a circle, a triangle, a square, an oval, a rectangle, a polygon, an irregular shape, or any combinations thereof. In some embodiments, the hollow conduits can each independently have a cross-section with a dimension of about 5 μm to about 3000 μm, or about 10 μm to about 2000 μm, or about 25 μm to about 1500 μm, or about 50 μm to about 1000 μm. In some embodiments, the hollow conduits can each independently have a cross section with a dimension of about 5 μm to about 200 μm. In some embodiments, the hollow conduits can each independently have a cross section with a dimension of about 100 μm to about 500 μm. In other embodiments, the hollow conduits can each independently have a cross section with a dimension of about 250 μm to about 1000 μm, or about 5000 μm to about 1000 μm. In some embodiments, the hollow conduits can each independently have a cross section with a dimension of about 1000 μm to about 3000 μm. In some embodiments, the hollow conduits can each independently have a cross section with a dimension of less than 1000 μm, or less than 500 μm, or less than 200 μm.

In some embodiments, it is more desirable to arrange the hollow conduits in a solid-state silk matrix such that any part of the silk matrix is spatially located from at least one hollow conduit within a diffusion limit of oxygen and nutrients, e.g., several micrometers, so that necrosis in any portion of the silk matrix can be minimized or reduced. In some embodiments, the pre-determined pattern of the hollow conduits can comprise positioning apart at least two (including 2, 3, 4, 5, 6, 7, 8, 9, 10, or more) of the neighboring hollow conduits by a distance of about 100 μm to about 2000 μm, or about 250 μm to about 1000 μm, or about 500 μm to about 750 μm. In some embodiments, the pre-determined pattern of the hollow conduits can comprise an ordered or staggered array of the hollow conduits each spaced apart by a fixed distance, e.g., a distance of about 100 μm to about 2000 μm, or about 250 μm to about 1000 μm, or about 500 μm to about 750 μm.

In some embodiments, the periphery of the hollow conduit can display open porosity, e.g., similar to that of the solid-state silk matrix bulk (e.g., as shown in FIG. 8A, left panel). In other embodiments, the periphery of at least one hollow conduit can be lined or surrounded by a coating layer (e.g., as shown in FIG. 8A, middle and right panels). For example, in one embodiment, the coating layer can form at least part of an inner surface of the at least one hollow conduit. In one embodiment, the coating layer can form a continuous tubular structure enclosing the at least one hollow conduit.

The dimension of the solid-state silk matrix or the body can be selected for various tissue engineering applications, e.g., size of implantable tissue constructs. In some embodiments, the solid-state silk matrix or the body can have a dimension greater than 0.5 cm, greater than 5 cm, or greater than 10 cm.

In some embodiments, the silk-based scaffold can comprise at least one cell. For example, in one embodiment, the bulk of the solid-state silk matrix can further comprise a cell, while no cell is present in the hollow conduits. In another embodiment, at least one hollow conduit can further comprise a cell, while no cell is present in the bulk of the solid-state silk matrix.

In some embodiments, the silk-based scaffold can comprise at least two cells. For example, in some embodiments, the bulk of the solid-state silk matrix can comprise a first cell, and at least one hollow conduit can comprise a second cell. The first cell and the second cell can have the same or different cell type. In some embodiments where more than one hollow conduits comprise a cell, the cell present in a first hollow conduit can have the same cell type as that of the cell present in a second hollow conduit. Alternatively, the cell present in a first hollow conduit can have a different cell type different from that of the cell present in a second hollow conduit.

Coating Layer Around Elongated Structures (or Hollow Conduits Formed after Removal of the Elongated Structures from a Solid-state Silk Matrix)

The coating layer formed on the surface of the elongated structures described herein or the coating layer enclosing hollow conduits described herein can comprise at least one biopolymer, including, e.g., at least two, at least three or more biopolymers. Non-limiting examples of a biopolymer that can be used to form a coating layer can include silk, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid, other biocompatible and/or biodegradable polymers, and any combinations thereof. See, e.g., International Application Nos.: WO 04/062697; WO 05/012606. In some embodiments, the coating layer can comprise silk. In such embodiment, the coating layer can comprise silk matrix formed from a silk solution of at least 10% w/v, at least about 15% w/v, at least about 20% w/v, at least about 25% w/v, or at least about 30% w/v. In one embodiment, the coating layer can be a silk coating layer formed from a silk solution of at least about 20% w/v.

The coating layer can have any thickness. For example, in some embodiments, the coating layer can have a thickness of about 1 μm to about 1000 μm, or about 1 μm to about 100 μm, or about 1 μm to about 50 μm, or about 1 μm to about 25 μm. In some embodiments, the coating layer can have a thickness similar to a blood vessel wall thickness. The coating layer can be a single layer or a composite of multiple layers.

In some embodiments, the coating layer can be adapted to be porous. For example, the coating layer can comprise a porogen, which can be removed from the coating layer upon formation of the solid-state silk matrix. Examples of a porogen can include, but are not limited to a water-soluble porogen, e.g., salt, water-soluble polymer, or a combination thereof. In one embodiment, a porogen for use to form a porous coating layer can comprise polyethylene oxide. In general, the pore size of the coating layer can be determined, in part, based on the size of the porogen used, while the porosity of the coating layer can be determined, in part, based on the concentration of the porogen used.

The coating layer can be porous or non-porous. As used herein and throughout the specification, the terms "porous" and "porosity" are generally used to describe a structure having a connected network of pores or void spaces (which can, for example, be openings, interstitial spaces or other channels) throughout its volume. The term "porosity" is a measure of void spaces in a material, and is a fraction of volume of voids over the total volume, as a percentage between 0 and 100% (or between 0 and 1).

In some embodiments, the porous coating layer can be configured to have any porosity, depending on the desired properties. For example, in some embodiments, the porous coating layer can have a porosity of at least about 5%, at least about 10%, at least about 20%, at least about 30%, at least about 40%, at least about 50%, at least about 60%, at least about 70%, at least about 80%, at least about 90% or higher, but excluding 100%. In some embodiments, the porosity can range from about 5% to about 50%, or from about 10% to about 30%. The pore size and total porosity values can be quantified using conventional methods and models known to those of skill in the art. For example, the pore size and porosity can be measured by standardized techniques, such as mercury porosimetry and nitrogen adsorption, or the methods described in the Examples. One of ordinary skill in the art can determine the optimal porosity of the coating layer for various purposes. For example, the porosity and/or pore size of the silk fibroin matrices can be optimized based on the cell interaction with the porous surface, release profiles of an active agent from the coating layer, and/or the structural morphology of a blood vessel.

The pores can be adapted to have any shape, e.g., circular, elliptical, or polygonal. The porous coating layer can be adapted to have a pore size of about 0.1 μm to about 30 μm in diameter, about 0.5 μm to about 20 μm in diameter, or about 1 μm to about 20 μm in diameter. The term "pore size" as used herein and throughout the specification refers to a dimension of a pore. In some embodiments, the pore size can refer to the longest dimension of a pore, e.g., a diameter of a pore having a circular cross section, or the length of the longest cross-sectional chord that can be constructed across a pore having a non-circular cross-section. In other embodiments, the pore size can refer to a characteristic length of a pore.

In some embodiments, the coating layer can further comprise at least one active agent as described herein, e.g., an active agent that facilitates at least one cell function, e.g., but not limited to, cell attachment, cell viability and proliferation, cell endothelialization, or any combinations thereof. The active agent can be mixed, dispersed, or suspended in the coating solution such that it becomes distributed or embedded in the resulting coating layer. In some embodiments, the active agent can be introduced into the coating layer, e.g., by incubating the coating layer in a solution comprising an active agent to allow the active agent diffuse into the coating layer. In some embodiments, the active agent can be coated on surfaces of the coating layer.

In some embodiments, the coating layer can be adapted to be insoluble in aqueous environments. For example, a silk coating layer can be made insoluble by increasing its beta-sheet content as described herein.

Silk Solution and Solid-state Silk Matrix

Silk is an FDA-approved protein, possesses excellent biocompatibility and robust, tunable mechanical properties (Panilaitis, 2003; Ghaznavi, 2011; Meinel, 2005). Silk slowly degrades in vivo (i.e. takes months to years to completely resorb) and the degradation rate can be tuned by altering the scaffold processing parameters (Horan, 2005; Wang, 2008). Furthermore the degradation products are non-toxic amino acids (Numata, 2010). The biological properties of silk constructs can be easily augmented through bulk loading, surface decoration or construction of composite materials (Pritchard, 2011). Silk processing and scaffold assembly are performed in aqueous solutions thereby enabling bioactive functionalization of the silk. Furthermore, silk has been shown to stabilize bioactive agents, such as enzymes and therapeutics, thereby prolonging their activity in physiologic conditions (Lu, 2009; Lu, 2010).

The silk solution for use in forming a solid-state silk matrix and/or a coating layer can be aqueous-based or organic solvent-based. In some embodiments, the silk solution for use in forming a solid-state silk matrix and/or a coating layer is aqueous-based. Without wishing to be bound by theory, in some embodiments, the organic solvent-based silk matrix can resist degradation over a longer period of time than the aqueous-based silk matrix. The aqueous- or organic solvent-based silk solution used for making the silk matrix and/or coating layer described herein can be prepared using any techniques known in the art. The concentration of silk in solutions can be suited to a number of factors including, but not limited to, pore size, desired mechanical properties of the solid-sate silk matrix or coating layer. In some embodiments, the silk solution for use in forming a solid-state silk matrix and/or a coating layer can have a concentration of about 1% (w/v) to about 30% (w/v), or about 3% (w/v) to about 20% (w/v). Different concentrations of silk solution can be used to produce a silk matrix and a coating layer. In some embodiments, the silk solution for use in forming a solid-state silk matrix can have a concentration of about 3% (w/v) to about 20% (w/v) or about 4% (w/v) to about 10% (w/v). In some embodiments, the silk solution for use in forming a coating layer can have a concentration of about 10% (w/v) to about 30% (w/v), or about 15% (w/v) to about 25% (w/v). Suitable processes for preparing silk fibroin solution are disclosed, for example, in U.S. Pat. No. 7,635,755; and International Application Nos: WO/2005/012606; and WO/2008/127401. A micro-filtration step can be used herein. For example, the prepared silk fibroin solution can be processed further, e.g., by centrifugation and/or syringe based micro-filtration before further processing into a silk matrix or coating layer described herein.

In some embodiments, the silk solution is silk fibroin solution. As used herein, the term "silk fibroin" includes silkworm fibroin and insect or spider silk protein. See e.g., Lucas et al., 13 Adv. Protein Chem. 107 (1958). Any type of silk fibroin including naturally-derived synthetic silk fibroin may be used according to various aspects described herein. Silk fibroin produced by silkworms, such as *Bombyx mori*, is the most common and represents an earth-friendly, renewable resource. For instance, silk fibroin may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. In some embodiments, silk fibroin for use in the methods described herein can be modified to comprise an active agent or be conjugated to an active agent.

In various embodiments, the silk fibroin can be modified for different applications and/or desired mechanical or chemical properties (e.g., to facilitate formation of a gradient of active agent in silk fibroin matrices). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. Additionally, the silk fibroin matrix can be combined with a chemical, such as glycerol, that, e.g., affects flexibility of the matrix. See, e.g., WO 2010/042798, Modified Silk films Containing Glycerol.

In accordance with various aspects described herein, in addition to a wide range of tunable morphological and/or functionalization properties of the hollow conduits as described herein, physical and/or mechanical properties of the bulk of the solid-state silk matrix can also be altered. For example, the solid-state silk matrix can be present in any material format, e.g., a sponge, a foam, a gel, a lyophilized gel, a mat, a film, or any combinations thereof. Selection of a suitable material format can vary with tissue engineering applications, e.g., physical and mechanical properties of a target native tissue to be mimicked and/or regenerated.

As used herein, the term "silk matrix" generally refers to a composition (e.g., a matrix) comprising silk fibroin. In some embodiments, the term "silk matrix" refers to a composition (e.g., a matrix) in which silk fibroin constitutes at least about 30% of the total composition, including at least about 40%, at least about 50%, at least about 60%, at least about 70%, at least about 80%, at least about 90%, at least about 95% or higher, of the total composition. In certain embodiments, the silk matrix can be 100% silk fibroin. In various embodiments, the silk matrix can be 100% silk fibroin comprising at least one active agent.

The solid-state silk matrix described herein can be adapted to be any shape, e.g., a spherical shape, polygonal-shaped, elliptical-shaped, cylindrical-shaped, tubular-shaped, or any art-recognized shapes. In some embodiments, the solid-state silk matrix described herein can be adapted to a shape similar to a target native tissue to be repaired or regenerated. The size of the silk fibroin matrix can vary with a number of factors including, without limitations, the size of the tissue to be repaired or augmented, the cell population, and/or desired properties of the silk fibroin matrix, e.g., degradation profile.

In some embodiments, the solid-state silk matrix can comprise other biocompatible and/or biodegradable polymers to form mixed polymer matrix comprising silk or silk fibroin. One or more biocompatible and/or biodegradable polymers (e.g., two or more biocompatible polymers) can be added to the silk solution. The biocompatible polymer that can be used herein include, but are not limited to, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible and/or biodegradable polymers. See, e.g., International Application Nos.: WO 04/062697; WO 05/012606.

In some embodiments, at least one active agent described herein can be added to the silk fibroin solution before further processing into a solid-state silk matrix described herein. In some embodiments, the active agent can be dispersed homogeneously or heterogeneously within the silk matrix, dispersed in a gradient, e.g., using the carbodiimide-mediated modification method described in the U.S. Patent Application No. US 2007/0212730.

In some embodiments, the silk matrix can be first formed and then contacted with (e.g., dipped into) at least one active agent such that the open surface of the matrix can be coated with at least one active agent.

In some embodiments, the bulk of the solid-state silk matrix (e.g., the solid-state silk matrix surrounding the hollow conduits) can be non-porous. In some embodiments, the bulk of the solid-state silk matrix (e.g., the solid-state silk matrix surrounding the hollow conduits) can comprise porous structures, e.g., to mimic the structural morphology of a native tissue, to modulate the degradation rate of the silk matrix, and/or to modulate release profile of an active agent embedded therein, if any.

In some embodiments, the porous solid-state silk matrix bulk can be configured to have any porosity, depending on the desired properties. For example, in some embodiments, the porous silk matrix bulk can have a porosity of at least about 30%, at least about 40%, at least about 50%, at least about 60%, at least about 70%, at least about 80%, at least about 90% or higher, but excluding 100%. In some embodiments, the porosity can range from about 70% to about 95%, or from about 75% to about 90%. One of ordinary skill in the art can determine the optimal porosity of the silk matrix bulk for various purposes. For example, the porosity and/or pore size of the silk matrix bulk can be optimized based on the desired degradation rate of the silk matrices, release profiles of an active agent from the silk matrices, and/or the structural morphology of the native tissue to be repaired or regenerated.

The pores in the bulk of the solid-state silk matrix can have any orientation and/or alignment, e.g., depending on the architecture of a target native tissue to be mimicked, and/or silk processing condition (e.g., freezing direction). In some embodiments, the pores in the bulk of the solid-state silk matrix can be randomly-oriented, e.g., as shown in Figure SA. In other embodiments, the pores in the bulk of the solid-state silk matrix can be substantially aligned, e.g., as shown in FIGS. 6B-6C.

The size and/or shape of the pore in the solid-state silk matrix can vary. For example, the pores can be round, oval, polygonal, or channel-like in the solid-state silk matrix. In some embodiments, the size of the pores can have a width of about 25 µm to about 500 µm, or about 50 µm to about 250 µm. For elongated pores (e.g., channel-like pores), the size of the pores can have a length of about 50 µm to about 2000 µm, or about 100 µm to about 1000 µm, or about 200 µm to about 700 µm.

In some embodiments, the elongated pores (e.g., channel-like pores) can have an aspect ratio (e.g., a ratio of pore length to pore width) of about 1 to about 5, or about 2 to about 4.

Methods for generating porous structures within silk fibroin matrix, e.g., freeze-drying, porogen-leaching method (e.g., salt-leaching), and gas foaming methods, are well known in the art and have been described in, e.g., U.S. Pat. No. 7,842,780; and US Patent Application Nos: US 2010/0279112; and US 2010/0279112, the contents of which are incorporated herein by reference in their entirety.

In some embodiments, porous silk matrices can be produced by freeze-drying method. See, e.g., U.S. Pat. No. 7,842,780, and US 2010/0279112. In such embodiments, the silk fibroin solution placed in a non-stick container can be frozen at sub-zero temperatures, e.g., from about −80° C. to about −20° C., for at least about 12 hours, at least about 24 hours, or longer, followed by lyophilization. In one embodiment, the silk solution can be frozen from one direction (e.g., unidirectional freezing).

In certain embodiments, porous silk matrices can be produced by freezing the silk fibroin solution at a temperature range between about −1° C. and about −20° C. or between about −5° C. and −10° C., for at least about 2 days, at least about 3 days or longer, followed by lyophilization for at least about 2 days, at least about 3 days or longer. See, e.g., PCT/US12/34401. The freezing temperature and/or duration, and/or lyophilization duration can be adjusted to generate a silk matrix of different porous structures and/or mechanical properties.

The porosity and/or the porous structures (e.g., pore morphology and/or orientation) in the solid-state silk matrix can affect mechanical properties (e.g., compressive properties) of the solid-state silk matrix and thus the silk-based scaffold. In some embodiments, the solid-state silk matrix (and the silk-based scaffold) can be adapted to have a compressive modulus (e.g., defined as the slope of the linear region of a stress-strain curve between about 2% and about 9% strain) of about 10 kPa to about 1000 kPa, about 25 kPa to about 750 kPa, or about 50 kPa to about 500 kPa. In some embodiments, the solid-state silk matrix can have a compressive modulus of about 10 kPa to about 150 kPa, or about 20 kPa to about 100 kPa, or about 25 kPa to about 75 kPa. In some embodiments, the solid-state silk matrix can have a compressive modulus of about 75 kPa to about 1000 kPa, about 100 kPa to about 750 kPa, or about 150 kPa to about 500 kPa.

In some embodiments, the solid-state silk matrix (and the silk-based scaffold) can be adapted to have a compressive strength (e.g., defined as the stress at intersection of the stress-strain curve and a line parallel to the linear region of the stress-strain curve, offset by about 0.5% strain) of about 1 kPa to about 100 kPa, or about 3 kPa to about 50 kPa. In some embodiments, the solid-state silk matrix can have a compressive strength of about 1 kPa to about 10 kPa. In some embodiments, the solid-state silk matrix can have a compressive strength of about 10 kPa to about 100 kPa, or about 15 kPa to about 50 kPa.

The degradation properties of the bulk of the solid-state silk matrix can be modulated, e.g., in part by the beta-sheet content, pore morphologies and architecture, silk processing methods, and/or silk solution concentration. As used herein, the term "degradation" refers to a decrease in volume or size of the silk matrix. The degradation of the silk matrix can occur via cleavage of the silk matrix into smaller fragments and/or dissolution of the silk matrix or fragments thereof. In some embodiments, the silk matrix can be adapted to degrade no more than 80% of its original volume, including, for example, no more than 70%, no more than 60%, no more than 50%, no more than 40%, no more than 30%, no more than 20%, no more than 10% of its original volume or lower, over a period of time. In some embodiments, the silk matrix can exhibit no significant degradation (e.g., no detectable changes in the volume) upon implantation in a subject. In one embodiment, the silk matrix can be adapted to degrade no more than 50% of its original volume upon implantation in a subject for a period of time. In one embodiment, the silk matrix can be adapted to degrade no more than 40% of its original volume upon implantation in a subject for a period of time. In one embodiment, the silk matrix can be adapted to degrade no more than 30% of its original volume upon implantation in a subject for a period of time. In one embodiment, the silk matrix can be adapted to degrade no more than 20% of its original volume upon implantation in a subject for a period of time. In one embodiment, the silk matrix can be adapted to degrade no more than 10% of its original volume upon implantation in a subject for a period of time.

The bulk of the solid-state silk matrix can be adapted to degrade at any rate. In some embodiments, the silk matrix can be adapted to degrade at least a portion of its original volume over any period of time, e.g., weeks, months, or years. In some embodiments, the silk matrix can be adapted to degrade, e.g., no more than 50% of its original volume (including e.g., no more than 40%, no more than 30%, no more than 20% or lower, of its original volume) in at least about 6 weeks, at least about 7 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 1 year, at least about 2 years, at least about 3 years, at least about 4 years, at least about 5 years or longer. In certain embodiments, the silk matrix can be adapted to degrade, e.g., no more than 30% of its original volume or lower, in at least about 3 months or longer. In other embodiments, there can be no significant degradation (i.e., no detectable changes in the volume of the silk matrix) after placed into a tissue to be repaired or augmented for at least about 3 months or longer. In some embodiments, the silk matrix can be adapted to degrade, e.g., no more than 30% of its original volume or lower, over a period of at least about 6 months or longer (including, e.g., at least about 9 months, at least about 12 months, at least about 18 months or longer). In other embodiments, there can be no significant degradation (i.e., no detectable changes in the volume of the silk matrix) after implantation in a subject over a period of at least about 6 months or longer. In particular embodiments, the silk matrix can be adapted to degrade no more than 80% of its original volume or lower over a period of at least about 1 year or longer (including, for example, at least about 2 years, at least about 3 years, at least about 4 years, at least about 5 years or longer). In some embodiments, the silk matrix can be adapted to degrade no more than 50% of its original volume or lower over a period of at least about 1 year or longer.

Further, the solid-state silk matrix described herein can take advantage of the many techniques developed to functionalize silk matrix or silk fibroin (e.g., active agents such as dyes and sensors). See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287, Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical Microchannel & Method for Fabricating Same; WO 2008/106485, Tissue-Engineered Silk Organs; WO 2008/140562, Electroactive Biopolymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

In an alternative embodiment, the solid-state silk matrices can include plasmonic nanoparticles to form photothermal elements. This approach takes advantage of the superior doping characteristics of silk fibroin. Thermal therapy has been shown to aid in the delivery of various agents, see Park et al., Effect of Heat on Skin Permeability, 359 Intl. J. Pharm. 94 (2008). In one embodiment, short bursts of heat on very limited areas can be used to maximize permeability with minimal harmful effects on surrounding tissues. Thus, plasmonic particle-doped silk matrices can add specificity to thermal therapy by focusing light to locally generate heat only via the silk matrices. In some embodiments, the silk matrices can include photothermal agents such as gold nanoparticles.

Without wishing to be bound by theory, appropriate arrangement and/or configuration or architecture of hollow conduits within a silk-based scaffold can provide sufficient nutrient transport and/or endothelialization required to form a viable tissue construct. Accordingly, in some embodiments, the silk-based scaffolds described herein can have no size constraints. For example, the solid-state silk matrix or the silk-based scaffold can have a dimension greater than 0.5 cm, greater than 5 cm, or greater than 10 cm.

Cell Seeding and/or Compartmentalization and Exemplary Applications

The presence of the hollow conduits in a solid-state silk matrix not only provide an avenue for nutrient and/or oxygen delivery to cells present in a solid-state matrix, but it has also created compartments (e.g., individual hollow conduits and the bulk of the solid-state silk matrix) that enable localization of cells in a specific compartment or that enable localization of different cell types in separate compartments, if needed. Accordingly, in some embodiments, the fabrication method described herein can further comprise seeding a cell in the bulk of the solid-state silk matrix, wherein no cell is present in the hollow conduits upon the seeding. In other embodiments, the method can further comprise seeding a cell in at least one of the hollow conduits, wherein no cell is present in the bulk of the solid-state silk matrix upon the seeding. In some embodiments, the method can further comprise seeding a first cell in the bulk of the solid-state silk matrix and seeding a second cell in at least one of the hollow conduits. The first cell can have the same cell type as that of the second cell, or have a different cell type from that of the second cell.

In order to confine the first cell to the bulk of the solid-state silk matrix, in some embodiments, the first cell can be seeded and cultured in the bulk of the solid-state silk matrix for a period of time prior to the separation of the array of the elongated structures from the solid-state silk matrix. Upon removal of the array of the elongated structures, the second cell can then be seeded and cultured in at least one of the hollow conduits, thus enabling compartmentalization of at least two different cell types. Same or different cell types can be seeded and cultured in individual hollow conduits.

In some embodiments, in order to enhance the localization of the seeded cell in the hollow conduit, e.g., preventing the seeded cell from migrating outward to the solid-state silk matrix through interconnected pores, the method described herein can further comprise filling at least a portion of the pores in the bulk of the solid-state silk matrix and/or in the coating layer (if any), prior to the seeding of the cell in the hollow conduit. For example, at least a portion of the pores in the bulk of the solid-state silk matrix and/or in the coating layer (if any) can be filled with a gel, e.g., comprising an extracellular matrix (e.g., a fibrin gel).

In some embodiments, both the first cell and the second cell can be seeded after the separation of the elongated structures from the solid-state silk matrix. In such embodiments, the first cell and the second cell can be dispersed randomly throughout the silk-based scaffold.

In some embodiments, the silk-based scaffold can enable endothelialization of the hollow conduits, which in turn pre-vascularize the silk-based scaffold. Accordingly, methods of vascularizing an engineered tissue construct are also provided herein. Such the method comprises: (a) providing at least one embodiment of a silk-based scaffold described herein, wherein a coating layer comprising an endothelialization-inducing agent can form the inner surface of at least one hollow conduit; and (b) forming a layer of endothelial cells on the inner surface of the at least one hollow conduit, thereby pre-vascularizing the silk-based scaffold. In some embodiments, the coating layer can be porous, e.g., to facilitate the interaction and/or attachment of the endothelial cells with the inner surface.

An endothelialization-inducing agent can be any agent that promotes viability, adhesion, and/or function of endothelial cells, e.g., forming a layer of endothelial cells on a surface. For example, an endothelialization-inducing agent can include, but are not limited to, collagen type I, laminin, VEGF, PDGF, or any combination thereof.

In some embodiments, the provided silk-based scaffold can comprise a population of endothelial cells. In alternative embodiments where no endothelial cells are present in the provided silk-based scaffold, the method can further comprise seeding a population of endothelial cells into the at least one hollow conduit.

In some embodiments, the method can further comprise filling at least a portion of the pores in the bulk of the solid-state silk matrix and/or in the coating layer, prior to the seeding of the endothelial cells in the hollow conduit, thereby enhancing the localization of the endothelial cells in the hollow conduit, and thus enhancing the endothelialization of the inner surface of the hollow conduit. In some embodiments, at least a portion of the pores in the bulk of the solid-state silk matrix and/or in the coating layer can be filled with a gel, e.g., comprising an extracellular matrix (e.g., a fibrin gel).

In some embodiments, the method can further comprise seeding a non-endothelial cell in the bulk of the solid-state silk matrix, e.g., depending on types of a tissue construct, e.g., but not limited to, skeletal muscle, cardiac muscle, tendon, ligament, cornea, nervous tissue, or any combinations thereof.

In some embodiments, the silk-based scaffold described herein can be sterilized. Sterilization methods for biomedical devices are well known in the art, including, but not limited to, gamma or ultraviolet radiation, autoclaving (e.g., heat/steam); alcohol sterilization (e.g., ethanol and methanol); and gas sterilization (e.g., ethylene oxide sterilization).

Exemplary Active Agents

As described above, the coating layer and/or the solid-state silk matrix can comprise at least one active agent, including, at least two, at least three, at least four or more active agents. The term "active agent" can also encompass combinations or mixtures of two or more active agents, as described below. Non-limiting examples of an active agent can include proteins, peptides, antigens, immunogens, vaccines, antibodies or portions thereof, antibody-like molecules, enzymes, nucleic acids, siRNA, shRNA, aptamers, viruses, bacteria, small molecules, cells, therapeutic agents, nanoparticles (e.g., silk microfibers) and any combinations thereof.

When introducing an active agent such as a therapeutic agent or biological material into a coating layer and/or a solid-state silk matrix described herein, other materials known in the art can also be added with the active agent. For instance, it can be desirable to add materials to promote the growth of the active agent (for biological materials), promote the functionality of the active agent after it is released from the silk fibroin-based composition, or increase the active agent's ability to survive or retain its efficacy during the period it is dispersed in the silk fibroin-based composition. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF I), bone morphogenetic growth factors (BMPs), nerve growth factors, and related proteins can be used.

As different cell types can be cultured in a hollow conduit (including the inner surface of the hollow conduit), and a solid-state silk matrix bulk (including a coating layer, if any), different active agents can also be used in each separate compartment, e.g., based on the cells seeded in each compartment. For example, to enhance endothelialization of the inner surface of the coating layer, the coating layer can comprise an endothelialization-inducing agent, e.g., an agent that promotes viability, adhesion, and/or function of endothelial cells, e.g., forming a layer of endothelial cells on a surface. Examples of an endothelialization-inducing agent can include, but are not limited to, collagen type I, laminin, VEGF, PDGF, or any combination thereof.

In some embodiments, for an implantable tissue construct, the solid-state silk matrix can comprise an agent that increase formation of new tissues and/or stimulates healing or regrowth of native tissue at the site of implantation. Such agents can include, but are not limited to, fibroblast growth factor (FGF), transforming growth factor-beta (TGF- , platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

Cells seeded in a silk-based scaffold, e.g., for use to create a tissue construct can be collected from donors (allogenic) or from recipients (autologous), for example, by cell surface scrape, or needle biopsy or tissue biopsy, or bone marrow aspirate. In some embodiments, the collected cells can be cultured in vitro to expand the population prior to seeding. In some embodiments, the cells used in the methods described herein can be preserved in a liquid medium and stored for a period of time prior to use. In some embodiments, the cells used in the methods described herein can be present in a cell nutrient medium.

The term "cells" used herein generally refers to any eukaryotic, including plant, yeast, worm, insect and mammalian. In some embodiments, the cells can be mammalian cells. Mammalian cells include, without limitation; primate, human and a cell from any animal of interest, including without limitation; mouse, rat, hamster, rabbit, dog, cat, domestic animals, such as equine, bovine, murine, ovine, canine, feline, etc. The cells can be derived from a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoietic, neural, stromal, muscle, cardiovascular, hepatic, pulmonary, and gastrointestinal stem cells and adipose-derived stem cells.

In some embodiments, cells seeded in a silk-based scaffold can comprise human stem cells such as, e.g., mesenchymal stem cells, induced pluripotent stem cells (iPSCs), synovial derived stem cells, embryonic stem cells, adult stem cells, umbilical cord blood cells, umbilical Wharton's jelly cells, osteocytes, fibroblasts, neuronal cells, lipocytes, adipocytes, bone marrow cells, assorted immunocytes, precursor cells derived from adipose tissue, bone marrow derived progenitor cells, peripheral blood progenitor cells, stem cells isolated from adult tissue and genetically transformed cells or combinations of the above cells; or differentiated cells such as, e.g., muscle cells, adipose cells.

Stem cells can be obtained with minimally invasive procedures from bone marrow, adipose tissue, or other sources in the body, are highly expandable in culture, and can be readily induced to differentiate into different progenitor cells after exposure to a well-established differentiation supplement.

A number of different cell types or combinations thereof can be seeded in a silk-based scaffold, depending upon the types of tissues to be repaired or regenerated. These cell types include, but are not limited to: smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. By way of example only, smooth muscle cells and endothelial cells can be seeded in a silk-based scaffold when a muscular and/or vascular tissue construct, such as vascular, esophageal, intestinal, rectal, or ureteral tissues, is desirable; chondrocytes can be seeded in a silk-based scaffold for cartilaginous tissue construct; fibroblasts can be seeded in a silk-based scaffold intended to build a construct for any of the wide variety of tissue types (e.g., skin) that contains extracellular matrix, e.g., collagen; adipocytes can be seeded in a silk-based scaffold intended to create an adipose tissue construct. In general, any cells that are found in the natural tissue can be seeded in a silk-based scaffold to create a corresponding tissue construct. In addition, progenitor cells, such as myoblasts or stem cells, can be seeded in a silk-based scaffold to produce their corresponding differentiated cell types.

Kits

Kits for producing a tissue construct or equivalent for tissue engineering and regenerative medicine applications are also provided herein. In some embodiments, a kit can comprise a silk-based scaffold described herein, and at least one reagent. Examples of a reagent can include, e.g., but are not limited to, cells, cell culture medium, growth factors, and any combinations thereof. In some embodiments, the kit can further comprise a tool, e.g., a tubing adapted to be fitted into the inlet and/or outlet of the hollow conduits of the silk-based scaffold.

Some embodiments of the kit can further comprise instructions, e.g., describing how the contents of the kit are used to carry out one or more methods described herein. Instructions can include steps and conditions necessary to culture cells in the silk-based scaffold for production of a tissue construct or equivalent. Instructions supplied in the kits can include written instructions on a label or package insert (e.g., a paper sheet included in the kit), or machine-readable instructions (e.g., instructions carried on a magnetic or optical storage disk).

Embodiments of the Various Aspects Described Herein can be Illustrated by the Following Numbered Paragraphs.

1. A method of producing a silk-based scaffold comprising:
   a. providing an array of elongated structures placed in a silk solution, wherein the elongated structures are arranged in a pre-determined pattern;
   b. subjecting the silk solution from step (a) to a condition for forming a solid-state silk matrix; and
   c. separating the array of the elongated structures from the solid-state silk matrix to create hollow counterparts in the solid-state silk matrix, thereby producing a silk-based scaffold comprising an array of hollow conduits arranged in the pre-determined pattern.
2. The method of paragraph 1, wherein the condition for forming a solid-state silk matrix comprises freezing, drying, sonication, shear force, electric field, a pH decrease, or any combinations thereof
3. The method of paragraph 1 or 2, wherein the bulk of the solid-state silk matrix is porous.
4. The method of paragraph 3, wherein the condition for forming a solid-state porous silk matrix comprises freezing.

5. The method of paragraph 4, wherein the freezing includes isotropic freezing for forming randomly aligned pores in the bulk of the solid-state silk matrix.
6. The method of paragraph 4, wherein the freezing includes unidirectional freezing for forming substantially aligned or parallel pores in the bulk of the solid-state silk matrix.
7. The method of paragraph 6, wherein the unidirectional freezing is performed by a method comprising creating a temperature gradient across the silk solution in step (b) in one direction, wherein the temperature gradient direction determines the orientation of the pores present in the bulk of the solid-state silk matrix.
8. The method of paragraph 6, wherein the temperature gradient is formed by exposing a portion of the silk solution to a freezing agent.
9. The method of paragraph 8, wherein the freezing agent comprises liquid nitrogen, a mixture of dry ice and alcohol, or a combination thereof
10. The method of any of paragraphs 2-9, wherein the freezing further comprises lyophilization.
11. The method of any of paragraphs 1-10, wherein the elongated structures have a diameter in a range of about 100 μm to about 1000 μm.
12. The method of any of paragraphs 1-10, wherein the elongated structures have a diameter of less than 500 μm, or less than 200 μm.
13. The method of any of paragraphs 1-12, wherein the array of the elongated structures comprises an array of wires.
14. The method of any of paragraphs 1-13, wherein the pre-determined pattern comprises spacing at least two of the neighboring elongated structures at a distance in a rage of about 100 μm to about 2000 μm.
15. The method of any of paragraphs 1-14, further comprising forming a coating layer around the elongated structures prior to placing the array in the silk solution.
16. The method of paragraph 15, wherein the coating layer comprise silk.
17. The method of any of paragraphs 15-16, wherein the coating layer forms the inner surface of the hollow conduits.
18. The method of any of paragraphs 15-17, wherein the coating layer forms a tubular structure enclosing the hollow conduits.
19. The method of any of paragraphs 15-18, wherein the coating layer has a thickness of about 1 μm to about 1000 μm, or of about 1 μm to about 100 μm.
20. The method of any of paragraphs 15-19, wherein the coating layer is adapted to be porous.
21. The method of paragraph 20, wherein the coating layer comprises a porogen.
22. The method of paragraph 21, wherein the porogen is removed from the coating layer upon the formation of a solid-state matrix in step (b).
23. The method of paragraph 21 or 22, wherein the porogen is removed from the coating layer upon the formation of the solid-state silk matrix.
24. The method of any of paragraphs 21-23, wherein the porogen comprises a water-soluble porogen.
25. The method of paragraph 24, wherein the water-soluble porogen comprises salt, water-soluble polymer, or a combination thereof
26. The method of paragraph 25, wherein the water-soluble polymer comprise polyethylene oxide.
27. The method of any of paragraphs 15-26, wherein the coating layer further comprises an active agent.
28. The method of any of paragraphs 1-27, wherein the silk solution further comprises an active agent.
29. The method of paragraph 27 or 28, wherein the active agent is selected from the group consisting of proteins, peptides, antigens, immunogens, vaccines, antibodies or portions thereof, antibody-like molecules, enzymes, nucleic acids, siRNA, shRNA, aptamers, viruses, bacteria, small molecules, cells, therapeutic agents, nanoparticles, and any combinations thereof
30. The method of any of paragraphs 1-29, further comprising exposing the solid-state silk matrix to a post-treatment.
31. The method of paragraph 30, wherein the post-treatment increases beta sheet content in the solid-state silk matrix.
32. The method of any of paragraphs 1-31, further comprising seeding a cell in the bulk of the solid-state silk matrix, wherein no cell is present in the hollow conduits upon the seeding.
33. The method of any of paragraphs 1-31, further comprising seeding a cell in at least one of the hollow conduits, wherein no cell is present in the bulk of the solid-state silk matrix upon the seeding.
34. The method of any of paragraphs 1-31, further comprising seeding a first cell in the bulk of the solid-state silk matrix and seeding a second cell in at least one of the hollow conduits.
35. The method of paragraph 34, wherein the first cell has the same cell type as that of the second cell.
36. The method of paragraph 34, wherein the first cell has a different cell type from that of the second cell.
37. The method of any of paragraphs 32-36, wherein either one or both of the first cell and the second cell are seeded after performing the step (c).
38. The method of any of paragraphs 32-37, wherein the cell or the first cell is seeded and cultured in the bulk of the solid-state silk matrix for a period of time prior to performing the step (c), thereby localizing the cell or the first cell in the bulk of the solid-state silk matrix.
39. The method of any of paragraphs 33-38, further comprising filling at least a portion of the pores in the bulk of the solid-state silk matrix and/or in the coating layer, prior to the seeding of the cell or the second cell in the hollow conduit, thereby enhancing the localization of the cell or the second cell in the hollow conduit.
40. The method of paragraph 39, wherein said at least a portion of the pores in the bulk of the solid-state silk matrix and/or in the coating layer is filled with a gel.
41. The method of paragraph 40, wherein the gel comprises an extracellular matrix.
42. The method of any of paragraphs 1-41, wherein the silk solution has a concentration of about 1% (w/v) to about 30% (w/v).
43. The method of any of paragraphs 1-42, wherein the silk solution has a concentration of about 3% (w/v) to about 10% (w/v).
44. The method of any of paragraphs 1-43, wherein the solid-state silk matrix has a dimension greater than 0.5 cm.
45. The method of any of paragraphs 1-44, wherein the solid-state silk matrix has a dimension greater than 5 cm, or greater than 10 cm.
46. A silk-based scaffold produced by the methods of any of paragraphs 1-45.
47. A silk-based scaffold comprising:
    a body comprising a plurality of hollow conduits disposed in a solid-state silk matrix, wherein the hollow conduits are arranged in a pre-determined pattern.

48. The scaffold of paragraph 47, wherein at least a portion of the plurality of hollow conduits extend through the length of the body.
49. The scaffold of paragraph 47 or 48, wherein the plurality of hollow conduits has a cross-sectional shape selected from the group consisting of a circle, a triangle, a square, an oval, a rectangle, a polygon, an irregular shape, or any combinations thereof
50. The scaffold of any of paragraphs 47-49, wherein the hollow conduits have a cross-section with a dimension of about 100 µm to about 1000 µm.
51. The scaffold of any of paragraphs 47-50, wherein the pre-determined pattern comprises spacing at least two of the neighboring elongated structures at a distance in a range of about 100 µm to about 2000 µm.
52. The scaffold of any of paragraphs 47-51, wherein the pre-determined pattern comprises an ordered or staggered array of the hollow conduits.
53. The scaffold of any of paragraphs 47-52, wherein at least one hollow conduit is lined or surrounded by a coating layer.
54. The scaffold of paragraph 53, wherein the coating layer forms the inner surface of said at least one hollow conduit.
55. The scaffold of paragraph 53 or 54, wherein the coating layer forms a tubular structure enclosing said at least one hollow conduit.
56. The scaffold of any of paragraphs 53-55, wherein the coating layer has a thickness of about 1 µm to about 1000 µm, or of about 1 µm to about 100 µm.
57. The scaffold of any of paragraphs 53-56, wherein the coating layer is porous.
58. The scaffold of any of paragraphs 53-57, wherein the coating layer has a pore size of about 1 µm to about 20 µm.
59. The scaffold of any of paragraphs 53-58, wherein the coating layer has a porosity of at least about 10%.
60. The scaffold of any of paragraphs 47-59, wherein the bulk of the solid-state silk matrix is porous.
61. The scaffold of paragraph 60, wherein the porosity of the bulk of the solid-state silk matrix is at least about 30%.
62. The scaffold of paragraph 60 or 61, wherein the pores in the bulk of the solid-state silk matrix are randomly-aligned.
63. The scaffold of paragraph 60 or 61, wherein the pores in the bulk of the solid-state silk matrix are substantially aligned.
64. The scaffold of any of paragraphs 60-63, wherein the size of the pore in the solid-state silk matrix has a width of about 25 µm to about 500 µm, or of about 50 µm to about 250 µm.
65. The scaffold of any of paragraphs 60-64, wherein the size of the pore in the solid-state silk matrix has a length of about 50 µm to about 1000 µm, or of about 100 µm to about 700 µm.
66. The scaffold of any of paragraphs 47-65, wherein either one or both of the solid state silk matrix and the coating layer comprise an active agent.
67. The scaffold of paragraph 66, wherein the active agent is selected from the group consisting of proteins, peptides, antigens, immunogens, vaccines, antibodies or portions thereof, antibody-like molecules, enzymes, nucleic acids, siRNA, shRNA, aptamers, viruses, bacteria, small molecules, cells, therapeutic agents, nanoparticles, and any combinations thereof
68. The scaffold of any of paragraphs 1-67, wherein the solid state silk matrix is formed from a silk solution prepared at a concentration of about 1% (w/v) to about 30% (w/v).
69. The scaffold of any of paragraphs 1-68, wherein the solid state silk matrix is formed from a silk solution prepared at a concentration of about 3% (w/v) to about 10% (w/v).
70. The scaffold of any of paragraphs 1-69, wherein the solid-state silk matrix has a dimension greater than 0.5 cm.
71. The scaffold of any of paragraphs 1-70, wherein the solid-state silk matrix has a dimension greater than 5 cm, or greater than 10 cm.
72. The scaffold of any of paragraphs 47-71, wherein the bulk of the solid-state silk matrix further comprises a cell, while no cell is present in the hollow conduits.
73. The scaffold of any of paragraphs 47-71, wherein at least one hollow conduit further comprises a cell, while no cell is present in the bulk of the solid-state silk matrix.
74. The scaffold of any of paragraphs 47-71, wherein the bulk of the solid-state silk matrix comprises a first cell, and at least one hollow conduit comprises a second cell.
75. The scaffold of paragraph 74, wherein the first cell has the same cell type as the second cell.
76. The scaffold of paragraph 74, wherein the first cell has a different cell type from the second cell.
77. The scaffold of paragraph 73 or 74, wherein more than one hollow conduits comprise a cell.
78. The scaffold of paragraph 77, wherein the cell present in a first hollow conduit has the same cell type as that of the cell present in a second hollow conduit.
79. The scaffold of paragraph 77, wherein the cell present in a first hollow conduit has a different cell type different from that of the cell present in a second hollow conduit.
80. The scaffold of any of paragraphs 46-79, wherein the scaffold is implantable.
81. A method of vascularizing an engineered tissue construct comprising:
    a. providing a silk-based scaffold of any of paragraphs 46-79, wherein a coating layer comprising an endothelialization-inducing agent forms the inner surface of at least one hollow conduit;
    b. forming a layer of endothelial cells on the inner surface of said at least one hollow conduit, thereby pre-vascularizing the silk-based scaffold.
82. The method of paragraph 81, wherein the endothelialization-inducing agent comprises collagen type I, laminin, VEGF, PDGF, or any combination thereof
83. The method of paragraph 81 or 82, further comprising seeding a population of the endothelial cells into said at least one hollow conduit.
84. The method of any of paragraphs 81-83, wherein the coating layer is porous.
85. The method of any of paragraphs 81-83, further comprising filling at least a portion of the pores in the bulk of the solid-state silk matrix and/or in the coating layer, prior to the seeding of the endothelial cells in the hollow conduit, thereby enhancing the localization of the endothelial cells in the hollow conduit.
86. The method of paragraph 85, wherein said at least a portion of the pores in the bulk of the solid-state silk matrix and/or in the coating layer is filled with a gel.
87. The method of paragraph 86, wherein the gel comprises an extracellular matrix.
88. The method of any of paragraphs 81-87, further comprising seeding a non-endothelial cell in the bulk of the solid-state silk matrix.

Definitions Of Some Selected Terms

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not. Additionally, the term "comprising" or "comprises" includes "consisting essentially of" and "consisting of."

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "statistically significant" or "significantly" refers to statistical significance and generally means a two standard deviation (2SD) above or below a reference level. The term refers to statistical evidence that there is a difference. It is defined as the probability of making a decision to reject the null hypothesis when the null hypothesis is actually true. The decision is often made using the p-value.

As used herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

By the term "insoluble" is generally meant a silk composition (e.g., a silk coating layer or a solid-state silk matrix) completely or partially insoluble under a specified condition. Generally, solubility of a substance depends on properties and/or compositions of solvents (e.g., aqueous vs. non-aqueous solvents, and/or intermolecular interaction of the substance with a solvent), temperatures, pressures, or any combinations thereof. For example, a silk composition (e.g., a silk coating layer or a solid-state silk matrix) can have a higher solubility in one solvent than another, and/or it can have a higher solubility in a solvent at a higher temperature than at a lower temperature in the same solvent. In some embodiments, a silk composition (e.g., a silk coating layer or a solid-state silk matrix) can be completely or partially insoluble in an aqueous solution at a certain temperature, e.g., ranging from above 0° C. to about room temperature or from about room temperature to about body temperature of a subject (e.g., about 37° C. for a normal healthy human being, or higher or lower for other animals). An aqueous solution to which a silk composition (e.g., a silk coating layer or a solid-state silk matrix) is exposed can include any fluid that comprises water, including, but not limited to, water, blood, interstitial fluid and any other body fluid.

The term "partially insoluble" as used herein refers to a silk composition (e.g., a silk coating layer or a solid-state silk matrix) having a solubility with respect to a specified condition (e.g., an aqueous solution such as water or a buffered solution at room temperature) of less than 60%, less than 50%, less than 40%, less than 30%, less than 20%, less than 10%, less than 5% or lower. In some embodiments, the silk composition (e.g., a silk coating layer or a solid-state silk matrix) can have a solubility of less than 30% in an aqueous solution such as water or a buffered solution at room temperature. In some embodiments, when the silk composition (e.g., a silk coating layer or a solid-state silk matrix) is present in vivo, the silk composition (e.g., a silk coating layer or a solid-state silk matrix) in contact with a body fluid and/or tissue can have a solubility of less than 60%, less than 50%, less than 40%, less than 30%, less than 20%, less than 10%, less than 5% or lower. As used herein, solubility expressed in percentages refers to the maximum amount of a substance that can be dissolved in ~100 g solvent to form a homogenous solution. For example, a silk composition (e.g., a silk coating layer or a solid-state silk matrix) having a water solubility of 30% means that a maximum amount of 30 g of a silk composition can be dissolved in 100 g of water to form a homogenous solution.

As used herein, a "subject" generally means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. In addition, the methods and compositions described herein can be used to treat domesticated animals and/or pets.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polymers (polynucleotides) or oligomers (oligonucleotides) of nucleotide or nucleoside monomers consisting of naturally occurring bases, sugars and intersugar linkages. The term "nucleic acid" also includes polymers or oligomers comprising non-naturally occurring monomers, or portions thereof, which function similarly. Exemplary nucleic acids include, but are not limited to, deoxyribonucleic acid (DNA), ribonucleic acid (RNA), locked nucleic acid (LNA), peptide nucleic acids (PNA), and polymers thereof in either single- or double-stranded form. Locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo conformation. LNA nucleotides can be mixed with DNA or RNA residues in the oligonucleotide whenever desired. Such LNA oligomers are generally synthesized chemically. Peptide nucleic acid (PNA) is an artificially synthesized polymer similar to DNA or RNA. DNA and RNA have a deoxyribose and ribose sugar backbone, respectively, whereas PNA's backbone is composed of repeating N-(2-aminoethyl)-glycine units linked by peptide bonds. PNA is generally synthesized chemically. Unless specifically limited, the term "nucleic acids" encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the FAT polypeptide further comprises a polypeptide linker between the VH and VL domains which enables the scFy to form the desired structure for antigen binding. (Pluckthun, The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "cells" used herein generally refers to any cell, prokaryotic or eukaryotic, including plant, yeast, worm, insect and mammalian. Mammalian cells include, without limitation; primate, human and a cell from any animal of interest, including without limitation; mouse, hamster, rabbit, dog, cat, domestic animals, such as equine, bovine, murine, ovine, canine, feline, etc.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

The term "antibiotics" as used herein can encompass any pharmaceutically acceptable compound that can inhibit the growth of or destroy bacteria and/or other microbes, regardless of whether the compound is produced in a microorganism or produced synthetically. The term "antibiotics" can encompass disinfectants, antiseptics, and any other antimicrobial compounds. For example, the term "antibiotic" can encompass penicillin and all its derivatives. Exemplary antibiotics include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents can also be antimicrobial peptides such as defensins, magainin and nisin; or lytic bacteriophage. The antibiotic agents can also be the combinations of any of the agents listed above. See also PCT/US2010/026190.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

As used herein, the term "hormones" generally refers to naturally or non-naturally occurring hormones, analogues and mimics thereof. In certain embodiments, the term "hormones" refers to any hormones used in therapeutic treatment, e.g., growth hormone treatment. As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or variant produced by means of recombinant DNA technology, including somatrem, somatotropin, and somatropin. In one embodiment, hormones include insulin.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Exemplary Materials and Methods for Fabrication and Characterization of a Silk-based Scaffold Described Herein Silk Fibroin Solution Preparation. Five grams of *Bombyx mori* silk worm cocoons were degummed in 1 L of boiling ~0.02 M sodium carbonate for ~20-30 minutes to remove the sericin glue from the fiber. The degummed fibers were dissolved in a ~9.3 M lithium bromide solution (20% w/v) at ~60° C. for about 4 hours. The dissolved silk fibroin solution was then dialyzed against ~4 L of ultrapure water in dialysis cassettes with a 3,500 molecular weight (MW) cutoff Water was changed three times per day for about three days. The concentration of the final silk solution (6-8% w/v) was determined, e.g., by drying a known volume of the silk solution and weighing the remaining solids.

Linear Wire Array (LWA) Fabrication. LWAs were fabricated as an example of an array of elongated structures for use in fabrication of a silk-based scaffold described herein. For example, LWAs were fabricated by cutting an array of circular holes (e.g., ⌊=~154 μm-~787 μm) into acrylic or corrugated cardboard sheets using a laser cutter. The hole wall-to-wall spacing ranged, for example, between 500 um and 1 mm. Polytetrafluoroethylene (PTFE)-coated stainless steel wires with diameters matched to the size of circular holes (e.g., ranging from ~154 μm to ~787 μm) (McMaster Can, Chicago, Ill.) were cut into about 20 mm or about 40 mm pieces, arranged vertically into the holes and secured, e.g., by casting polydimethyl siloxane (PDMS) (Dow Corning Corporation, Midland, Mich.) around the base of the wires. Once the PDMS was cured, wire arrays were trimmed to the appropriate size to fit into a mold for building a silk-based scaffold having a solid-state silk matrix formed around the LWA.

Silk-Based Scaffold Assembly. Silk fibroin solutions were diluted to ~5-6% w/v and poured into molds containing an array of elongated structures, e.g., the wire arrays as described above. To create silk-based scaffolds with randomly aligned pores in the bulk of the silk fibroin matrix, arrays of elongated structures, e.g., 15 mm diameter arrays were placed into the bottom of polystyrene containers (Ø=~15 mm; h=~20 mm). One milliliter of silk solution was poured into the mold and isotropically frozen at either −20° C. or −80° C. for 12 hours. For silk-based scaffolds with parallel pores in the bulk of the silk fibroin matrix, a wire array strip (e.g., 40 mm×40 mm×15 mm) was secured in a custom built PDMS mold, e.g., as shown in FIG. 6A. This mold consisted of two chambers separated by a metal plate. One chamber contained the silk solution, while the other chamber contained a freezing agent. As the freezing agent was applied to one side of the metal plate, the silk solution was frozen in a single direction (i.e. directional freezing) resulting in parallel pores (for schematic representation of this process, please refer to FIG. 6A). Different freezing agents were utilized in this system to achieve different freezing rates, e.g., liquid nitrogen (fast freezing rate), absolute ethanol and dry ice bath (medium freezing rate), and 70% v/v ethanol and dry ice bath (slow freezing rate). Frozen samples were lyophilized for about 12-48 hours and water annealed for about 12 hours at ~25° C. to induce β-sheet formation, thereby rendering the scaffolds insoluble in aqueous environments. Separation of the array of elongated structures from the solid-state silk fibroin forms hollow conduits in the solid-state silk fibroin.

Silk Coating Layer Formation or Silk Tube Assembly. Concentrated silk fibroin solution was obtained, for example, by dialyzing ~15 ml of ~6-8% w/v silk solution against 1 L of ~10% w/v polyethylene glycol solution (10,000 MW) in dialysis cassettes with a 3,500 MW cutoff for ~21 h at room temperature. The resulting concentrated solution (20% w/w) was poured into, e.g., a 2 mL cylindrical container, for wire array dipping. To make silk coating layers on the wire array (such that tubular structures are formed after removal of the wire array, e.g., silk tubes), an array of elongated structures, e.g., LWAs, was dipped in the silk solution, dried at ~60° C. for ~30 minutes and water annealed for about six hours. Silk coating layers with different wall thicknesses can be obtained by repeating these steps multiple times. In some embodiments, the silk coating layers were porous. Porous silk coating layers were obtained, e.g., by incorporating water-soluble porogens (e.g., ~0.05% w/v polyethylene oxide (PEO) (10,000 MW)) in the concentrated silk solution. The water-soluble porogens (e.g., PEO) was subsequently leached out in ultrapure water resulting in porous silk coating layers. Silk coating layers were also functionalized with at least one active agent (e.g., a range of fluorescent dyes and bioactive agents) by incorporating the active agent, for example, but not limited to, 75 μg/ml dextran-conjugated fluorescein or rhodamine (Invitrogen, Carlsbad, Calif.), 2.5 μg/ml bovine collagen-I (BD Biosciences, San Jose, Calif.), 0.25 μg/ml human laminin (Sigma Aldrich, St. Louis, Mo.), 500 μg/ml horseradish peroxidase (HRP) (Sigma Aldrich, St Louis, Mo.) or 0.5 μg/ml vascular endothelial growth factor (VEGF) (Invitrogen, Merelbeke, Oost-Vlaanderen, Belgium), into the silk solution during the silk coating casting process. All solutions of water-soluble porogens (e.g., PEO), and active agents (e.g., dyes and bioactive agents) were prepared such that the maximum volume added to the silk solution was ~50 μl or less to prevent excessive dilution of the silk solution. The elongated structures (e.g., LWAs) with deposition of the silk coating layers on their surfaces were subsequently dried, water annealed and placed into molds for scaffold assembly as described above.

Scanning Electron Microscopy (SEM). In order to maintain sample structure in the dry state, silk-based scaffolds were frozen at −80° C. and lyophilized for 12 hours prior to imaging. Dried samples were sputter coated with platinum/palladium (40 mA, 60 seconds) and imaged with a field emission SEM and 5 keV electron beam (Supra55VP, Zeiss, Oberkochen, Germany).

Pore Size and Porosity Determination. Scaffold pore size distribution, porosity and pore surface area were determined, e.g., using Mercury Intrusion Porosimetry (MIP), Confocal Laser Scanning Microscopy (CLSM), or any art-recognized methods.

To determine pore size and porosity by MIP, dried samples (Ø=~9.0 mm, height=~10 mm) were analyzed, e.g., using a PoreMaster 33 porosimeter (Quantachrome Instruments, Boynton Beach, Fla.). PoreMaster (Quantachrome) was used for all data collection and analysis. Average pore size and porosity were collected from one scaffold. To determine porosity, the density of the silk scaffold was assumed to be 1.3 g/cm$^3$ based on the previous reports (Minoura, 1990).

To determine pore size and porosity by CLSM, silk scaffolds were stained with 0.33 µM rhodamine/phalloidin (Invitrogen, Merelbeke, Oost-Vlaanderen, Belgium) as silk readily takes up rhodamine dye. Scaffold cross-sections hydrated in phosphate buffer saline solution (PBS) were imaged using a confocal laser scanning microscope (TCS SP2 scanner, DMIRE2 CLSM, Leica, Wetzlar, Germany) equipped with 488 nm argon and 543 He/Ne lasers. Samples were excited with a 488 nm laser and visualized using a 504-655 nm bandpass which incorporates rhodamine fluorescence as well as intrinsic autofluorescence of silk. The length and width of pore cross-sections were measured (10 pores per image over a total of 5 images per sample) using Image J (National Institutes of Health, Bethesda, Md.).

Compression Testing. Compressive mechanical properties of hydrated scaffold samples (Ø=6.0 mm, height=3 mm) were obtained using an Instron 3366 (Norwood, Mass.) testing frame equipped with a 10 N load cell. The tests were carried out in 0.1 M PBS at 37° C. at a strain rate of 5 mm/min. The sample modulus and yield strength were determined from the stress-strain curve normalized to the cross-sectional area of the scaffold using a Labview program, e.g., written as previously described (Gil, 2011). Briefly, the compression modulus was defined as the slope of the linear region between 2% and 9% strain. Compressive yield strength was defined as the stress at the intersection of the stress-strain curve and a line parallel to the linear region, offset by ~0.5% strain.

Horseradish Peroxidase (HRP) activity assay. To determine the activity of bioactive agents used to functionalize silk tubes, the activity of HRP enzyme was utilized. Silk coating layers were functionalized with HRP as a model active agent. A common HRP substrate, 3,3'-diaminobenzidine was applied to the scaffolds directly or to scaffold cryosections and the formation of a brown product was monitored indicating the presence of active HRP.

Cell Culture. All reagents were purchased from Invitrogen (Merelbeke, Oost-Vlaanderen, Belgium) unless stated otherwise. Human mesenchymal stem cells (hMSCs) were isolated from fresh bone marrow aspirate (Lonza, Basel, Switzerland) as known in the art, e.g., the method described in Altman, 2002, with modifications. For example, bone marrow aspirate was diluted in PBS and cultured at 37° C. in 5% $CO_2$ for about 10 days. Expansion medium (Dulbecco's modified Eagle medium supplemented with 10% fetal bovine serum, 100 U/ml penicillin, 100 µg/ml streptomycin, 0.25 µg/ml amphotericin, 0.1 mM non-essential amino acids) was added twice a week but spent medium was not removed until cells reached 50% confluence. Once the cells reached above 50% confluence, non-adherent hematopoietic cells were removed through PBS washes and the hMSCs were cultured in expansion medium until either passaged or frozen. Primary human arterial endothelial cells (hAECs) (Lonza, Basel, Switzerland) were cultured in Endothelial Cell Growth Media-2 (Lonza, Basel, Switzerland) and 2% fetal bovine serum (Lonza). Cells were cultured as single cultures or co-cultures of hMSCs and hAECs. Single cultures were performed in an unconfined or confined seeding system.

To perform single cell cultures in an unconfined system, for example, hMSCs (P3-P5) were seeded on silk scaffolds (Ø=12 mm, h=3 mm) with ~508 µm diameter silk tubes (+/−collagen type I) at a cell density of $1\times10^5$ cells/scaffold in a total volume of 75 µl. Samples were incubated at 37° C. in 5% $CO_2$ for 2 hours before media was added. At days 1 post-seeding samples were processed for a DNA content assay (Invitrogen, Merelbeke, Oost-Vlaanderen, Belgium) or stained with 2 µM calcein AM (Invitrogen, Merelbeke, Oost-Vlaanderen, Belgium) for 45 min prior to CSLM imaging. Samples for CLSM were excited with a 488 nm laser and visualized using a 501-555 nm bandpass. For the DNA content assay, to better discern differences in cell numbers in silk tubes, layers of confluent cells on the top and bottom scaffold surfaces were removed prior to quantification using a biopsy punch and surgical blade.

To perform single cell cultures in a confined system, e.g., to confine cells to the hollow conduits of the silk-based scaffold, the pores of the surrounding bulk region of the silk-based scaffold (Ø=12 mm, h=3 mm) were filled with a fibrin gel (10% w/v fibrinogen mixed with 5 U/mL thrombin in a 4:1 volume ratio) prior to removal of the elongated structures (e.g., LWA). hAECs (P4-P7) were then seeded onto the scaffold at a cell density of $5\times10^5$ cells/scaffold and cultured for seven days. A cross-section through the middle of the scaffold was made and the level of conduit/tube endothelialization was assessed by CLSM following cell staining with 2 µM calcein AM for 45 minutes. Samples were visualized as described above. To quantify conduit/tube endothelialization in the presence of different endothelialization-inducing agents (e.g., collagen type I, laminin, VEGF) present in the silk coating or silk tube, an arbitrary value between 1 and 4 was assigned to 16 tubes/scaffold for a total of 3 scaffolds per treatment. No cells or only an occasional cell in the silk coating or silk tube was given a score of 1. A score of 2 indicated sporadic cell coverage, with no areas of contiguous endothelialization. A score of 3 indicated >75% endothelialization with only small areas where the cell layer was not contiguous and 4 indicated complete endothelialization with a completely contiguous layer of cells around the silk coating or silk tube.

To perform cell co-culture on silk-based scaffolds, in one embodiment, two different types of cells were compartmentalized. For example, cells were compartmentalized by physically confining hMSCs to the bulk of the silk-based scaffold and hAECs to the hollow conduits. Prior to cell seeding, hMSCs were labeled with a 0.01 mM DiD solution (Invitrogen, Merelbeke, Oost-Vlaanderen, Belgium) and hAECs were labeled with a 0.01 mM DiI solution (Invitrogen, Merelbeke, Oost-Vlaanderen, Belgium) for easier visualization of the cells upon seeding in the scaffold. hMSCs were seeded at a density of ~4×10⁵ cells/scaffold in the scaffold bulk (ø=12 mm, h=3 mm) prior to removal of the elongated structures (e.g., LWA) in the presence or absence of a fibrin gel (10% w/v fibrinogen mixed with 5 U/mL thrombin in a 4:1 volume ratio). hMSCs were cultured for ~2 days before the array of the elongated structures (e.g., LWAs) were removed. hAECs were seeded at a cell density of ~4×10⁵ cells/scaffold and cultured for about two days. A cross-section through the middle of the scaffold was made and imaged by CSLM. DiD was excited with a 633 nm laser and visualized using a 650-680 nm bandpass. DiI was excited with a 543 nm laser and visualized using a 555-585 bandpass.

DNA Content Assay. Cell proliferation was assessed based on DNA content of cells cultured on 3D scaffolds. Scaffolds were minced with microscissors in a lysis buffer consisting of 0.2% v/v Triton X-100 and 5 mM magnesium chloride. Scaffold particles were removed by centrifugation at 12,000 rpm for 10 min at 4° C. DNA in the supernatant was quantified using a PICOGREEN® assay (Invitrogen, Merelbeke, Oost-Vlaanderen, Belgium) according to manufacturer's protocol and detected on a fluorescent plate reader by exciting at 480 nm and measuring emission at 520 nm.

Statistical analysis. Data are expressed as mean±standard deviation. Statistically significant differences were determined by one- or two-way analysis of variance (ANOVA) and Bonferroni post-test. Statistical significance was accepted at $p<0.05$ and indicated in the figures as $*p<0.05$, $p<0.01$ and $*p<0.001$.

Example 2

Silk-based Scaffolds with Hollow Channels Fabricated Using Linear Wire Arrays (LWAs)

Simple, efficient and reproducible means of introducing oxygen and nutrient delivery conduits into critically-sized tissue engineered constructs can significantly advance the regenerative medicine field towards replacing complex tissue systems in the body. To address this need, efforts are focused on developing strategies for vascularizing engineered tissues to enable immediate perfusion upon implantation. One active area of research employs microfabrication techniques to build microfluidic channels into scaffold platforms that resemble physiologic microvasculature. While microfabrication is efficient and reproducible, microfabricated cell culture platforms undergo extensive handling in order to stack the scaffolds to the desired construct dimensions. Further, this microfabricated platforms cannot degrade easily, and thus is less desirable for implantation. An alternate approach for incorporating nutrient delivery conduits into tissue constructs employs methods for building linear channels that extend through the construct bulk. These methods include laser piercing (Maidof et al., 2006), sacrificial fibers (Flynn et al., 2003; Nazhat et al., 2006), and removable wire arrays (Moore et al., 2006; Bagnaninchi et al., 2007). While these methods have introduced channels into polymer scaffolds, these resulting scaffolds are not tunable for channel diameter range, channel spacing/patterning, and bulk morphological, mechanical, and biodegradation properties. Further, these previous reports do not teach all-protein silk biomaterial for use in engineering such a large tissue construct.

Presented herein is a method of introducing an array of hollow channels into silk scaffolds that is very versatile. A major advantage of this system is the high level of control over the properties of the oxygen and nutrient delivery conduits (e.g., diameter, spacing, wall thickness, bioactive compound delivery in the wall, degradation lifetime, surface chemistry and many other features) and the surrounding silk bulk, which enables the creation of 'tailor-made' scaffolds for a variety of tissue engineering purposes.

Silk-based scaffolds with hollow channels were prepared using a sequential process involving fabrication and placement of the LWA, optional wire functionalization with bioactive agents, application of the silk solution, lyophilization and β-sheet induction (FIG. 1). Upon completion of this process, LWAs are removed, leaving behind 3D, porous scaffolds with hollow channels spanning the length of the scaffold. Each step of this process allows for the properties of the final scaffold to be tuned for a particular tissue engineering purpose (FIG. 1).

In the first step of the process of placing an array of elongated structures (e.g., wire array) in a mold, scaffold size and shape, channel diameter, channel wall-to-wall spacing and channel pattern can be controlled. Scaffold size and shape can be determined by the size and shape of the freezing mold. The size of the scaffold is unlimited in the x- and y-planes. In some embodiments, the size of the scaffold can be limited to approximately 20 mm in the z-plane. Without wishing to be bound by theory, in some embodiments, scaffold dimensions greater than 20 mm in the z-plane can result in heterogeneous pore sizes because the freezing source becomes masked by the formed scaffold. Channel diameter, spacing and pattern can be a function of the wire diameter, spacing and/or arrangement, which is controlled at the LWA design stage. Wire array parameters can be designed using a CAD program, which can be easily modified and controlled, and can then be transferred to a placeholder via a laser cutter. Once built, LWAs can be reused multiple times.

The second step of the fabrication process as shown in FIG. 1 is optional, as it involves coating the walls of hollow channels with a thin, hollow silk tube. This can be achieved, for example, by dipping LWAs in a concentrated silk solution to form a thin, continuous silk tube around the wire, as has been described previously (Lovett et al, 2007). At this stage, channel wall thickness and/or porosity can be controlled and silk tubes can be functionalized with a range of bioactive agents.

Step three of the fabrication process as shown in FIG. 1 can involve application of the silk solution around the LWA to create the silk-based scaffold. Silk solution can at this stage be functionalized, for example, with a number of different bioactive agents to specifically control cell interactions with the scaffold bulk. Silk-based scaffolds have previously been functionalized with a range of bioactive molecules, including collagen (Lu et al, 2011), gelatin (Lu et al, 2010), chitosan (She at al, 2008) and hyaluronic acid (Garcia-Fuentes, 2008). Pore size, mechanical properties and degradation rate can be altered at this stage by changing the properties of the silk solution, including, but not limited to, the molecular weight of silk fibroin (Wray et al, 2006) and silk solution concentration (Lu and Feng, 2006).

Step four of the fabrication process as shown in FIG. 1 can involve formation of a 3D solid-state silk fibroin matrix (e.g., a 3D silk sponge) around the LWA, e.g., by freezing and lyophilization of the silk solution. Without wishing to be bound by theory, the freezing rate (Lu and Feng, 2006) and freezing orientation can affect pore size (demonstrated in Example 4), shape and/or orientation, which in turn affect mechanical and degradation properties of the scaffold.

At step five as shown in FIG. 1, β-sheet formation can be induced by immersion in methanol or water annealing. The effect of β-sheet content on silk degradation rate and mechanical properties has been previously described (Hu et al, 2011).

Example 3

Figures 2A, 2B, 2C:
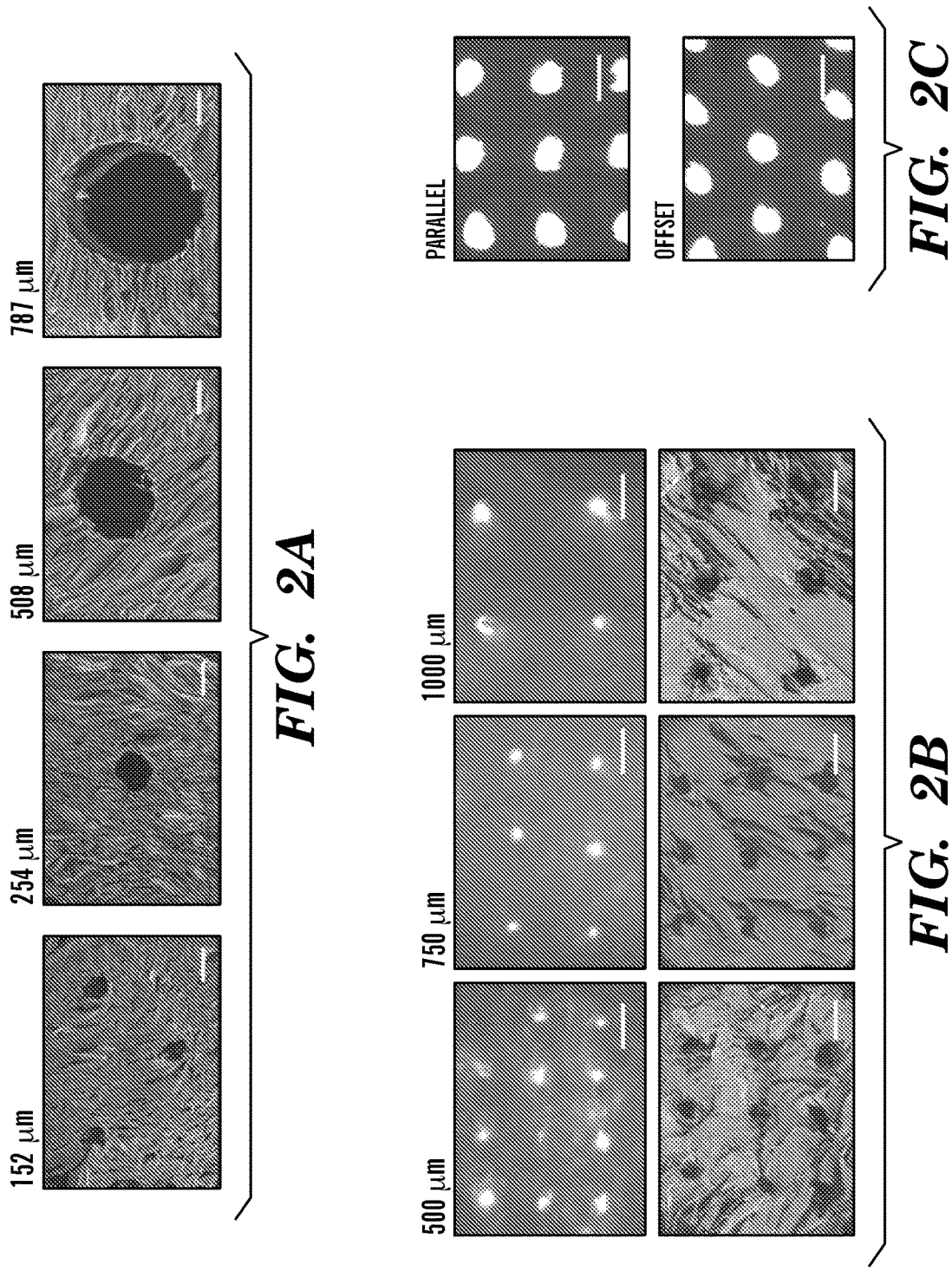
FIGS. 2A-2C are SEM and light microscopy images of hollow channel diameter, spacing and patterning properties.

Configuration, Morphology and Functionalization of Hollow Conduits (e.g., Channels) within a Silk-based Scaffold A number of channel configurations were engineered into silk-based scaffolds using different LWAs with a range of wire diameters, wire wall-to-wall spacing and wire arrangements. Channels ranging from 154 μm to 787 μm in diameter were introduced into silk scaffolds (FIG. 2A). Each channel was hollow and the channel periphery displayed open porosity similar to that of the scaffold bulk. Channels were positioned with 500 μm, 750 μm or 1000 μm wall-to-wall spacing in either parallel or offset arrangement (FIGS. 2B-2C).

Figure 3D:
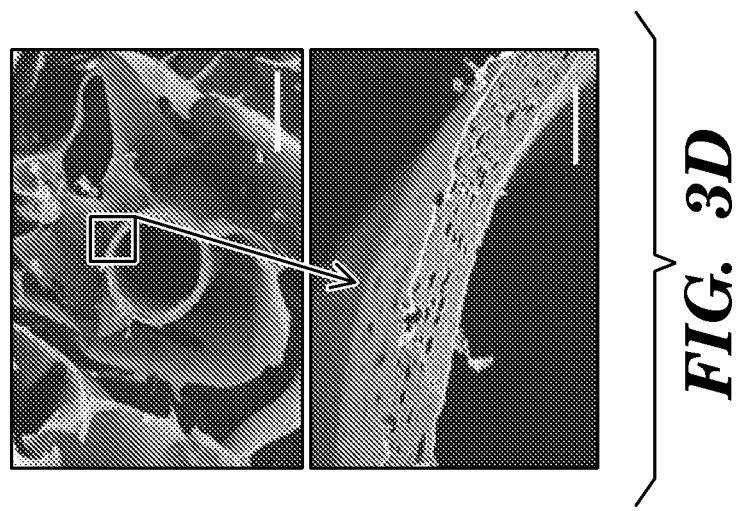
Figure 3C:
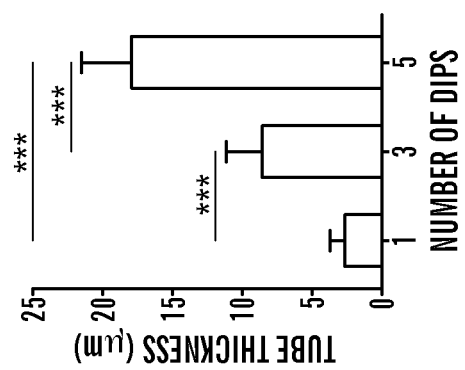

In some embodiments, silk tubes were introduced into the channel periphery, e.g., by dipping LWAs in a concentrated silk solution (FIG. 3A). Silk formed a thin coating on the wire array that when dried and water annealed formed a continuous, thin silk tube that was insoluble in aqueous environments. By repeating this process multiple times, silk tubes of different wall thicknesses were formed. In some embodiments, silk tube walls were smooth and continuous with no inherent porosity (FIG. 3B). One dip resulted in tubes with 2 μm±1 μm wall thickness, 3 dips resulted in 9 μm±3 μm wall thickness and 5 dips resulted in 18 μm±4 μm wall thickness (FIG. 3C). In alternative embodiments, porosity was engineered into silk tube walls by leaching out high molecular weight (10,000) PEO in water following scaffold building and water annealing steps. This process resulted in pores of about 2-10 μm in diameter (FIG. 3D).

Figure 4B:
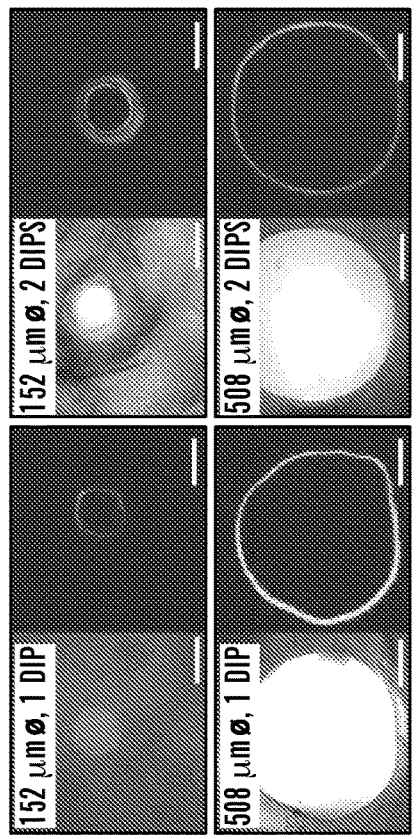
FIGS. 4A-4E shows the results of silk tube functionalization.
Figure 4A:
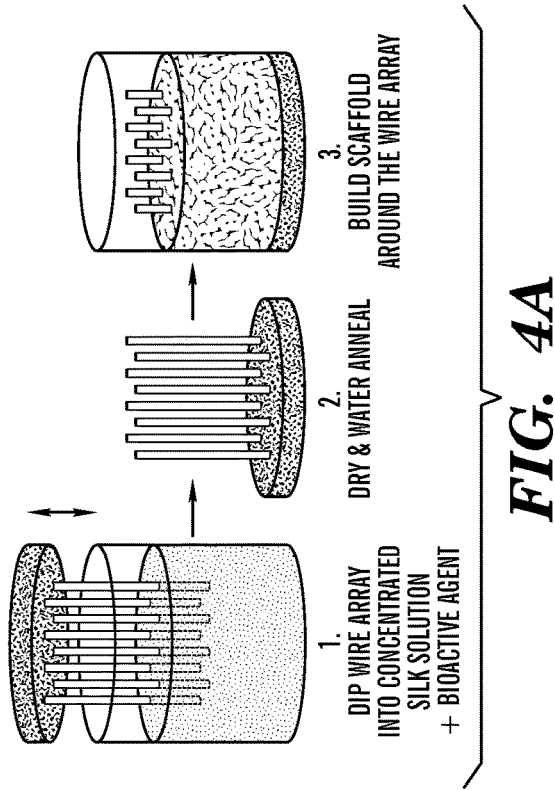

In some embodiments, silk tubes can be functionalized with at least one active agent. For example, silk tubes were successfully functionalized with dextran conjugated to fluorescein or rhodamine, HRP enzyme and collagen-I. Functionalization agents were introduced into the concentrated silk at high concentrations, but small volumes in order to reduce unnecessary dilution of the silk solution. Functionalized tubes were formed in a similar manner to silk tubes with no functionalization agent (FIG. 4A). When the LWA was dipped once in a dextran-fluorescein functionalized silk solution, a contiguous fluorescent tube was observed using both 154 μm and 508 μm wires (FIG. 4B). When this process was repeated twice, with the first dip in dextran-fluorescein functionalized silk and the second dip in dextran-rhodamine functionalized silk, a tube with two distinct bands of florescence was observed. The inner band displayed fluorescence in the green range consistent with fluorescein, while the outer tube displayed florescence in the red range consistent with rhodamine. There was no significant mixing of the two dyes, indicating that the silk stabilized the dyes within the layer into which they were introduced (FIG. 4B). Functionalization with fluorescent dyes served as proof of principle that bioactive agents can be introduced into silk tubes.

Figure 4E:
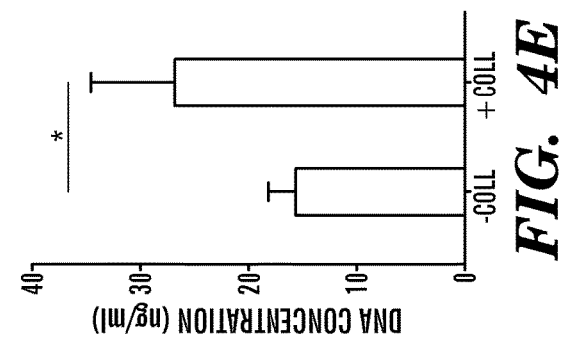
Figure 4D:
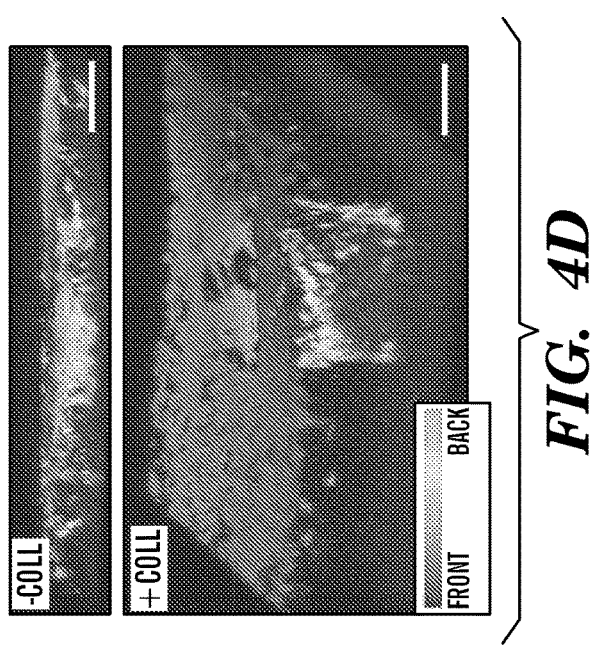
Figure 4C:
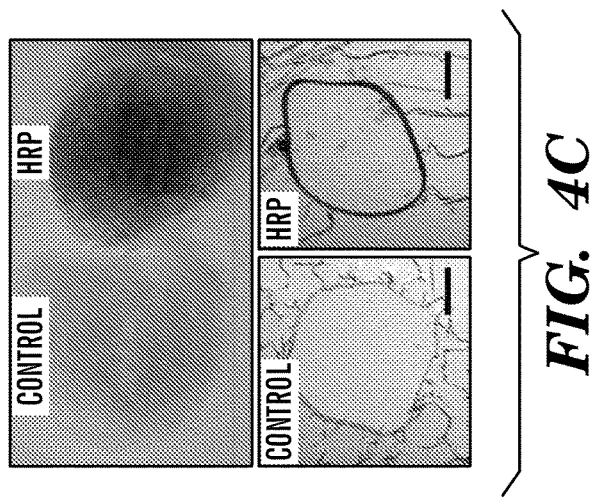

To ensure that the bioactive agents introduced into silk tubes remain functionally active, HRP enzyme was introduced into silk tubes. Once the scaffold was built around the tubes, DAB was added on the scaffold to probe HRP activity. Brown precipitate indicating DAB conversion to its oxidized form indicated functional HRP (FIG. 4C). Brown staining was considerably more prominent around the tubes, compared to the rest of the scaffold. However, in some embodiments, brown precipitate was observed in the scaffold bulk. To investigate whether the presence of brown precipitate in the scaffold bulk is the result of DAB precipitate diffusing out from the silk tubes rather than HRP present in the scaffold bulk, cryosections of the scaffold were prepared and DAB was added directly onto the section and the reaction was observed under the microscope. In this case, DAB conversion to its brown oxidized form was clearly confined to silk tubes and was not present in the scaffold bulk (FIG. 4C), indicating that the brown precipitate observed in the scaffold bulk was due to diffusion of DAB precipitates out from the silk tubes.

To determine if the bioactive agents introduced into silk tubes could be recognized by cells, silk tubes were loaded with collagen-I and cultured with hMSCs. Silk-collagen blend scaffolds have been previously shown to improve cellular attachment and proliferation over silk scaffolds alone (Lu et al., 2011). A similar result with the collagen-I loaded silk tubes would indicate that functionalized silk tubes could modulate cell behavior in this platform. After 14 days post-seeding, CSLM revealed that collagen-I samples encouraged hMSCs proliferation deeper into the scaffold bulk compared to the unfunctionalized samples (FIG. 4D). Moreover, the DNA content assay revealed that the collagen-I samples supported significantly higher hMSC attachment at 24 hours post-seeding (FIG. 4E).

Example 4

Physical and Mechanical Properties of the Bulk Region of a Silk-based Scaffold

In addition to the range of tunable morphological and functionalization properties of the hollow conduits (e.g., channels), physical and mechanical properties of the scaffold bulk can also be altered. For example, the level of control over the scaffold pore size, shape and orientation, which are known to affect cellular function and resulting tissue formation, can be altered. Different tissue engineering applications can also have vastly different requirements with regard to these properties (Mikos et al, 2006).

Size, shape and/or orientation of the pores in the bulk region of the silk-based scaffold were a function of, e.g., but not limited to, the freezing process. Without wishing to be bound by theory, the ice crystals that formed in the silk solution acted as porogens and dictated the features of the pores once the scaffold was lyophilized. Pore shape and orientation were controlled in part, e.g., by the freezing direction. When the silk solution was isotropically frozen at either −20° C. or −80° C., the pores were relatively round and randomly oriented (FIG. 5A). According to MIP, samples frozen at −80° C. had median pore diameter of 28 μm and an interquartile range (IQR) of 22 μm to 31 μm. Median pore diameter when frozen at −20° C. was higher at 72 μm with an interquartile range (IQR) of 48 μm to 93 μm (FIG. 5B). The average porosity was similar for the two scaffolds with 87.2% porosity for scaffolds frozen at −20° C. and 81.8% porosity when frozen at −80° C. (FIG. 5C).

Figures 6D, 6E:
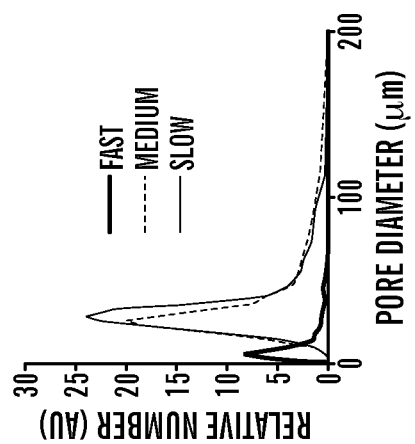
Figure 6F:
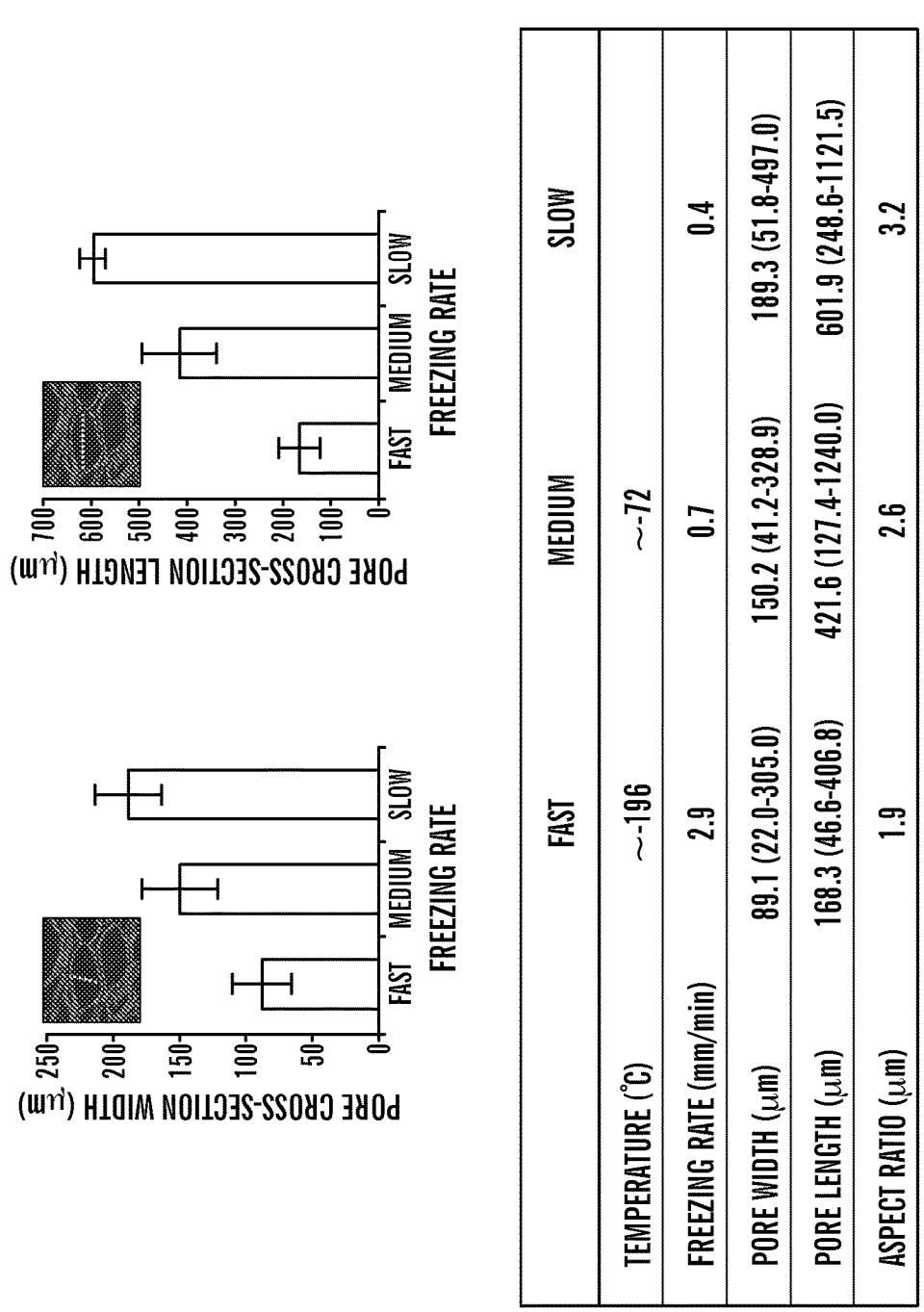

Alternatively, silk solution frozen in a custom designed PDMS mold (FIG. 6A), in which the freezing process proceeded in a single direction only, contained pores that had an elongated shape and were aligned parallel to one another and orthogonal to the metal plate (FIG. 6B). Without wishing to be bound by theory, scaffolds frozen at higher temperatures generally freeze at slower rates and therefore result in larger ice crystals and in turn larger pores. Three different freezing agents were employed to freeze scaffolds in the directional freezing setup to achieve three different freezing rates referred to as 'fast', 'medium' and 'slow'. The silk freezing front proceeded at 2.9 mm per minute in the 'fast' freezing rate, 0.7 mm per minute in the 'medium' freezing rate and at 0.4 mm per minute in the 'slow' freezing rate. The pores of the resultant scaffolds reflected the differences in the freezing rate, with pores size increasing with decreased freezing rate (FIG. 6C). MIP was initially used to determine the pore size of these scaffolds (FIG. 6D), but it was apparent that the values were underestimated compared to pore sizes observed in SEM images. This is likely the result of inherent properties of the MIP technique, where the measurements assume perfectly cylindrical pores and cannot account for pores with irregular shapes. Pore sizes formed by directional freezing were therefore determined from images of hydrated scaffold cross-sections visualized by confocal microscopy (FIG. 6F insets). Due to the irregular shape of the pores, both the width and the length of each pore cross-section were noted. Both parameters increased with decreased freezing rate, such that scaffolds frozen at the slowest rate displayed largest pores. Pore cross-section width was 89.1±22.5 µm (22.0 µm-305.0 µm) at 'fast' freezing rate, 150.2±28.8 µm (41.2 µm-328.9 µm) at 'medium' freezing rate and 189.3±25.1 µm (51.8 µm-497.0 µm) at 'slow' freezing rate. Pore cross-section length was 168.3±42.9 µm (46.6 µm-406.8 µm) at 'fast' freezing rate, 421.6±81.1 µm (127.4 µm-1240.0 µm) at 'medium' freezing rate and 601.9±27.0 µm (248.6 µm-1121.5 µm) at 'slow' freezing rate (FIG. 6F). Scaffold porosity was high for all three freezing rates, with 78.8% for the 'fast' freezing rate, 86.1% for 'medium' freezing rate and 87.1% for 'slow' freezing rate (FIG. 6E).

Figures 7A, 7B:
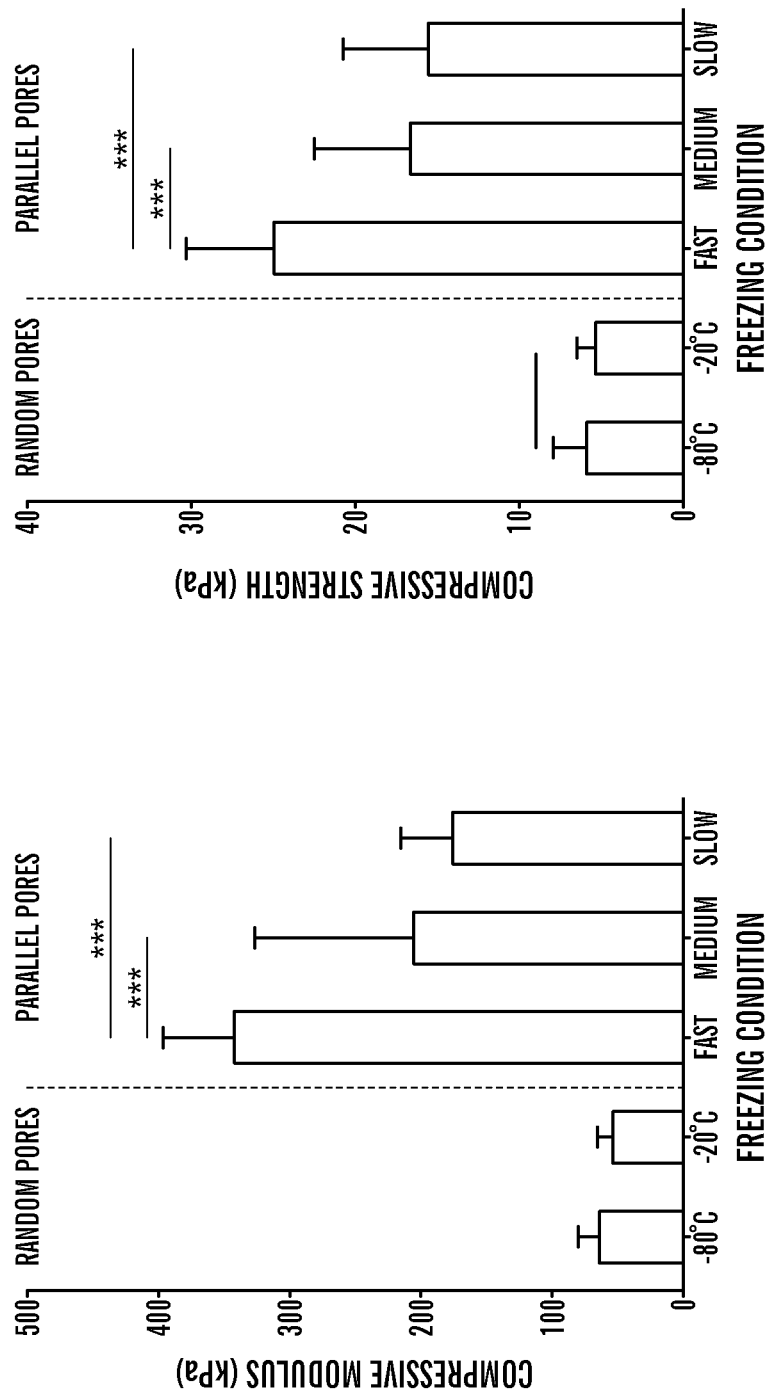
FIGS. 7A-7B are bar graphs showing mechanical property data of hydrated scaffold bulk with random and parallel pores produced by different freezing temperatures and/or rates. The mechanical properties were determined by compressive loading of the hydrated scaffold bulk with random and parallel pores.

Compressive properties of the silk scaffold bulk differed significantly, partly depending on, e.g., the pore morphology and/or orientation. Scaffolds with randomly oriented pores consistently displayed significantly lower ($p<0.001$) compressive modulus (FIG. 7A) and compressive strength (FIG. 7B) compared to scaffolds with parallel pores, indicating that these scaffolds were less mechanically strong, but were more elastic than scaffolds with parallel pores. A downward projecting trend in compressive modulus and strength was observed with decreased freezing rate in scaffolds with directional pores.

In some embodiments, silk particles (including silk microfibers or nanofibers) can be added into a silk solution as a way to improve the mechanical properties (Mandal et al., "High-strength silk protein scaffolds for bone repair" PNAS (May 2012), the content of which is incorporated herein by reference).

Example 5

Cell Interactions with Hollow Conduits (e.g., Channels) and Silk Tubes in a Silk-based Scaffold One of the main advantages of introducing hollow conduits (e.g., channels) into 3D scaffolds is the ability to endothelialize those channels and therefore pre-vascularize the scaffold. Scaffold pre-vascularization has been shown to aid construct integration with the host tissue (Levenberg et al., 2005; Rouwkema et al., 2006; Lesman et al., 2009). Human arterial vascular cells (hAECs) were therefore introduced into the hollow channels with different morphologies, including hollow channels with open wall porosity, silk tubes and porous silk tubes (FIG. 8A). Cells were seeded on the scaffolds in a 'confined' seeding system, e.g., as described in Example 1, where the pores of the scaffold bulk were filled with fibrin gel to better direct hAECs to the hollow channels. Hollow channels with open porosity were found to support hAEC attachment and spreading where the cells formed a nearly contiguous layer around the channel wall by day seven post-seeding. Cells were able to span the entire channel, as the imaging was done in the middle of the channel length. Porous and non-porous silk tubes did not support hAEC attachment, as very few cells were observed on either tube configuration (FIG. 8B). Without wishing to be bound by theory, lack of hAEC attachment to silk tubes can be due to the smooth surface encountered by the cells, which are known to preferentially interact with surfaces that have high porosity (Marois et al., 1999).

Figure 9A:
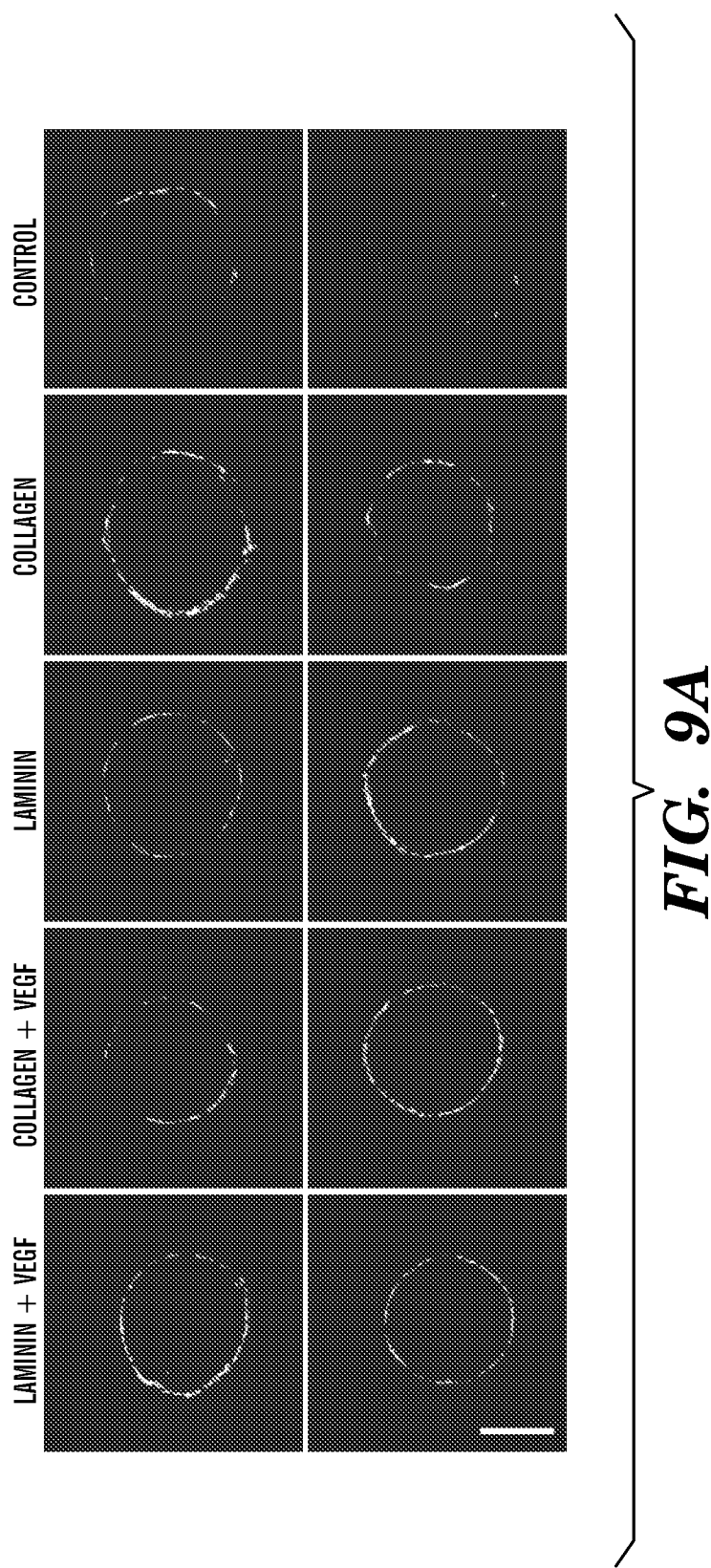
FIGS. 9A-9B show experimental data of hAEC interaction with functionalized silk tubes present in a silk-based scaffold.
Figure 9B:
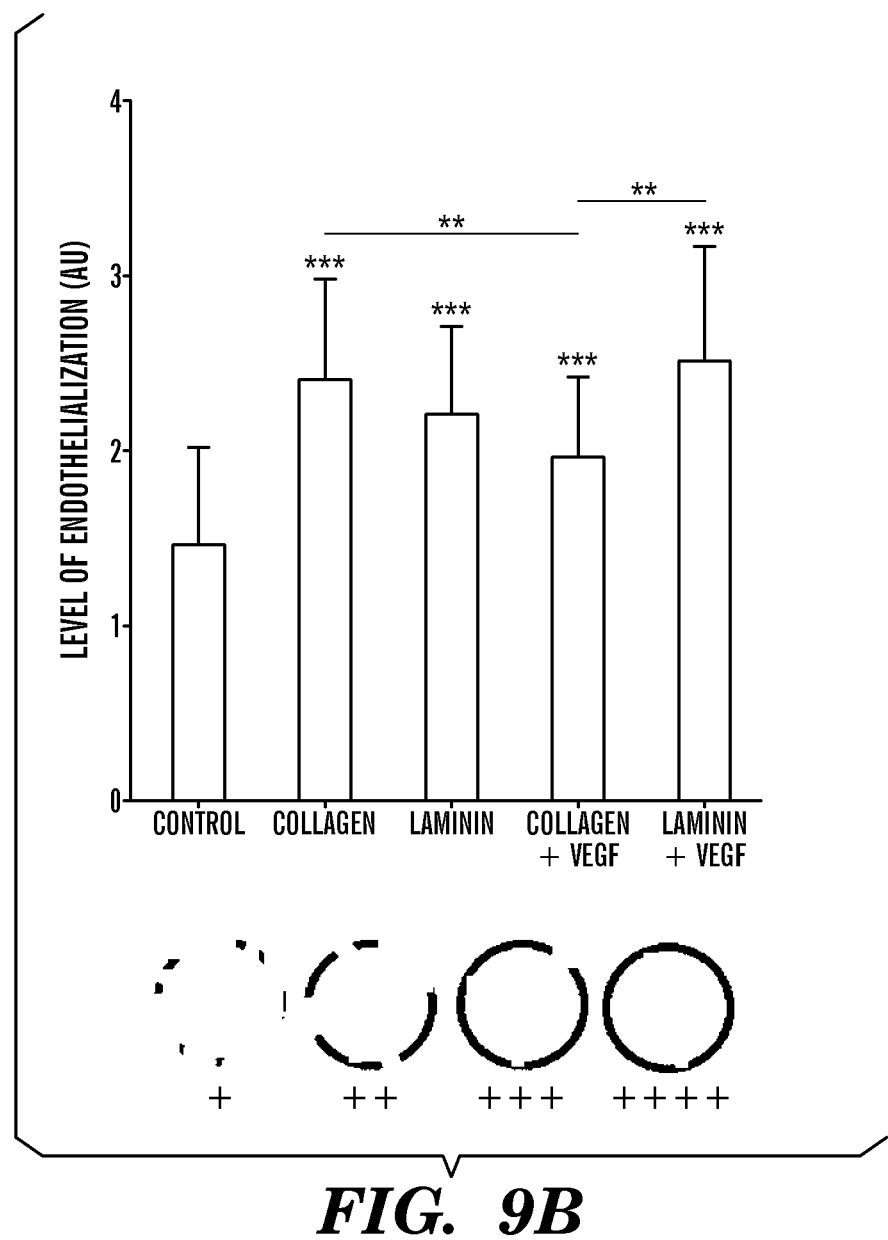

The lack of hAECs growth on silk tubes was overcome, e.g., by introducing bioactive agents into the silk tubes during the silk tube casting process (e.g., LWA dipping process). The level of cell endothelialization was visualized by staining cells with calcein AM (FIG. 9A) and quantified by scoring the degree of cell layer contiguity around the silk tube in multiple tubes (FIG. 9B). The presence of laminin and collagen significantly improved silk tube endothelialization. hAECs formed nearly contiguous cell layers around the silk tubes when collagen and/or laminin, which are known to support endothelial cell attachment and proliferation (Unger et al., 2004, Yamaguchi et al., 2011), were present. However, there was no significant difference in the level of endothelialization between these two bioactive agents, even though laminin concentration in the silk tubes was 10-fold lower than collagen. The concentrations and/or combination of these matrix proteins in the silk tube can be adjusted to optimize silk tube endothelialization. In some embodiments, VEGF was also introduced into silk tubes in the presence of collagen or laminin, but did not significantly improve silk tube endothelialization compared to those agents alone. However, significantly higher tube endothelialization was observed on laminin+VEGF compared to collagen+VEGF samples. Without wishing to be bound by theory, the presence of VEGF can have other advantages in this system, including protection of cells from apoptosis (Fujito et al, 1999; Gerber et al, 1998; Gerber, 1998) and stimulation of angiogenesis in vivo (Ashara et al, 1995; Bauters, 1995; Banal et al, 1994). Furthermore, in some embodiments, silk tubes can be functionalized with a combination of VEGF and platelet derived growth factor (PDGF), e.g., to promote vessel sprouting and capillary stabilization.

Example 6

Cell Compartmentalization Using an Array of Elongated Structures, e.g., LWAs

Figure 10A:
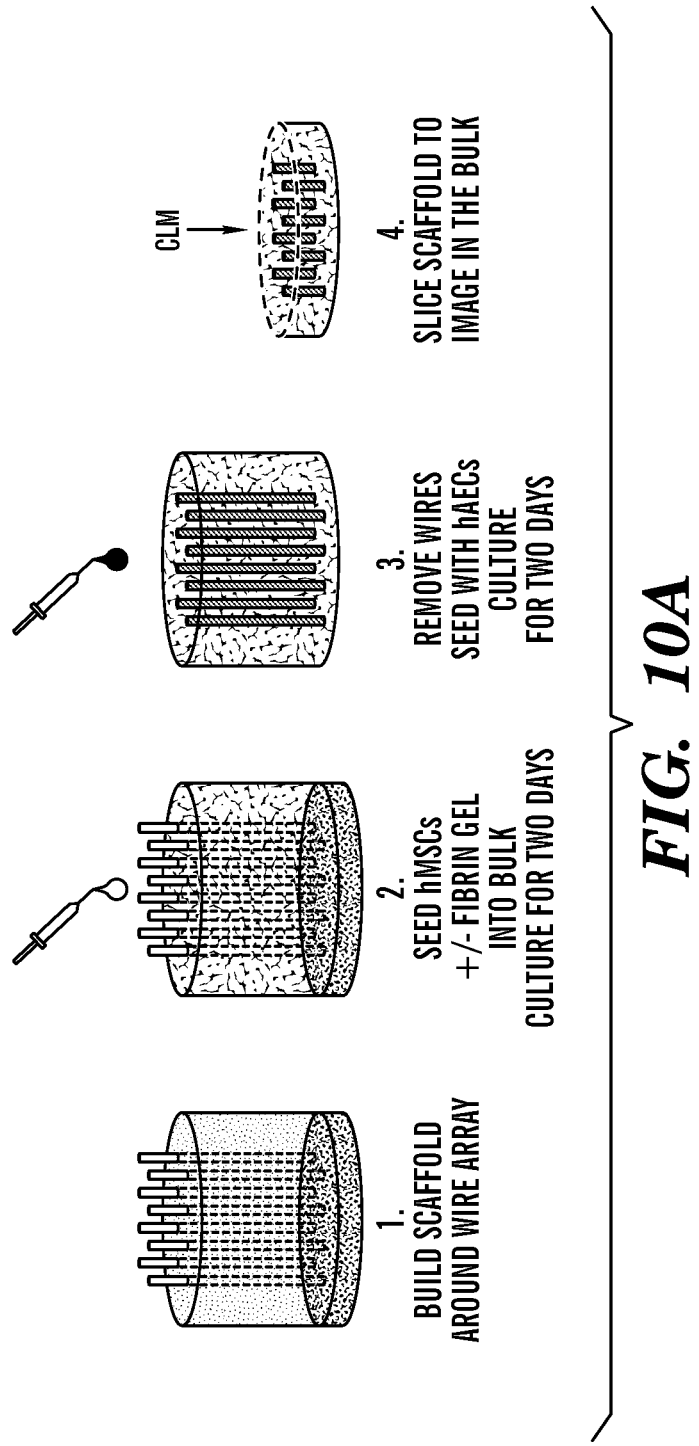
FIGS. 10A-10B show experimental data of cell compartmentalization using physical separation with LWAs.
Figure 10B:
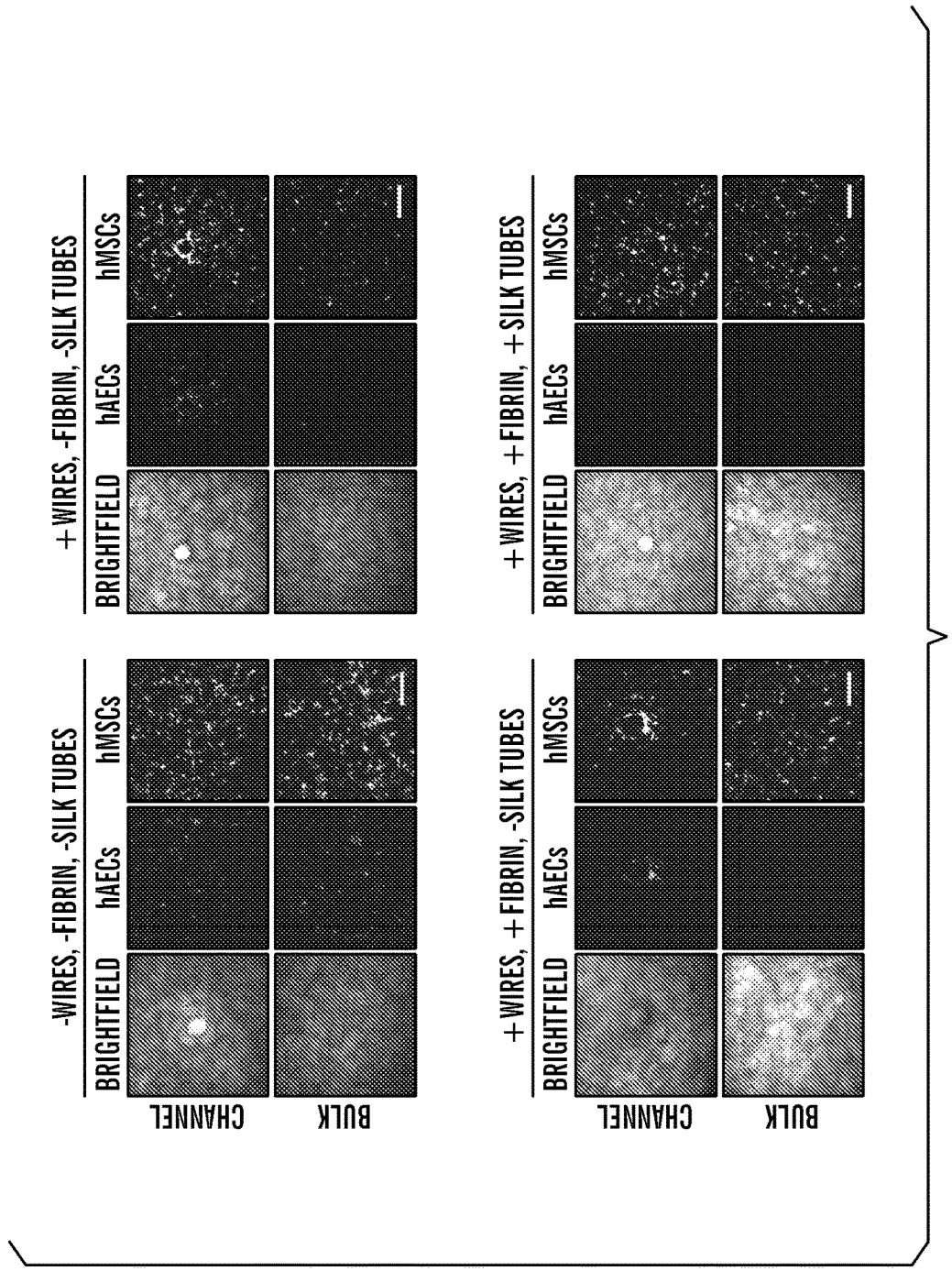

Arrays of elongated structures (e.g., LWAs) were used to encourage cell compartmentalization into different parts of the silk scaffolds, e.g., hMSCs into the scaffold bulk and hAECs into hollow channels or silk tubes. hMSCs were introduced into the scaffold bulk in the presence or absence of a fibrin gel, which can reinforce their compartmentalization. Two days post-hMSC seeding, LWAs were removed and hAECs were seeded and cultured for two days (FIG. 10A). A cross-section in the middle of each sample was imaged where a hollow channel or a silk tube was present and in the scaffold bulk away from the hollow channels or silk tubes to assess the extent of cell compartmentalization (FIG. 10B). Control samples were seeded in the absence of LWAs. When LWAs were absent (–wires, –fibrin, –silk tubes), there was no cell localization to hollow channels. Both cell types are evenly dispersed around the hollow channels and in the silk bulk. Presence of LWAs helped to localize hAECs to silk channels. hMSCs in both cases were found in the silk bulk away from the channels and in the bulk around the channels, with some localization to the channel periphery. When fibrin glue was not used (+wires, −fibrin, −silk tubes), hAECs were predominantly localized to hollow channel, but some cells migrated into the scaffold bulk near the channels. No hAECs were found in the scaffold bulk away from the hollow channels. Fibrin glue (+wires, +fibrin, −silk tubes) helped localize hAECs to the hollow channels only, with no cells found in the silk bulk near the channels or away from the channels. When silk tubes were present (+wires, +fibrin, +silk tubes), hMSCs were well dispersed throughout the scaffold bulk, however no hAECs were found in the silk tubes. This is consistent with the data shown in FIGS. 8A-8B where the silk tubes were not functionalized, but silk tube functionalization as described above can facilitate promote the level of endothelialization.

An example of a simple and versatile method of introducing nutrient delivery conduits to 3D silk-based scaffolds was described herein. The nutrient delivery conduits can be designed with a variety of channel diameters, wall-to-wall spacing, and patterns. The channel walls can be loaded with bioactive agents and that the bioactive agents remain functional and affect cellular interactions with the silk scaffold. By altering the channel wall properties, endothelialization of the channels can be modulated. The bulk of the silk-based scaffold can be systematically designed with porosity and mechanical properties that will be optimal for building the desired tissue equivalent. Depending on how the scaffolds are seeded, different cell types can be localized to the scaffold bulk and the hollow channels with varying degrees of compartmentalization. Thus, the silk-based scaffold with tunable architectures and properties can be used to build functional tissue equivalents.

Example 7

An Exemplary Method to Fabricate Laminar (Aligned or Parallel) Silk-based Scaffolds The need of a scaffolding system with laminar channels is desired for applications, e.g., for cell and matrix alignment, as circular pores generally fail to mimick most of the native matrix morphology and alignment, which can be achieved through the laminar scaffolds by culturing various cell types. Thus, the inventors have developed a method to fabricate laminar channels (parallel or aligned pores) in a silk-based scaffold. The laminar channels can act as templates to align and direct cells toward more functional tissue generation.

Exemplary materials and methods used for fabrication of laminar (aligned) channels in a silk-based scaffold is described below:

Degummed silk fibers from cocoons were used to prepare a silk solution. An exemplary protocol for preparation of degummed silk fibers from cocoons is described below (any modifications readily known to a skilled artisan, e.g., different concentrations and/or types of carbonate salts, or boiling time for degumming process, are encompassed by the protocol):

1. Cut dried cocoons (e.g., with scissors) into pieces (e.g., 4 pieces);
2. Heat a pre-determined volume of water until boiling (e.g., prepare 2 separate containers such as glass beakers filled with water (e.g., 3 L water) each and heat it up until boiling);
3. Depending on the volume of water from step (2), weigh an amount of sodium carbonate sufficient to prepare a 0.02 M sodium carbonate solution;
4. Add sodium carbonate to the container with water when water starts to boil and let it dissolve.
5. Put the cut cocoon pieces in the boiling water with 0.02 M sodium carbonate, and stir.
6. Boil for at least about 10 minutes with occasional stirring;
7. After boiling the cocoon pieces in water for at least about 10 minutes, transfer the silk fibers to a separate container with boiling water containing 0.02 M sodium carbonate.
8. Boil for at least another 10 min with occasional stirring;
9. Take the degummed fibers out of the boiling water and rinse with cold water (e.g., 5-7 washes) until most or all sodium carbonate is removed;
10. Optionally remove excess water; and
11. Air dry the degummed fibers for at least about 12 hours.

After degummed silk fibers are prepared, a silk solution can be prepared by an exemplary protocol described below (any modifications readily known to a skilled artisan, e.g., different concentrations and/or types of salts, incubation time and/or temperatures, are encompassed by the protocol):

1. Prepare a solution of Lithium Bromide (LiBr), e.g., at a concentration of about 9.3M in a container (e.g., a glass beaker);
2. Incubate the LiBr solution at about 60 C for about 10 mins (e.g., cover the LiBr solution with aluminum foil and keep the beaker in the oven at about 60° C. for 10 min);
3. Add about 10 grams of degummed silk fibers to the LiBr solution. Gentle mixing can help faster dissolution of the degummed silk fibers in the LiBr solution;
4. Keep the fibers with the LiBr solution in the oven for about 1 hr and allow it to completely dissolve. A clear solution is produced when the fibers are completely dissolved;
5. After silk fibers dissolve, perform dialysis to remove LiBr;
   a. Fill a container with distilled water;
   b. Pour the silk solution using a syringe into a dialysis cassette (12 kDa) and immerse them into the container with distilled water for dialysis; and
   c. Change water with fresh distilled water every about 1 hr for the next 4 hrs. Then change water every about 6-8 hrs for another 3-4 times.
6. After dialysis, transfer the silk solution from the dialysis cassette into a clean container (e.g., a glass beaker).
7. Centrifuge at about 5000 rpm for about 5 mins;
8. Optionally aliquot the silk solution and store at 4° C. until use;
9. If desirable, determine weight percentage of silk in a solution, e.g., by drying (e.g., in oven) about 1 ml of silk solution (e.g., in a small teflon dish) to determine the dry weight of the silk.

Figure 11A:
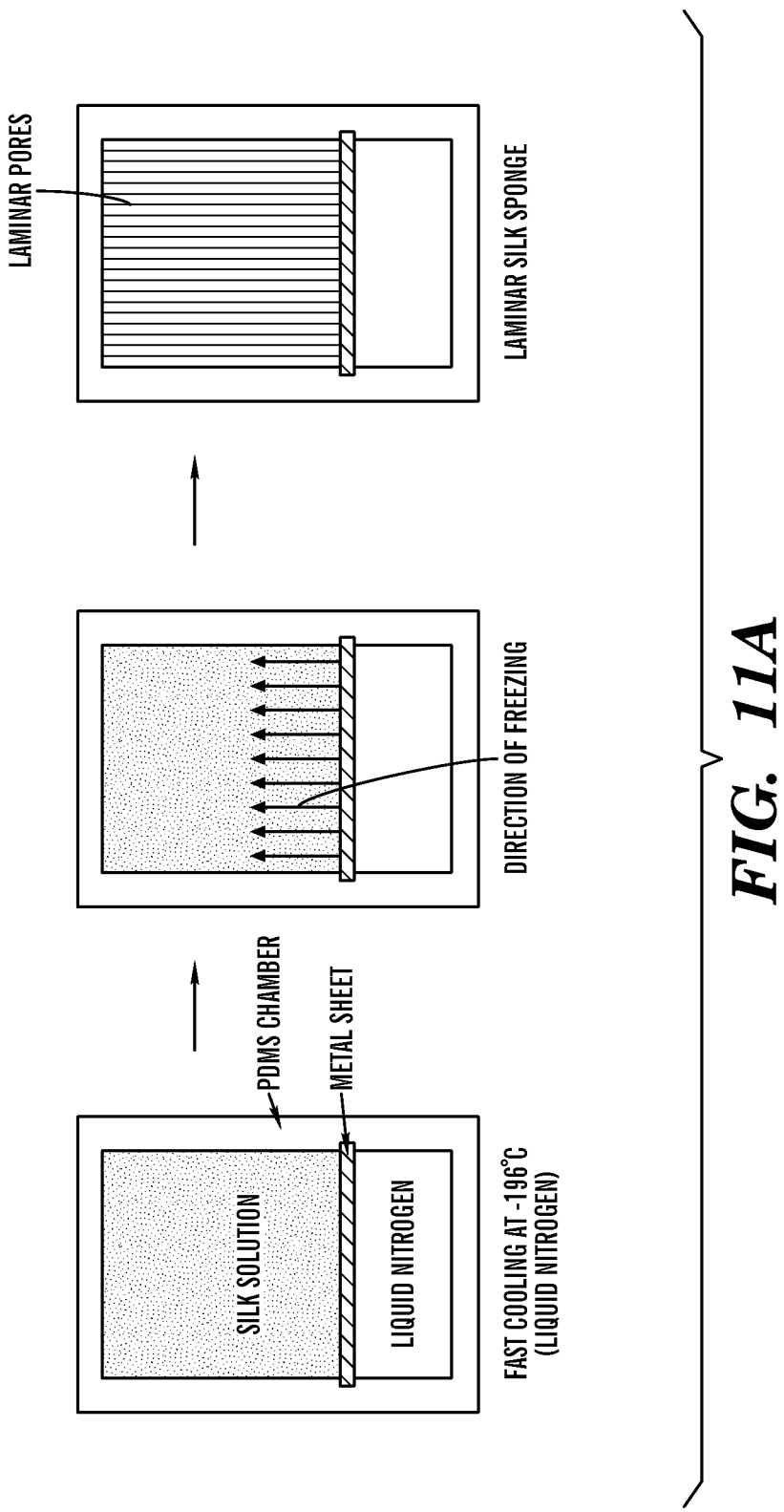
FIGS. 11A-11B show an exemplary device used to fabricate laminar (aligned or parallel) silk-based scaffolds.
Figure 11B:
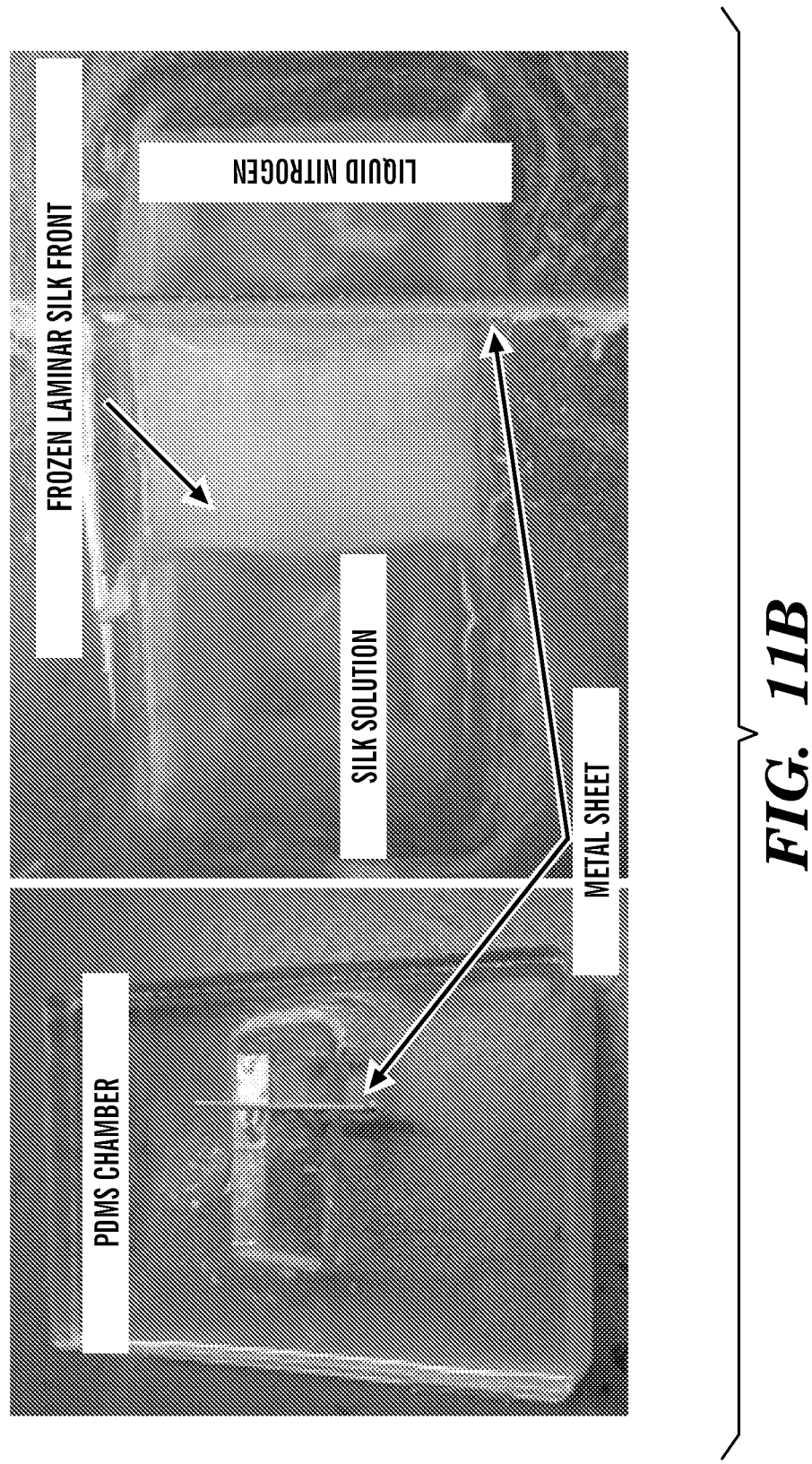

To fabricate aligned silk scaffolds with laminar channels (pores), controlled directional freezing method was performed using liquid nitrogen (e.g., at a temperature of about 196° C.). In some embodiments, a custom chamber to perform directional freezing was fabricated using polydimethylsiloxane (PDMS) (FIGS. 11A-11B). PDMS belongs to a group of polymeric organo silicon compounds that are commonly referred to as silicones. PDMS was selected as a chamber material because of its relative non-conductivity. When liquid nitrogen is poured inside the chamber, using a chamber material that is relatively heat-conductive would not be able to confer directionality to the formed pores. Thus, metal is unlikely to be used to form the entire chamber as it will cool down quickly everywhere when it is in contact with liquid nitrogen, resulting in formation of random pores due to silk freezing in all directions.

As shown in FIGS. 11A-11B, an exemplary chamber was consisted of a shallow chamber casted out of PDMS (following general method of PDMS casting by mixing the base polymer with the curing agent in the ratio of about 9:1), and the PDMS chamber was divided into smaller chambers using a metal sheet. The metal sheet cools when liquid nitrogen is poured into one chamber and which in turn cools the liquid silk on the other side of the chamber, thus initiating the process of laminar, directional pore formation. Any metal sheets that are relatively good heat conductor can be used. For example, a metal sheet can include zinc, copper, aluminum, iron, or any combinations thereof. In one embodiment, the metal sheet can include a zinc composite metal.

The size of the chamber can be altered depending on the required size of laminar scaffolds. For example, the larger the size of a laminar scaffold to be fabricated, the larger the size of the chamber is needed. A smaller laminar scaffold can be fabricated by using a smaller chamber, or by reducing a larger laminar scaffold into a smaller one. In some embodiments, depending on the chamber material, e.g., if PDMS is used, the width of a laminar scaffold (in the direction of freezing) can be no more than 3-4 cm. This is because, without wishing to be bound by theory, as the freezing front of the silk solution travels down the chamber, e.g., as shown in FIG. 11A, the temperature gradient decreases and thus becomes less effective in creating laminar channels beyond 3-4 cm. However, the length and height of the scaffold to be fabricated can be varied in accordance with different needs.

An exemplary protocol for fabrication of a laminar silk scaffold using a silk solution in a custom chamber (e.g., as shown in FIGS. 11A-11B) is described below (any modifications readily known to a skilled artisan, e.g., different low-temperature liquids, and/or different methods to increase beta sheet crystallinity, are encompassed by the protocol):

1. Pour a silk solution (e.g., ~5 wt % silk solution) into a first chamber of the PDMS mold;
2. Pour liquid nitrogen into a second chamber that is separated from the first chamber containing the silk solution by a metal sheet, where liquid nitrogen cools the metal sheet which in turn cools the silk solution leading to directional pore formation (e.g., narrow channels). Silk freezing was observed in the first chamber and appeared as laminar channels with a leading front end.
3. Maintain the second chamber at a liquid-nitrogen temperature (e.g., by replenishing the second chamber with liquid nitrogen till a desirable amount (e.g., most or all) of the silk solution freezes in the first chamber
4. Once the desirable amount (e.g., most or all) of the silk solution is frozen, dry or lyophilize the frozen silk. The time of drying, e.g., in a lyophilizer, can depend on the amount/volume of frozen silk.
5. After the frozen silk has been lyophilized till fully dried, immerse the dried silk scaffold in an alcohol solution (e.g., 80% methanol) over a period of time, e.g., overnight. Optionally, one can store the dried silk scaffold in an alcohol solution (e.g., 70% methanol solution) until use or can readily use it for applications.
6. Optionally remove the top and bottom surface or "skin" of the dried silk scaffold, e.g., by removing a thin section using sharp surgical blades, in order to open up any pores which might be closed by the top and bottom silk surface or "skin".
7. Section the dried laminar (aligned) silk scaffold into a desired size.

Figure 12B:
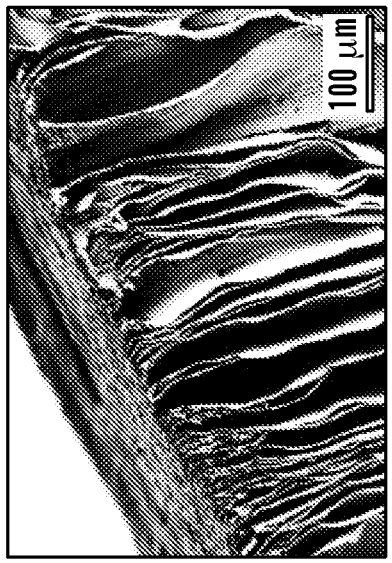
FIGS. 12A-12D are images showing aligned channels in silk scaffolds fabricated using directional freezing method.
Figure 12D:
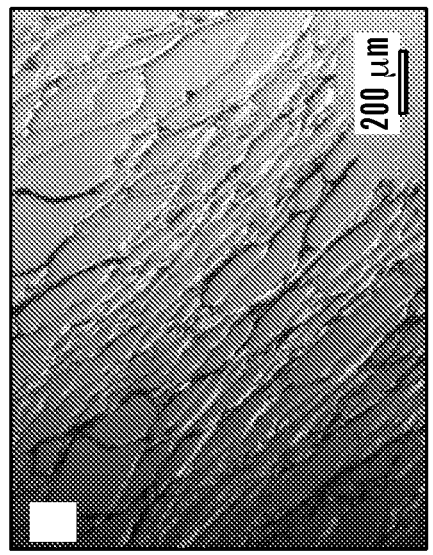
Figure 12A:
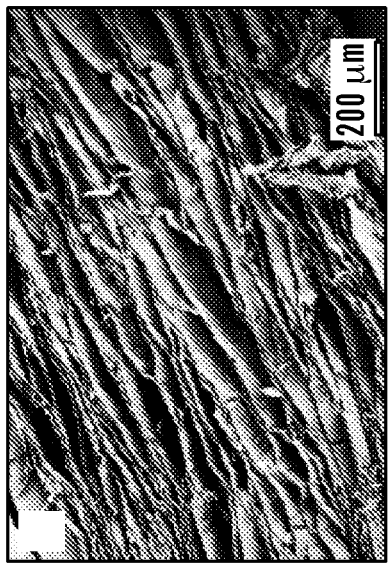
Figure 12C:
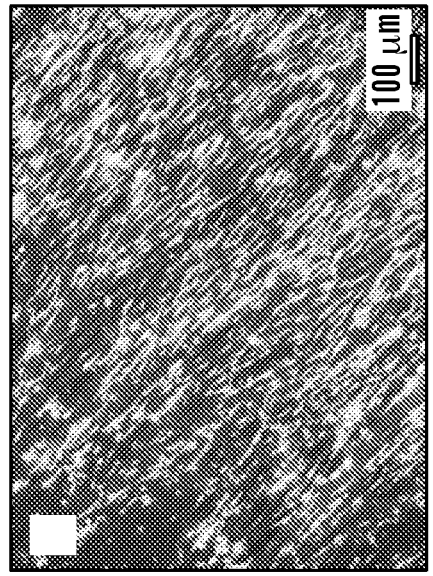
Figure 13C:
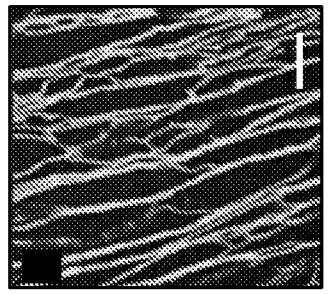
FIGS. 13A-13E are images of an exemplary lamellar silk scaffold.
Figure 13B:
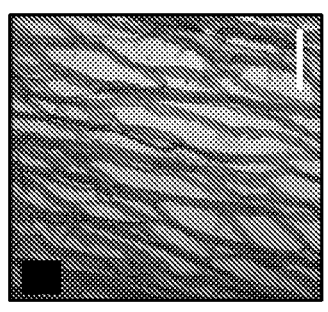
Figure 13A:
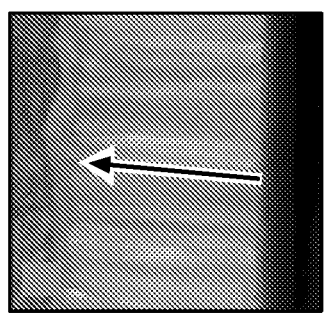
Figure 13E:
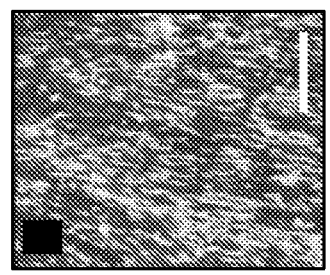
Figure 13D:
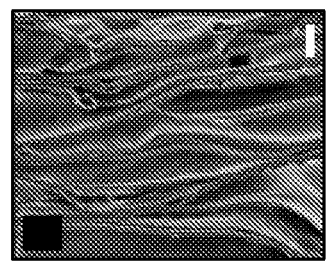
Figure 14:
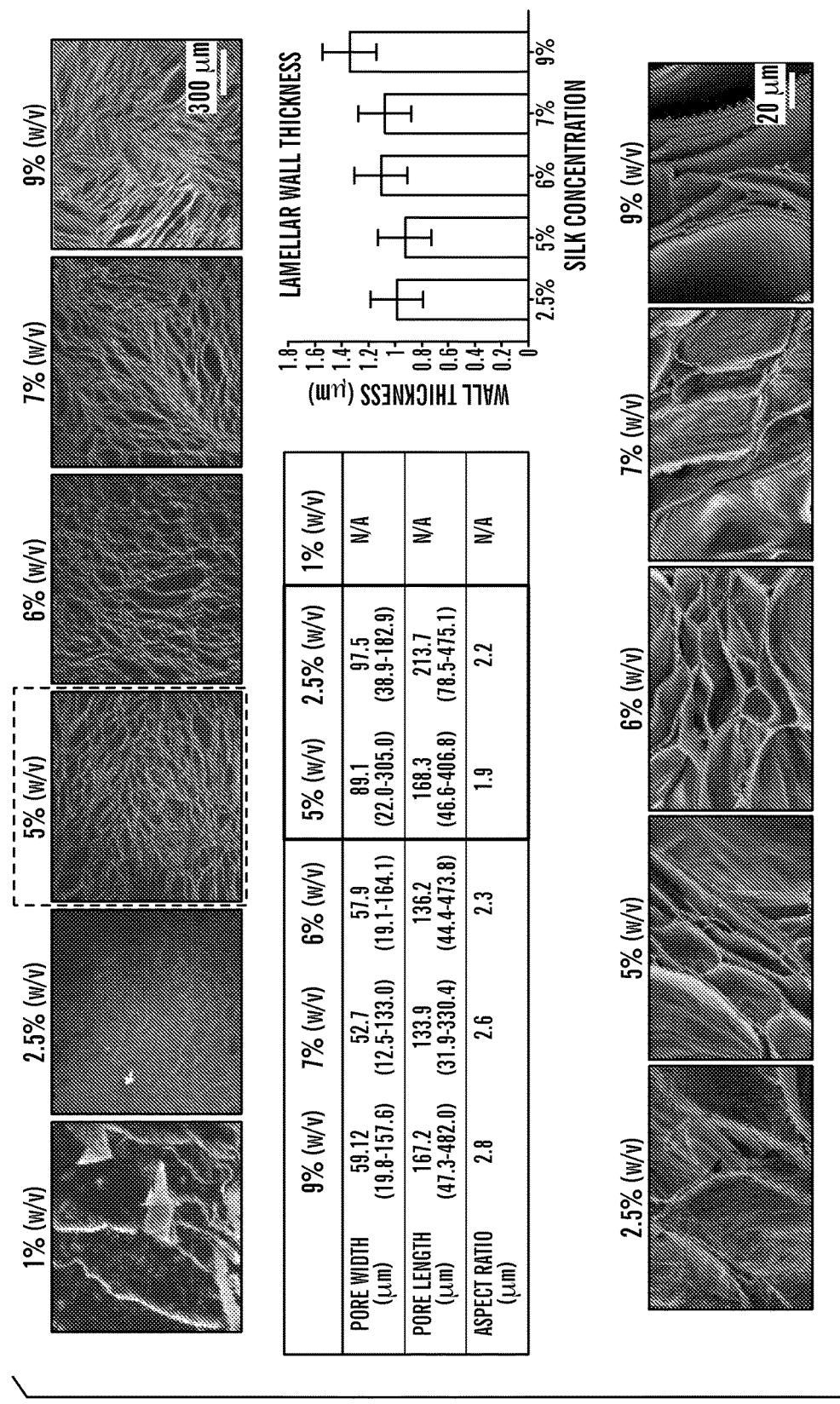
FIG. 14 show dimensions of lamellar channels formed by directional freezing of a silk solution at various concentrations. The top row shows confocal microscopy images of lamellar scaffolds formed from different concentrations of silk solution. The data table indicates effects of different silk solution concentrations on the pore width, pore length and pore aspect ratio. The bar graph indicates the lamellar wall thickness varying with different silk solution concentrations used. The bottom row shows SEM images of lamellar scaffolds formed from different concentrations of silk solution.

The silk solution concentration can vary depending on various applications or users' preference. In some embodiments, it is less desirable to use a silk solution of less than 3 wt %, because, without wishing to be bound by theory, the fabricated silk scaffolds could collapse after drying. Higher silk solution concentration can be used when higher mechanical properties are desired. However, without wishing to be bound by theory, smaller pores can be formed when higher silk solution concentrations are used. FIGS. 12A, 12B and 12D are SEM images and microtome section showing an aligned silk scaffold fabricated by a directional freezing approach as described herein, and FIG. 12C shows alignment of fluorescent protein-tagged fibroblast cells grown in the aligned silk scaffold.

Figure 15:
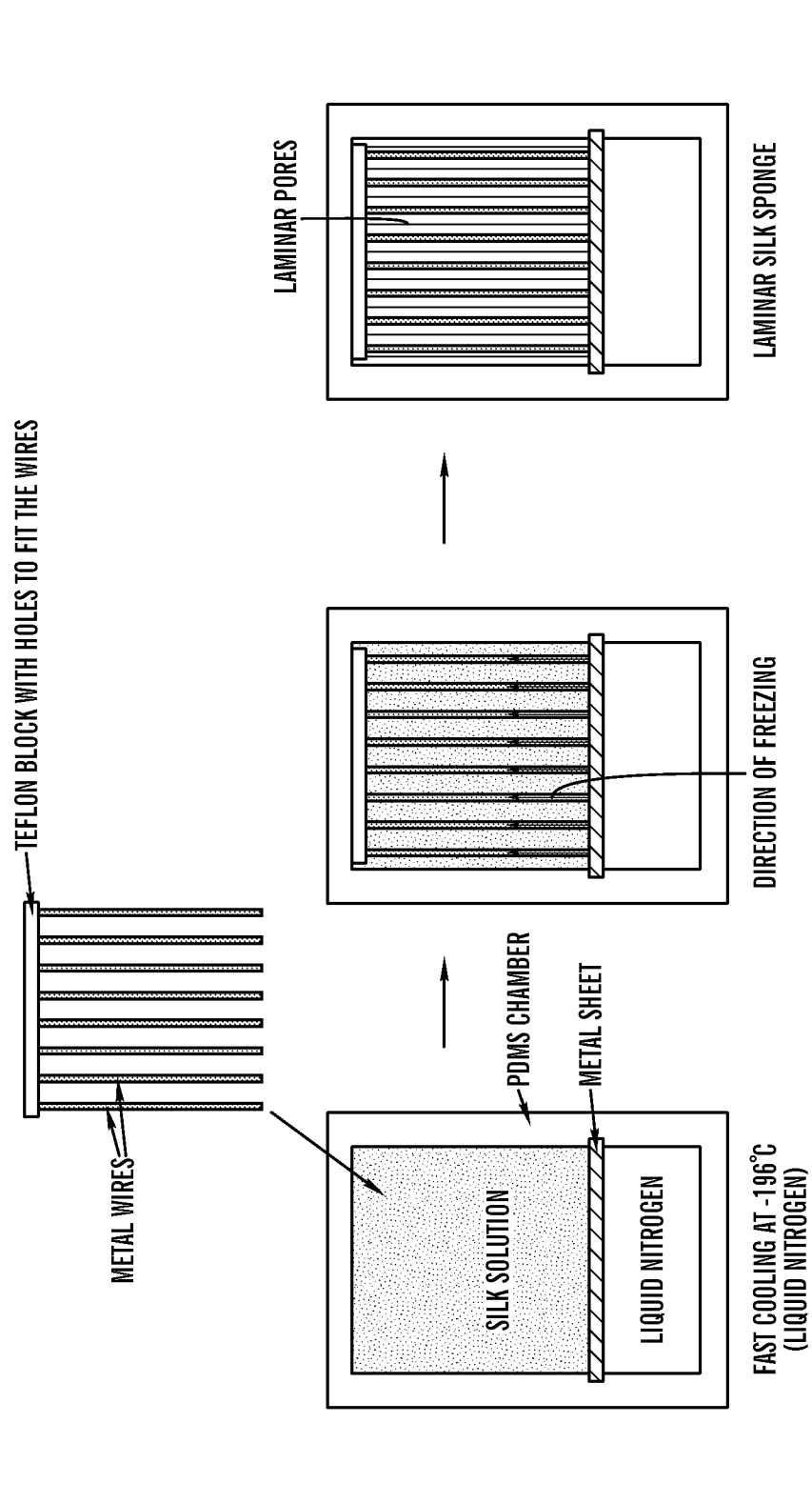
FIG. 15 is a schematic representation of the modified freezing method performed in a custom-made PDMS chamber (e.g., as shown in FIGS. 11A-11B) to achieve directional/laminar silk scaffolds with bigger pores using metal wires embedded into teflon mold.

To fabricate laminar silk scaffolds with bigger pores or hollow conduits, e.g., for nutrient delivery, in one embodiment, the aforementioned laminar silk scaffold fabrication method can be modified, e.g., placing metal wires in a silk solution before exposure of the silk solution to directional freezing. For example, numerous metal wires were embedded in a Teflon block, e.g., by making holes using a driller. In one embodiment, the wires were placed at a distance of about 2 mm from each other in all directions. This wire block was placed in the PDMS chamber as shown in FIG. 15. Silk solution was poured on top of the wires, thus creating a system where in addition to laminar channels, bigger pores (corresponding to the size of the metal wires) were formed after removal of the metal wires from a dried silk fibroin.

REFERENCES

1. ALTMAN, G. et al. Cell differentiation by mechanical stress. *The FASEB Journal* 16, 270 (2002).
2. Altman, G. H. et al. Silk-based biomaterials. *Biomaterials* 24, 401-416 (2003).
3. Asahara, T. et al. Synergistic effect of vascular endothelial growth factor and basic fibroblast growth factor on angiogenesis in vivo. *Circulation* 92, 11365-71 (1995).
4. Bagnaninchi, P. et al. Chitosan microchannel scaffolds for tendon tissue engineering characterized using optical coherence tomography. *Tissue Eng.* 13, 323-331(2007).
5. Banai, S. et al. Angiogenic-induced enhancement of collateral blood flow to ischemic myocardium by vascular endothelial growth factor in dogs. *Circulation* 89, 2183-2189 (1994).
6. Bauters, C. et al. Recovery of disturbed endothelium-dependent flow in the collateral-perfused rabbit ischemic hindlimb after administration of vascular endothelial growth factor. *Circulation* 91, 2802-2809 (1995).
7. Carletti, E., Mona, A., Migliaresi, C. & Haycock, J. Scaffolds for Tissue Engineering and 3 D Cell Culture. *Methods in Molecular Biology* 695, 17-39 (2011).
8. Flynn, L., Dalton, P. D. & Shoichet, M. S. Fiber templating of poly (2-hydroxyethyl methacrylate) for neural tissue engineering. *Biomaterials* 24, 4265-4272 (2003).

9. Fujio, Y. & Walsh, K. Akt mediates cytoprotection of endothelial cells by vascular endothelial growth factor in an anchorage-dependent manner. *J. Biol. Chem.* 274, 16349-16354 (1999).
10. Garcia-Fuentes, M., Meinel, A. J., Hilbe, M., Meinel, L. & Merkle, H. P. Silk fibroin/hyaluronan scaffolds for human mesenchymal stem cell culture in tissue engineering. *Biomaterials* 30, 5068-5076 (2009).
11. Gerber, H. P., Dixit, V. & Ferrara, N. Vascular endothelial growth factor induces expression of the antiapoptotic proteins Bcl-2 and A1 in vascular endothelial cells. *J. Biol. Chem.* 273, 13313-13316 (1998).
12. Gerber, H. P. et al. Vascular endothelial growth factor regulates endothelial cell survival through the phosphatidylinositol 3'-kinase/Akt signal transduction pathway. Requirement for Flk-1/KDR activation. *J. Biol. Chem.* 273, 30336-30343 (1998).
13. Ghaznavi, A. M., Kokai, L. E., Lovett, M. L., Kaplan, D. L. & Marra, K. G. Silk fibroin conduits: a cellular and functional assessment of peripheral nerve repair. *Ann. Plast. Surg.* 66, 273 (2011).
14. Gil, E. S. et al. Mixed Protein Blends Composed of Gelatin and *Bombyx mori* Silk Fibroin: Effects of Solvent-Induced Crystallization and Composition. *Biomacromolecules* 7, 728-735 (2006).
15. Gil, E. S. et al. Mechanical improvements to reinforced porous silk scaffolds. *Journal of Biomedical Materials Research Part A* (2011).
16. Horan, R. L. et al. In vitro degradation of silk fibroin. *Biomaterials* 26, 3385-3393 (2005).
17. Hu, X. et al. Regulation of Silk Material Structure by Temperature-Controlled Water Vapor Annealing. *Biomacromolecules* (2011).
18. Hu, X., Wang, X., Rnjak, J., Weiss, A. S. & Kaplan, D. L. Biomaterials derived from silk-tropoelastin protein systems. *Biomaterials* 31, 8121-8131(2010).
19. Lesman, A. et al. Transplantation of a tissue-engineered human vascularized cardiac muscle. *Tissue Engineering Part A* 16, 115-125 (2009).
20. Levenberg, S. et al. Engineering vascularized skeletal muscle tissue. *Nat. Biotechnol.* 23, 879-884 (2005).
21. Lokmic, Z. & Mitchell, G. M. Engineering the microcirculation. *Tissue Engineering Part B: Reviews* 14, 87-103 (2008).
22. Lovett, M. et al. Silk fibroin microtubes for blood vessel engineering. *Biomaterials* 28, 5271-5279 (2007).
23. Lu, Q. et al. Stabilization and release of enzymes from silk films. *Macromolecular bioscience* 10, 359-368 (2010).
24. Lu, Q. et al. Nanofibrous architecture of silk fibroin scaffolds prepared with a mild self-assembly process. *Biomaterials* (2010).
25. Lu, Q., Zhang, X., Hu, X. & Kaplan, D. L. Green process to prepare silk fibroin/gelatin biomaterial scaffolds. *Macromolecular bioscience* 10, 289-298 (2010).
26. Lu, S. et al. Stabilization of enzymes in silk films. *Biomacromolecules* 10, 1032-1042 (2009).
27. Lv, Q. & Feng, Q. L. Preparation of 3-D regenerated fibroin scaffolds with freeze drying method and freeze drying/foaming technique. *J. Mater. Sci. Mater. Med.* 17, 1349-1356 (2006).
28. Meinel, L. et al. The inflammatory responses to silk films in vitro and in vivo. *Biomaterials* 26, 147-155 (2005).
29. Mikos, A. G. et al. Engineering complex tissues. *Tissue Eng.* 12, 3307-3339 (2006).
30. Minoura, N., Tsukada, M. & Nagura, M. Fine structure and oxygen permeability of silk fibroin membrane treated with methanol. *Polymer* 31, 265-269 (1990).
31. Moore, M. J. et al. Multiple-channel scaffolds to promote spinal cord axon regeneration. *Biomaterials* 27, 419-429 (2006).
32. Nazhat, S. N. et al. Controlled microchannelling in dense collagen scaffolds by soluble phosphate glass fibers. *Biomacromolecules* 8, 543-551(2007).
33. Numata, K., Cebe, P. & Kaplan, D. L. Mechanism of enzymatic degradation of beta-sheet crystals. *Biomaterials* 31, 2926-2933 (2010).
34. Panilaitis, B. et al. Macrophage responses to silk. *Biomaterials* 24, 3079-3085 (2003).
35. Pritchard, E. M. & Kaplan, D. L. Silk fibroin biomaterials for controlled release drug delivery. *Expert Opinion on Drug Delivery*, 1-15 (2011).
36. Radisic, M. et al. Biomimetic approach to cardiac tissue engineering: oxygen carriers and channeled scaffolds. *Tissue Eng.* 12, 2077-2091 (2006).
37. Rouwkema, J., Boer, J. D. & Blitterswijk, C. A. V. Endothelial cells assemble into a 3-dimensional prevascular network in a bone tissue engineering construct. *Tissue Eng.* 12, 2685-2693 (2006).
38. Rouwkema, J., Rivron, N. C. & van Blitterswijk, C. A. Vascularization in tissue engineering. *Trends Biotechnol.* 26, 434-441 (2008).
39. Unger, R. et al. Endothelialization of a non-woven silk fibroin net for use in tissue engineering: growth and gene regulation of human endothelial cells. *Biomaterials* 25, 5137-5146 (2004).
40. Wang, Y. et al. In vivo degradation of three-dimensional silk fibroin scaffolds. *Biomaterials* 29, 3415-3428 (2008).
41. Wray, L. S. et al. Effect of processing on silk-based biomaterials: Reproducibility and biocompatibility. *Journal of Biomedical Materials Research Part B: Applied Biomaterials*.
42. Yeo, I. S. et al. Collagen-based biomimetic nanofibrous scaffolds: preparation and characterization of collagen/silk fibroin bicomponent nanofibrous structures. *Biomacromolecules* 9, 1106-1116 (2008).
43. Zhang, K. H., Yu, Q. Z. & Mo, X. M. Fabrication and Intermolecular Interactions of Silk Fibroin/Hydroxybutyl Chitosan Blended Nanofibers. *International Journal of Molecular Sciences* 12, 2187-2199 (2011).

Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A degradable silk scaffold system comprising:
 a porous solid-state silk matrix body; and
 a plurality of conduits comprising an array of linear channels arranged within the silk matrix body such that the spacing between the conduits is within a range of about 250 to about 2,000 micrometers.

2. The degradable silk scaffold system of claim 1, wherein the linear channels span the entire scaffold in the matrix body.

3. The degradable silk scaffold system of claim 1, wherein the linear channels have a diameter in the range of about 5 µm to about 3,000 µm, so that they are appropriately dimensioned for nutrient delivery sufficient to support confluent endothelialization.

4. The degradable silk scaffold system of claim 1, wherein the linear channels have a diameter in the range of about 10 µm to about 2,000 µm.

5. The degradable silk scaffold system of claim 1, wherein the spacing between the conduits is within a range of about 250 µm to about 1,000 µm.

6. The degradable silk scaffold system of claim 1, further comprising an active agent.

7. The degradable silk scaffold system of claim 6, wherein the active agent is selected from the group consisting of: proteins, peptides, antigens, immunogens, vaccines, antibodies or portions thereof, antibody-like molecules, enzymes, nucleic acids, siRNA, shRNA, aptamers, viruses, bacteria, small molecules, cells, therapeutic agents, nanoparticles and any combination thereof.

8. The degradable silk scaffold system of claim 7, wherein the active agent is selected from the group consisting of: collagen type I, laminin, vascular endothelial growth factor (VEGF), platelet derived growth factor (PDGF), and any combination thereof.

9. The degradable silk scaffold system of claim 1, wherein the pores in the porous solid-state silk matrix body have sizes within the range of about 25 µm to about 500 µm.

10. The degradable silk scaffold system of claim 1, wherein the porous solid-state silk matrix body has a porosity of at least about 30%.

11. The degradable silk scaffold system of claim 1, wherein the porous solid-state silk matrix body has a porosity between about 70% and about 95%.

12. The degradable silk scaffold system of claim 1, wherein the porous solid-state silk matrix body is characterized by compressive modulus of about 10 kPa to about 1,000 kPa.

13. The degradable silk scaffold system of claim 1, wherein the porous solid-state silk matrix body is characterized by compressive strength within the range of about 1 kPa to about 100 kPa.

14. The degradable silk scaffold system of claim 1, wherein the porous solid-state silk matrix body is characterized by a degradation rate to no more than 30% of its original volume in at least about 3 months after implantation.

15. The degradable silk scaffold system of claim 1, wherein the porous solid-state silk matrix body is characterized by a degradation rate to no more than 80% of its original volume in at least about 1 year after implantation.

16. The degradable silk scaffold system of claim 1, further comprising one or more photothermal elements.

17. The degradable silk scaffold system of claim 16, wherein the one or more photothermal elements comprises plasmonic nanoparticles.

18. The degradable silk scaffold system of claim 1, further comprising a cell.

* * * * *

UNITED STATES PATENT AND TRADEMARK OFFICE
CERTIFICATE OF CORRECTION

| | | |
|---|---|---|
| PATENT NO. | : 10,058,514 B2 | Page 1 of 1 |
| APPLICATION NO. | : 15/056278 | |
| DATED | : August 28, 2018 | |
| INVENTOR(S) | : Lindsay Wray et al. | |

It is certified that error appears in the above-identified patent and that said Letters Patent is hereby corrected as shown below:

In the Specification

Column 21, Line 56, "Figure SA" should be --Figure 5A--.

Column 37, Line 5, "FAT" should be --Fv--.

Column 37, Line 7, "scFy" should be --scFv--.

Column 39, Line 52, "e.g., ⌊=~" should be --e.g., Ø=~--.

Column 48, Line 43, "Banal" should be --Banai--.

Column 52, Line 62, "Mona" should be --Motta--.

Signed and Sealed this
Sixth Day of November, 2018

Andrei Iancu
*Director of the United States Patent and Trademark Office*